(12) United States Patent
Gajewski et al.

(10) Patent No.: US 9,855,302 B2
(45) Date of Patent: Jan. 2, 2018

(54) TREATMENT OF CANCER BY MANIPULATION OF COMMENSAL MICROFLORA

(71) Applicant: The University of Chicago, Chicago, IL (US)

(72) Inventors: Thomas F. Gajewski, Chicago, IL (US); Ayelet Sivan, Chicago, IL (US); Leticia Corrales, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 15/170,284

(22) Filed: Jun. 1, 2016

(65) Prior Publication Data
US 2016/0354416 A1 Dec. 8, 2016

Related U.S. Application Data

(60) Provisional application No. 62/169,112, filed on Jun. 1, 2015, provisional application No. 62/248,741, filed on Oct. 30, 2015.

(51) Int. Cl.
| | |
|---|---|
| *A61K 35/741* | (2015.01) |
| *A61K 45/06* | (2006.01) |
| *A61K 35/742* | (2015.01) |
| *A61K 35/745* | (2015.01) |
| *A61K 35/747* | (2015.01) |

(Continued)

(52) U.S. Cl.
CPC .......... *A61K 35/741* (2013.01); *A61K 35/742* (2013.01); *A61K 35/745* (2013.01); *A61K 35/747* (2013.01); *A61K 39/39558* (2013.01); *A61K 45/06* (2013.01); *C07K 16/2827* (2013.01); *A61K 2039/505* (2013.01); *C07K 2317/76* (2013.01)

(58) Field of Classification Search
CPC ... A61K 39/02; A61P 1/00; A61P 1/02; A61P 1/04; A61P 1/12; A61P 1/16; A61P 3/04; A61P 3/10; A61P 5/00; A61P 7/02; A61P 7/06; A61P 9/00; A61P 9/10; A61P 11/00; A61P 11/06; A61P 13/12; A61P 15/00; A61P 17/00; A61P 17/02
USPC .................................. 424/234.1; 435/252.1
See application file for complete search history.

(56) References Cited

U.S. PATENT DOCUMENTS

| | | | |
|---|---|---|---|
| 4,816,567 | A | 3/1989 | Cabilly et al. |
| 4,946,778 | A | 8/1990 | Ladner et al. |

(Continued)

FOREIGN PATENT DOCUMENTS

| | | |
|---|---|---|
| EP | 2876167 | 5/2015 |
| WO | WO 1988/01649 | 3/1988 |

(Continued)

OTHER PUBLICATIONS

Sharon et al., (Chin. J.Cancer. 2014. 33(9):434-444).*

(Continued)

*Primary Examiner* — Jana A Hines
(74) *Attorney, Agent, or Firm* — Casimir Jones SC; David W. Staple

(57) ABSTRACT

Provided herein are methods of treatment and/or prevention of cancer by manipulation of commensal microflora. In particular, the amount, identity, presence, and/or ratio of microflora (e.g., gut microflora) in a subject is manipulated to facilitate one or more co-treatments.

29 Claims, 45 Drawing Sheets

(51) Int. Cl.
A61K 39/395 (2006.01)
C07K 16/28 (2006.01)
A61K 39/00 (2006.01)

(56) References Cited

U.S. PATENT DOCUMENTS

| | | | |
|---|---|---|---|
| 5,260,203 A | 11/1993 | Ladner et al. | |
| 7,195,906 B2 | 3/2007 | Collins et al. | |
| 8,449,878 B2 | 5/2013 | Yonak et al. | |
| 2012/0276143 A1* | 11/2012 | O'Mahony | A23C 9/1234 424/234.1 |

FOREIGN PATENT DOCUMENTS

| | | |
|---|---|---|
| WO | WO 2011/068810 | 6/2011 |
| WO | WO 2014/145958 | 9/2014 |
| WO | WO 2015/061372 | 4/2015 |

OTHER PUBLICATIONS

Abt et al. Commensal bacteria calibrate the activation threshold of innate antiviral immunity. Immunity. Jul. 27, 2012;37(1):158-70.
Bak et al., Differential requirement for CD70 and CD80/CD86 in dendritic cell-mediated activation of tumor-tolerized CD8 T cells. J Immunol. Aug. 15, 2012;189(4):1708-16.
Blank et al. PD-L1/B7H-1 inhibits the effector phase of tumor rejection by T cell receptor (TCR) transgenic CD8+ T cells. Cancer Res. Feb. 1, 2004;64(3):1140-5.
Caporaso et al., PyNAST: a flexible tool for aligning sequences to a template alignment. Bioinformatics. Jan. 15, 2010;26(2):266-7.
Caporaso et al., QIIME allows analysis of high-throughput community sequencing data. Nat Methods. May 2010;7(5):335-6.
Clackson et al., Making antibody fragments using phage display libraries. Nature. Aug. 15, 1991;352(6336):624-8.
Compeer et al., Antigen processing and remodeling of the endosomal pathway: requirements for antigen cross-presentation. Front Immunol. Mar. 7, 2012;3:37.
Dong et al., The role of intestinal bifidobacteria on immune system development in young rats. Early Hum Dev. Jan. 2010;86(1):51-8.
Fuertes et al., Host type I IFN signals are required for antitumor CD8+ T cell responses through CD8{alpha}+ dendritic cells. J Exp Med. Sep. 26, 2011;208(10):2005-16.
Gajewski et al., Gene signature in melanoma associated with clinical activity: a potential clue to unlock cancer immunotherapy. Cancer J. Jul.-Aug. 2010;16(4):399-403.
Ganal et al., Priming of natural killer cells by nonmucosal mononuclear phagocytes requires instructive signals from commensal microbiota. Immunity. Jul. 27, 2012;37(1):171-86.
Goto et al., Segmented filamentous bacteria antigens presented by intestinal dendritic cells drive mucosal Th17 cell differentiation. Immunity. Apr. 17, 2014;40(4):594-607.
Hamid et al., Safety and tumor responses with lambrolizumab (anti-PD-1) in melanoma. N Engl J Med. Jul. 11, 2013;369(2):134-44.
Harlow, et al. Antibodies: A Laboratory Manual Ch. 6, (Cold Spring Harbor Laboratory, Cold Spring Harbor, N.Y.) 1988.
Hodi et al., Improved Survival with Ipilimumab in Patients with Metastatic Melanoma. N Engl J Med. Aug. 19, 2010;393(8):711-723.
Hudson et al., Engineered antibodies. Nat Med. Jan. 2003;9(1):129-34.
Iida et al., Commensal bacteria control cancer response to therapy by modulating the tumor microenvironment. Science. Nov. 22, 2013;342(6161):967-70.
Ivanov et al., Induction of intestinal Th17 cells by segmented filamentous bacteria. Cell. Oct. 30, 2009;139(3):485-98.
Jancic et al., Rab27a regulates phagosomal pH and NADPH oxidase recruitment to dendritic cell phagosomes. Nat Cell Biol. Apr. 2007;9(4):367-78.
Ji et al., An immune-active tumor microenvironment favors clinical response to ipilimumab. Cancer Immunol Immunother. Jul. 2012;61(7):1019-31.
Kabashima et al., CXCL12-CXCR4 engagement is required for migration of cutaneous dendritic cells. Am J Pathol. Oct. 2007;171(4):1249-57.
Kohler et al., Continuous cultures of fused cells secreting anitbody of predefined specificity. Nature. 1975;256:495-497.
Lopez et al., Distinct Bifidobacterium strains drive different immune responses in vitro. Int J Food Microbiol. Mar. 31, 2010;138(1-2):157-65.
Lozupone et al., UniFrac: a new phylogenetic method for comparing microbial communities. Appl Environ Microbiol. Dec. 2005;71(12):8228-35.
Mackey et al., Dendritic cells require maturation via CD40 to generate protective antitumor immunity. J Immunol. Sep. 1, 1998;161(5):2094-8.
Marks et al., By-passing Immunization: Human Antibodies from V-gene Libraries Displayed on Phage. J. Mol. Biol. 1991;222:581-597.
Mazmanian et al., An immunomodulatory molecule of symbiotic bacteria directs maturation of the host immune system. Cell. Jul. 15, 2005;122(1):107-18.
McDonald et al., An improved Greengenes taxonomy with explicit ranks for ecological and evolutionary analyses of bacteria and archaea. ISME J. Mar. 2012;6(3):610-8.
Menard et al., Gnotobiotic mouse immune response induced by *Bifidobacterium* sp. strains isolated from infants. Appl Environ Microbiol. Feb. 2008;74(3):660-6.
Nukiwa et al., Dendritic cells modified to express fractalkine/CX3CL1 in the treatment of preexisting tumors. Eur J Immunol. Apr. 2006;36(4):1019-27.
Pan et al., Interferon-gamma is an autocrine mediator for dendritic cell maturation. Immunol Lett. Jun. 15, 2004;94(1-2):141-51.
Pettit et al., Nuclear localization of RelB is associated with effective antigen-presenting cell function. J Immunol. Oct. 15, 1997;159(8):3681-91.
Round et al., Inducible Foxp3+ regulatory T-cell development by a commensal bacterium of the intestinal microbiota. Proc Natl Acad Sci U S A. Jul. 6, 2010;107(27):12204-9.
Scholer et al., Intercellular adhesion molecule-1-dependent stable interactions between T cells and dendritic cells determine CD8+ T cell memory. Immunity. Feb. 2008;28(2):258-70.
Sivan et al., Commensal Bifidobacterium promotes antitumor immunity and facilitates anti-PD-L1 efficacy. Science. Nov. 27, 2015;350(6264):1084-9.
Spranger et al., Up-regulation of PD-L1, IDO, and T(regs) in the melanoma tumor microenvironment is driven by CD8(+) T cells. Sci Transl Med. Aug. 28, 2013;5(200):200ra116.
Stober et al., Slc11a1, formerly Nramp1, is expressed in dendritic cells and influences major histocompatibility complex class II expression and antigen-presenting cell function. Infect Immun. Oct. 2007;75(10):5059-67.
Topalian et al., Safety, activity, and immune correlates of anti-PD-1 antibody in cancer. N Engl J Med. Jun. 28, 2012;366(26):2443-54.
Topalian et al., Survival, durable tumor remission, and long-term safety in patients with advanced melanoma receiving nivolumab. J Clin Oncol. Apr. 1, 2014;32(10):1020-30.
Tumeh et al., PD-1 blockade induces responses by inhibiting adaptive immune resistance. Nature. Nov. 27, 2014;515(7528):568-71.
Viaud et al., The intestinal microbiota modulates the anticancer immune effects of cyclophosphamide. Science. Nov. 22, 2013;342(6161):971-6.
Wang et al., Naive Bayesian classifier for rapid assignment of rRNA sequences into the new bacterial taxonomy. Appl Environ Microbiol. Aug. 2007;73(16):5261-7.
Wolchok et al., Nivolumab plus ipilimumab in advanced melanoma. N Engl J Med. Jul. 11, 2013;369(2):122-33.
Woo et al., STING-dependent cytosolic DNA sensing mediates innate immune recognition of immunogenic tumors. Immunity. Nov. 20, 2014;41(5):830-42.

(56) References Cited

OTHER PUBLICATIONS

Wu et al., Gut-residing segmented filamentous bacteria drive autoimmune arthritis via T helper 17 cells. Immunity. Jun. 25, 2010;32(6):815-27.
Zhang et al., Intratumoral T Cells, Recurrence, and Survival in Epithelial Ovarian Cancer. N Engl J Med. 2003;348:2013-213.
Zitvogel et al., Cancer and the gut microbiota: an unexpected link. Sci Transl Med. Jan. 21, 2015;7(271):271ps1.
International Search Report and Written Opinion for PCT/US2016/035228, dated Aug. 30, 2016, 15 pages.

\* cited by examiner

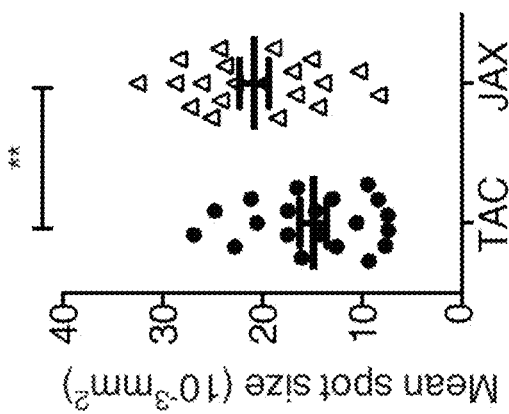
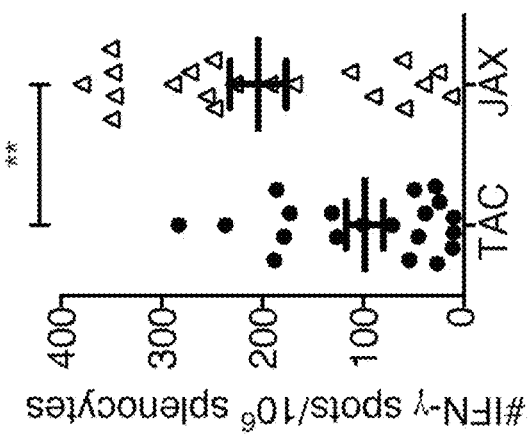
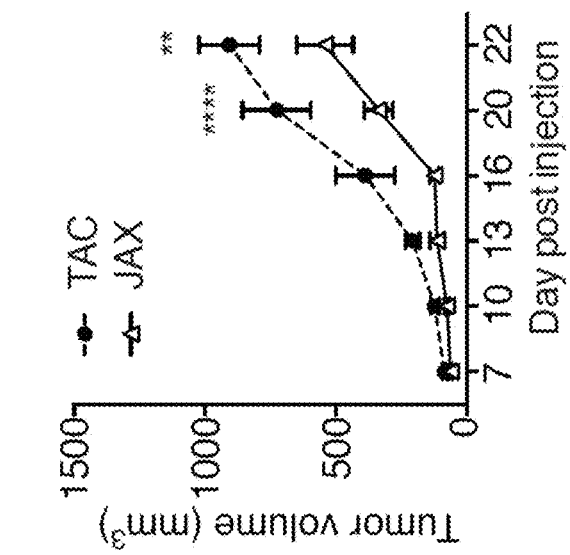
FIG. 1A
FIG. 1B
FIG. 1C

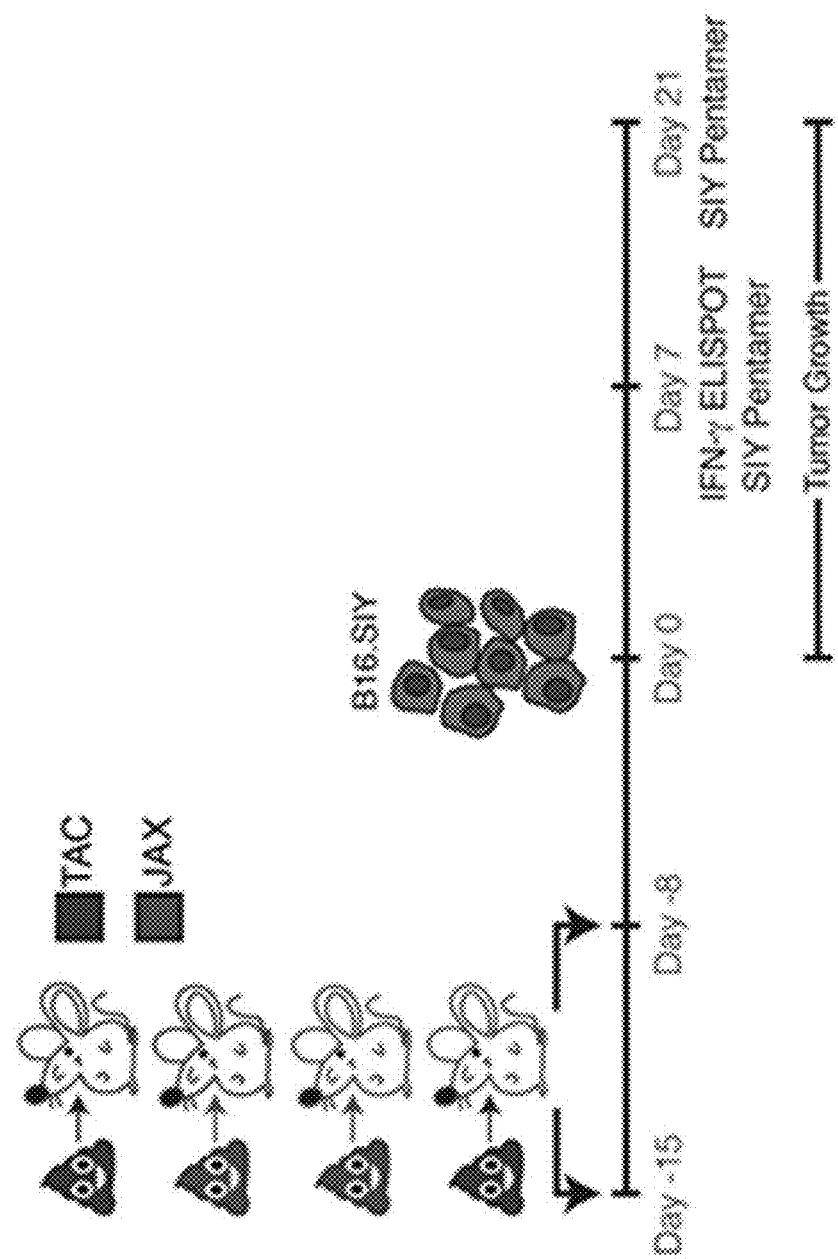

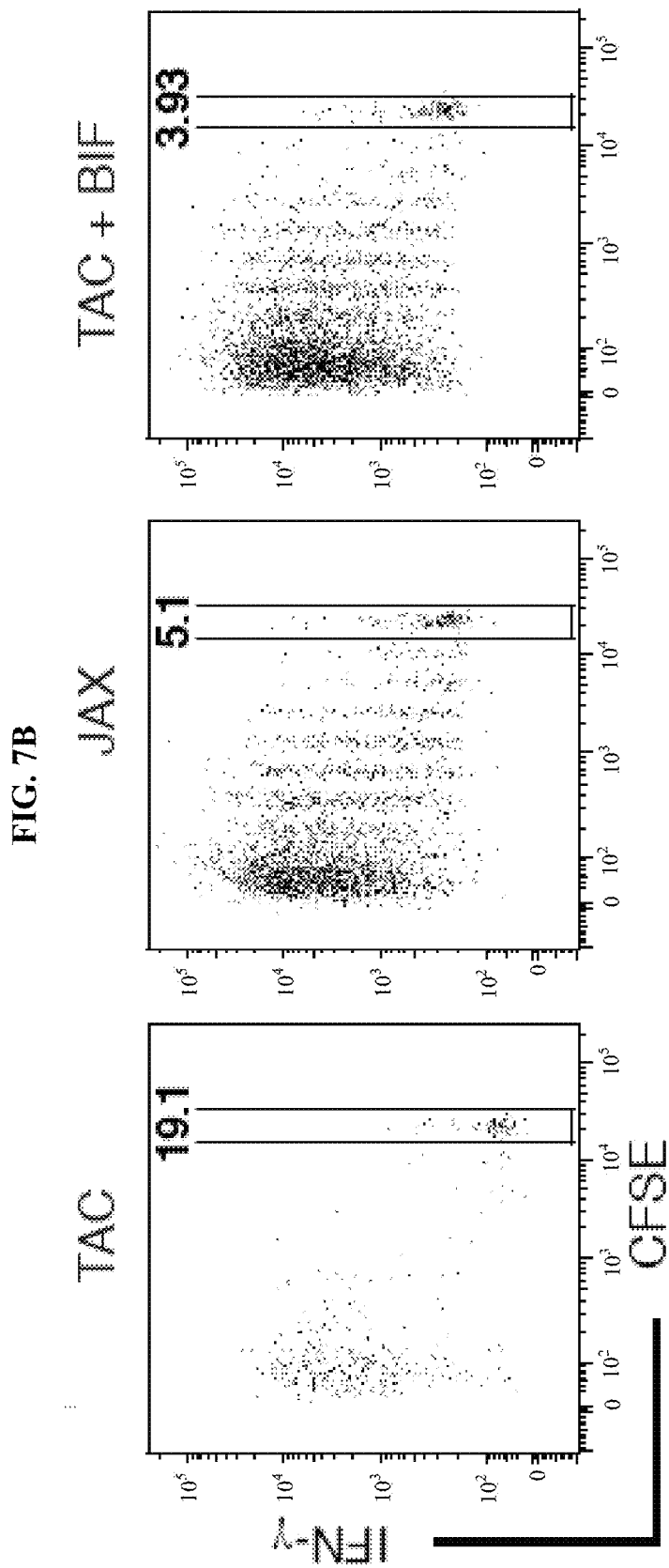

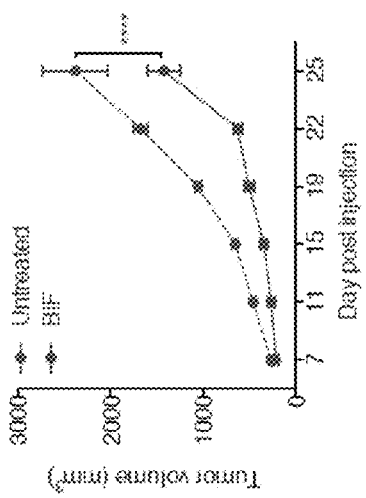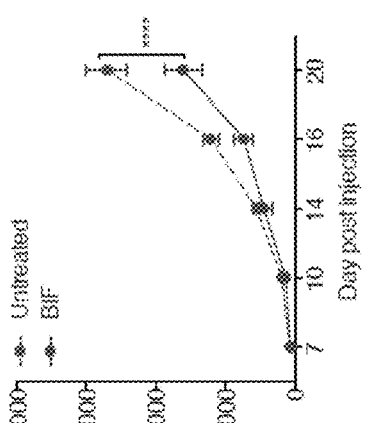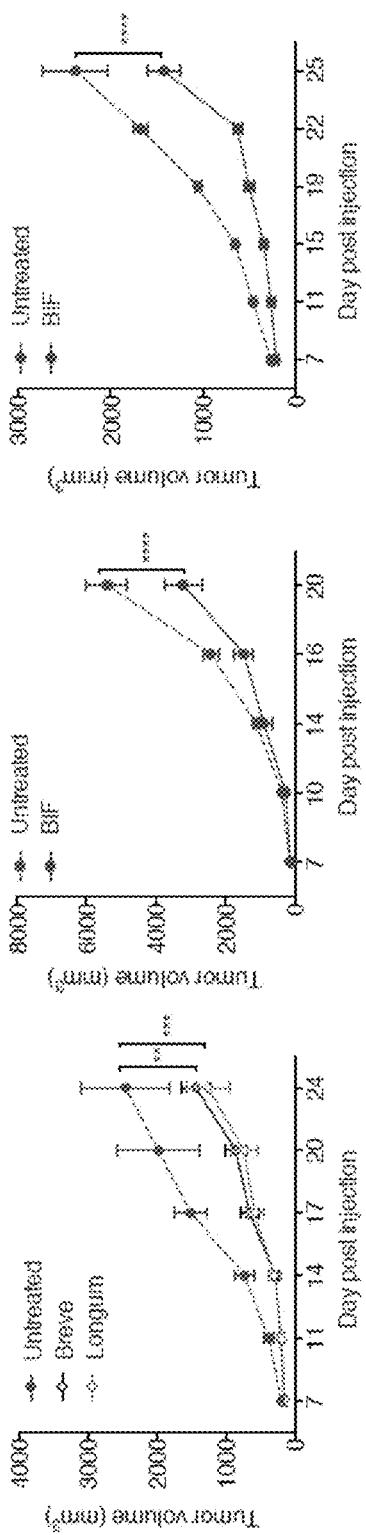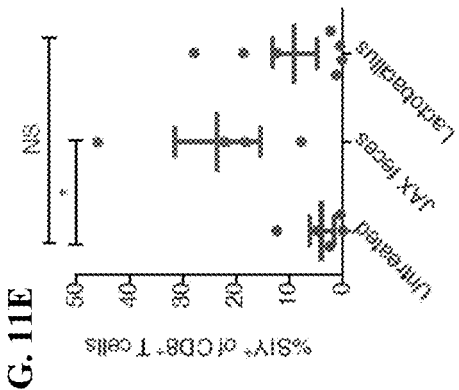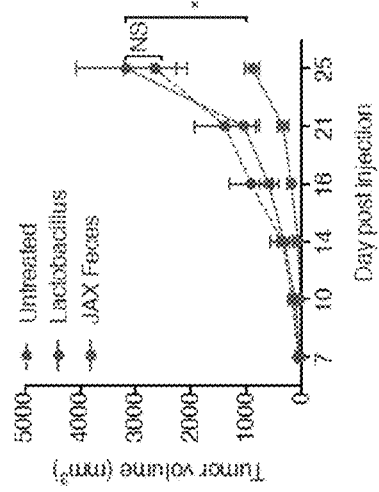
FIG. 11A
FIG. 11B
FIG. 11C
FIG. 11D
FIG. 11E

TREATMENT OF CANCER BY MANIPULATION OF COMMENSAL MICROFLORA

CROSS-REFERENCE TO RELATED APPLICATIONS

The present application claims the priority benefit of U.S. Provisional Patent Application 62/169,112, filed Jun. 1, 2015, and U.S. Provisional Patent Application 62/248,741, filed Oct. 30, 2015, each of which is incorporated by reference in its entirety.

FIELD

Provided herein are methods of treatment and/or prevention of cancer by manipulation of commensal microflora. In particular, the amount, identity, presence, and/or ratio of microflora (e.g., gut microflora) in a subject is manipulated to facilitate one or more co-treatments.

BACKGROUND

Harnessing the host immune system constitutes a promising approach for the treatment of cancer because of its potential to specifically target tumor cells while limiting harm to normal tissue, with durability of benefit associated with immunologic memory. Enthusiasm has been fueled by recent clinical success, particularly with antibodies that block immune inhibitory pathways, specifically CTLA-4 and the PD-1/PD-L1 axis (Hodi et al. The New England journal of medicine 363, 711-723 (2010); Hamid et al. The New England journal of medicine 369, 134-144 (2013); herein incorporated by reference in their entireties). Early data have indicated that clinical responses to these immunotherapies are more frequent in patients who show evidence of an endogenous T cell response ongoing in the tumor microenvironment at baseline (Tumeh et al. Nature 515, 568-571 (2014); Spranger et al. Science translational medicine 5, 200ra116 (2013); Ji et al. Cancer immunology, immunotherapy: CII 61, 1019-1031 (2012); Gajewski et al. Cancer journal 16, 399-403 (2010); herein incorporated by reference in their entireties). Despite the functional and clinical importance of this T cell-inflamed tumor microenvironment, the mechanisms that govern the presence or absence of this phenotype have not been well understood. Theoretical sources of inter-patient heterogeneity include germline genetic differences at the level of the host, variability in patterns of somatic alterations in tumor cells, and environmental differences with the potential to impact on systemic immunity.

SUMMARY

Provided herein are methods of treatment and/or prevention of cancer by manipulation of commensal microflora. In particular, the amount, identity, presence, and/or ratio of microflora (e.g., gut microflora) in a subject is manipulated to facilitate one or more co-treatments.

In some embodiments, provided herein are methods of treating or preventing cancer in a subject, comprising modulating levels of one or more commensal microbes within the subject to: (A) enhance an immune response by the subject, (B) inhibit the growth or spread of the cancer, (C) inhibit immune evasion by the cancer, and/or (D) enhance the efficacy of a therapeutic. In some embodiments, the levels of one or more commensal microbes are modulated within the gut of the subject. In some embodiments, modulating the levels of one or more commensal microbes comprises increasing and/or decreasing levels of one or more bacterial selected from the genera *Adlercreutzia, Oscillopira, Mollicutes, Butyrivibrio, Bacteroides, Clostridium, Fusobacterium, Eubacterium, Ruminococcus, Peptococcus, Peptostreptococcus, Bifidobacterium, Rikenella, Alistipes, Marinilabilia, Anaerostipes, Escherichia*, and/or *Lactobacillus*.

In some embodiments, modulating the levels of one or more commensal microbes comprises administering a beneficial microbes to the subject. In some embodiments, the beneficial microbes are bacteria. In some embodiments, the bacteria are selected from the genera *Adlercreutzia, Oscillopira, Mollicutes, Butyrivibrio, Bacteroides, Clostridium, Fusobacterium, Eubacterium, Ruminococcus, Peptococcus, Peptostreptococcus, Bifidobacterium, Rikenella, Alistipes, Marinilabilia, Anaerostipes, Escherichia*, and/or *Lactobacillus*. In some embodiments, the bacteria are *Bifidobacterium*. In some embodiments, the *Bifidobacterium* include bacteria selected from the group consisting of *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*. In some embodiments, the beneficial microbes are administered as a probiotic composition or via microflora transplant from a donor.

In some embodiments, modulating the levels of one or more commensal microbes comprises administering one or more antimicrobials. In some embodiments, the antimicrobial kills detrimental microbes. In some embodiments, the antimicrobial is an antibiotic. In some embodiments, methods further comprise administration of beneficial microbes to the subject.

In some embodiments, methods further comprise administering to the subject a cancer therapy. In some embodiments, wherein the modulating levels of one or more commensal microbes within the subject enhances an immune response by the subject and/or inhibits immune evasion by the cancer, and the cancer therapy is an immunotherapy. In some embodiments, the immunotherapy comprises administration of anti-CTLA-4 antibodies and/or anti-PD-L1 or anti-PD-1 antibodies. In some embodiments, wherein the modulating levels of one or more commensal microbes within the subject enhance the efficacy of a therapeutic, and the cancer therapy is said therapeutic. In some embodiments, the therapeutic comprises a chemotherapeutic. In some embodiments, methods further comprise testing the subject for immune evasion by the cancer. In some embodiments, methods further comprise surgical, radiation, and/or chemotherapeutic cancer intervention.

In some embodiments, provided herein are kits or compositions comprising a beneficial commensal microbe and a cancer therapeutic, said compositions or components of said kits formulated for therapeutic delivery to a subject.

In some embodiments, provided herein are beneficial commensal microbes for use as a medicament in the treatment of cancer and/or inhibition of immune evasion.

In some embodiments, provided herein are methods of treating or preventing cancer in a subject comprising administering to the subject bacterial formulation comprising bacteria of the genera *Bifidobacterium, Rikenella, Alistipes, Marinilabilia*, or *Anaerostipes*. In some embodiments, at least 50% of the bacteria in the bacterial formulation are of the genera *Bifidobacterium, Rikenella, Alistipes, Marinil-*

*abilia*, or *Anaerostipes*. In some embodiments, at least 90% of the bacteria in the bacterial formulation are of the genera *Bifidobacterium*, *Rikenella*, *Alistipes*, *Marinilabilia*, or *Anaerostipes*. In some embodiments, the bacterial formulation comprise bacteria of the genus *Bifidobacterium*. In some embodiments, at least 50% of the bacteria in the bacterial formulation are of the genus *Bifidobacterium*. In some embodiments, at least 90% of the bacteria in the bacterial formulation are of the genus *Bifidobacterium*.

In some embodiments, the bacteria of genus *Bifidobacterium* are selected from the group consisting of *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, *Bifidobacterium angulatum*, *Bifidobacterium asteroides*, *Bifidobacterium boum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium indicum*, *Bifidobacterium inopinatum*, *Bifidobacterium magnum*, *Bifidobacterium merycicum*, *Bifidobacterium minimum*, *Bifidobacterium pseudolongum*, *Bifidobacterium pullorum*, *Bifidobacterium psychraerophilum*, *Bifidobacterium ruminantium*, *Bifidobacterium saeculare*, *Bifidobacterium scardovii*, *Bifidobacterium simiae*, *Bifidobacterium subtile*, *Bifidobacterium therammcidophilum*, *Bifidobacterium thermophilum*, *Bifidobacterium tsurumiense*, *Bifidobacterium urinalis*, *Bifidobacterium* sp.

In some embodiments, the cancer is cancer is selected from the group consisting of acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, telangiectaltic sarcoma, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

In some embodiments, the subject is human. In some embodiments, the bacterial formulation is administered by oral administration, rectal administration, topical administration, inhalation or injection. In some embodiments, the bacterial formulation is a food product. In some embodiments, the bacterial formulation comprises at least about $5 \times 10^6$ CFU of bacteria. In some embodiments, the bacterial formulation is administered to the subject in two or more doses. In some embodiments, the administration of at least two of the two or more doses are separated by at least 1 day. In some embodiments, the administration of at least two of the two or more doses are separated by at least 1 week.

In some embodiments, methods further comprise administering to the subject an antibiotic. In some embodiments, the antibiotic is administered to the subject before the bacterial formulation. In some embodiments, the antibiotic is administered to the subject at least 1 day before the bacterial formulation is administered to the subject.

In some embodiments, methods further comprise administering to the subject an immune checkpoint inhibitor. In some embodiments, the immune checkpoint inhibitor is a protein or polypeptide that specifically binds to an immune checkpoint protein. In some embodiments, the immune checkpoint protein is selected from the group consisting of CTLA4, PD-1, PD-L1, PD-L2, A2AR, B7-H3, B7-H4, BTLA, KIR, LAG3, TIM-3 or VISTA. In some embodiments, the polypeptide or protein is an antibody or antigen-binding fragment thereof. In some embodiments, the immune checkpoint inhibitor is an interfering nucleic acid molecule. In some embodiments, the interfering nucleic acid molecule is an siRNA molecule, an shRNA molecule or an antisense RNA molecule. In some embodiments, the immune checkpoint inhibitor is selected from the group consisting of nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010. In some embodiments, the immune checkpoint inhibitor is administered before the bacterial formulation. In some embodiments, the immune checkpoint inhibitor is administered at least one day before the bacterial formulation. In some embodiments, the immune checkpoint is administered at about the same time as the bacterial formulation. In some embodiments, the immune checkpoint inhibitor is administered on the same day as the bacterial formulation. In some embodiments, the immune checkpoint inhibitor is administered after the bacterial formulation. In some embodiments, the immune checkpoint inhibitor is administered at least one day after the bacterial formulation. In some embodiments, the immune checkpoint inhibitor is administered by injection. In some embodiments, the injection is an intravenous, intramuscular, intratumoral or subcutaneous injection.

In some embodiments, provided herein are methods of treating cancer in a human subject comprising administering to the subject an immune checkpoint inhibitor and a bacterial formulation comprising bacteria of the genera *Bifidobacterium*. In some embodiments, at least 50% (e.g., 50%, 55%, 60%, 65%, 70%, 75%, 80%, 85%, 90%, 95%, 99%, or more, or ranges therebetween) of the bacteria in the bacterial formulation are of the genera *Bifidobacterium*. In some embodiments, at least 90% (e.g., 90%, 95%, 99%, 99.9%, 99.99%, or more or ranges therebetween) of the bacteria in the bacterial formulation are of the genera *Bifidobacterium*. In some embodiments, the bacteria of the genus *Bifidobacterium* comprise bacteria of the species *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, *Bifidobacterium angulatum*, *Bifidobacterium asteroides*, *Bifidobacterium boum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium indicum*, *Bifidobacterium inopinatum*, *Bifidobacterium magnum*, *Bifidobacterium merycicum*, *Bifidobacterium minimum*, *Bifidobacterium pseudolongum*, *Bifidobacterium pullorum*, *Bifidobacterium psychraerophilum*, *Bifidobacterium ruminantium*, *Bifidobacterium saeculare*, *Bifidobacterium scardovii*, *Bifidobacterium simiae*, *Bifidobacterium subtile*, *Bifidobacterium therammcidophilum*, *Bifidobacterium thermophilum*, *Bifidobacterium tsurumiense*, *Bifidobacterium urinalis* or *Bifidobacterium* sp. In some embodiments, the bacterial formulation is administered by oral administration or rectal administration. In some embodiments, the bacterial formulation is administered by oral administration. In some embodiments, the bacterial formulation comprises at least $5 \times 10^6$ CFU (e.g., $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 10^{12}$ CFU, $2 \times 10^{12}$ CFU, $5 \times 10^{12}$ CFU, or more or ranges therebetween) of bacteria of the genera *Bifidobacterium*. In some embodiments, the bacterial formulation is administered to the subject in two or more doses (e.g., 2, 3, 4, 5, 6, 7, 8, 9, 10, or more, or ranges therebetween). In some embodiments, the administration of doses are separated by at least 1 week. In some embodiments, methods further comprise administering to the subject an antibiotic prior to the administration of the bacterial formulation. In some embodiments, the antibiotic is administered to the subject at least 1 day before the bacterial formulation is administered to the subject. In some embodiments, the immune checkpoint inhibitor is a protein or polypeptide that binds to an immune checkpoint protein. In some embodiments, the immune checkpoint inhibitor is an antibody or antigen binding fragment thereof that binds to an immune checkpoint protein. In some embodiments, the immune checkpoint protein is CTLA4, PD-1, PD-L1, PD-L2, A2AR, B7-H3, B7-H4, BTLA, KIR, LAG3, TIM-3 or VISTA. In some embodiments, the immune checkpoint protein is PD-1 or PD-L1. In some embodiments, the immune checkpoint inhibitor is nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010. In some embodiments, the immune checkpoint inhibitor is administered by intravenous injection, intramuscular injection, intratumoral injection or subcutaneous injection.

In some embodiments, provided herein are methods of treating cancer in a human subject comprising administering to the subject a bacterial formulation comprising at least $5 \times 10^6$ CFU (e.g., $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 10^{12}$ CFU, $2 \times 10^{12}$ CFU, $5 \times 10^{12}$ CFU, or more or ranges therebetween) of bacteria of the genera *Bifidobacterium*, wherein at least 50% (e.g., 50%, 55%, 60%, 65%, 70%, 75%, 80%, 85%, 90%, 95%, 99%, or more, or ranges therebetween) of the bacteria in the bacterial formulation are of the genera *Bifidobacterium*. In some embodiments, at least 90% (e.g., 90%, 95%, 99%, 99.9%, 99.99%, or more or ranges therebetween) of the bacteria in the bacterial formulation are of the genera *Bifidobacterium*. In some embodiments, the bacteria of the genus *Bifidobacterium* comprise bacteria of the species *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, *Bifidobacterium angulatum*, *Bifidobacterium asteroides*, *Bifidobacterium boum*, *Bifidobacterium choerinum*, *Bifidobacterium coryneforme*, *Bifidobacterium cuniculi*, *Bifidobacterium denticol-* ens, *Bifidobacterium dentium, Bifidobacterium gallicum, Bifidobacterium gallinarum, Bifidobacterium indicum, Bifidobacterium inopinatum, Bifidobacterium magnum, Bifidobacterium merycicum, Bifidobacterium minimum, Bifidobacterium pseudolongum, Bifidobacterium pullorum, Bifidobacterium psychraerophilum, Bifidobacterium ruminantium, Bifidobacterium saeculare, Bifidobacterium scardovii, Bifidobacterium simiae, Bifidobacterium subtile, Bifidobacterium therammcidophilum, Bifidobacterium thermophilum, Bifidobacterium tsurumiense, Bifidobacterium urinalis* or *Bifidobacterium* sp. In some embodiments, the bacterial formulation is administered by oral administration or rectal administration. In some embodiments, the bacterial formulation is administered by oral administration. In some embodiments, the bacterial formulation is administered to the subject in two or more doses (e.g., 2, 3, 4, 5, 6, 7, 8, 9, 10, or more, or ranges therebetween). In some embodiments, methods further comprise administering to the subject an antibiotic before the bacterial formulation is administered to the subject. In some embodiments, methods further comprise administering to the subject an immune checkpoint inhibitor. In some embodiments, the immune checkpoint inhibitor is an antibody or antigen binding fragment thereof that binds to CTLA4, PD-1, PD-L1, PD-L2, A2AR, B7-H3, B7-H4, BTLA, KIR, LAG3, TIM-3 or VISTA. In some embodiments, the immune checkpoint inhibitor is an antibody or antigen binding fragment thereof that binds to PD-1 or PD-L1. In some embodiments, the immune checkpoint inhibitor is nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010.

BRIEF DESCRIPTION OF THE DRAWINGS

FIG. 1A-I. Differences in melanoma outgrowth and tumor-specific immune responses between C57BL/6 JAX and TAC mice are eliminated upon cohousing. (A) B16.SIY tumor growth kinetics in newly arrived JAX and TAC mice. (B) IFN-γ ELISPOT in tumor-bearing JAX and TAC mice 7 days following tumor inoculation. (C) Mean size of IFN-γ spots ($10^{-3}$ mm$^2$). (D) Flow cytometry of SIY$^+$T cells from total CD8$^+$T cells within the tumor of JAX and TAC mice as determined by flow cytometry 21 days post-tumor inoculation. (E) Percentage of SIY$^+$ T cells of total CD8$^°$ T cells within the tumor of JAX and TAC mice as determined by flow cytometry 21 days post-tumor inoculation. (F) B16.SIY tumor growth kinetics in JAX and TAC mice cohoused for 3 weeks prior to tumor inoculation. (G) Number of IFN-γ spots/$10^6$ splenocytes in tumor-bearing JAX and TAC mice cohoused for 3 weeks prior to tumor inoculation. (H) Mean size of IFN-γ spots ($10^{-3}$ mm$^2$). (I) Percentage of SIY$^+$ T cells of total CD8$^+$ T cells within the tumor of JAX and TAC mice cohoused for 3 weeks prior to tumor inoculation.

FIG. 5A-D. (A) Schematic of prophylactic fecal transfer: fecal pellets collected from JAX and TAC mice upon arrival in our facility were resuspended in PBS, homogenized and the supernatant was introduced by oral gavage into either JAX or TAC recipients as shown, once a week for two weeks prior to B16.SIY tumor inoculation. (B) B16.SIY tumor growth in JAX mice orally gavaged with TAC or JAX fecal material once weekly for two weeks prior to tumor implantation. (C) Percentage of SIY$^+$ T cells of total CD8$^+$ T cells within the tumor of groups as in FIG. 2A, determined by flow cytometry 7 days post-tumor inoculation. (D) Percentage of SIY$^+$ T cells of total CD8$^+$ T cells within the tumor of JAX and TAC mice, untreated or treated with αPD-L1 mAb, as determined by flow cytometry 21 days post-tumor inoculation.

FIG. 11A-E. (A) B16.SIY tumor growth kinetics in TAC mice, untreated or treated with ATCC derived *B. breve* or *B. longum*. (B) B16.F10 tumor growth kinetics in TAC mice, untreated or treated with *Bifidobacterium* 7 and 14 days post tumor implantation. (C) MB49 tumor growth kinetics in TAC mice, untreated or treated with *Bifidobacterium* 7 and 14 days post tumor implantation. (D) B16.SIY tumor growth kinetics in TAC mice, untreated or treated with *Lactobacillus murinus* or JAX fecal material 7 and 14 days post tumor implantation. (E) Percentage of tumor-infiltrating SIY$^+$ T cells of total CD8$^+$ T cells for treatment groups as in (D), determined by flow cytometry 18 days after start of treatment.

*Bifidobacterium*-treated TAC mice in the presence of different concentrations of SIY peptide as shown. (B) Percentage of 2C CD8+ T cells with undiluted CFSE, stimulated in vitro with DCs purified from naive TAC, JAX and *Bifidobacterium*-treated TAC mice in the presence of different concentrations of SIY peptide as shown.

Figure 15:
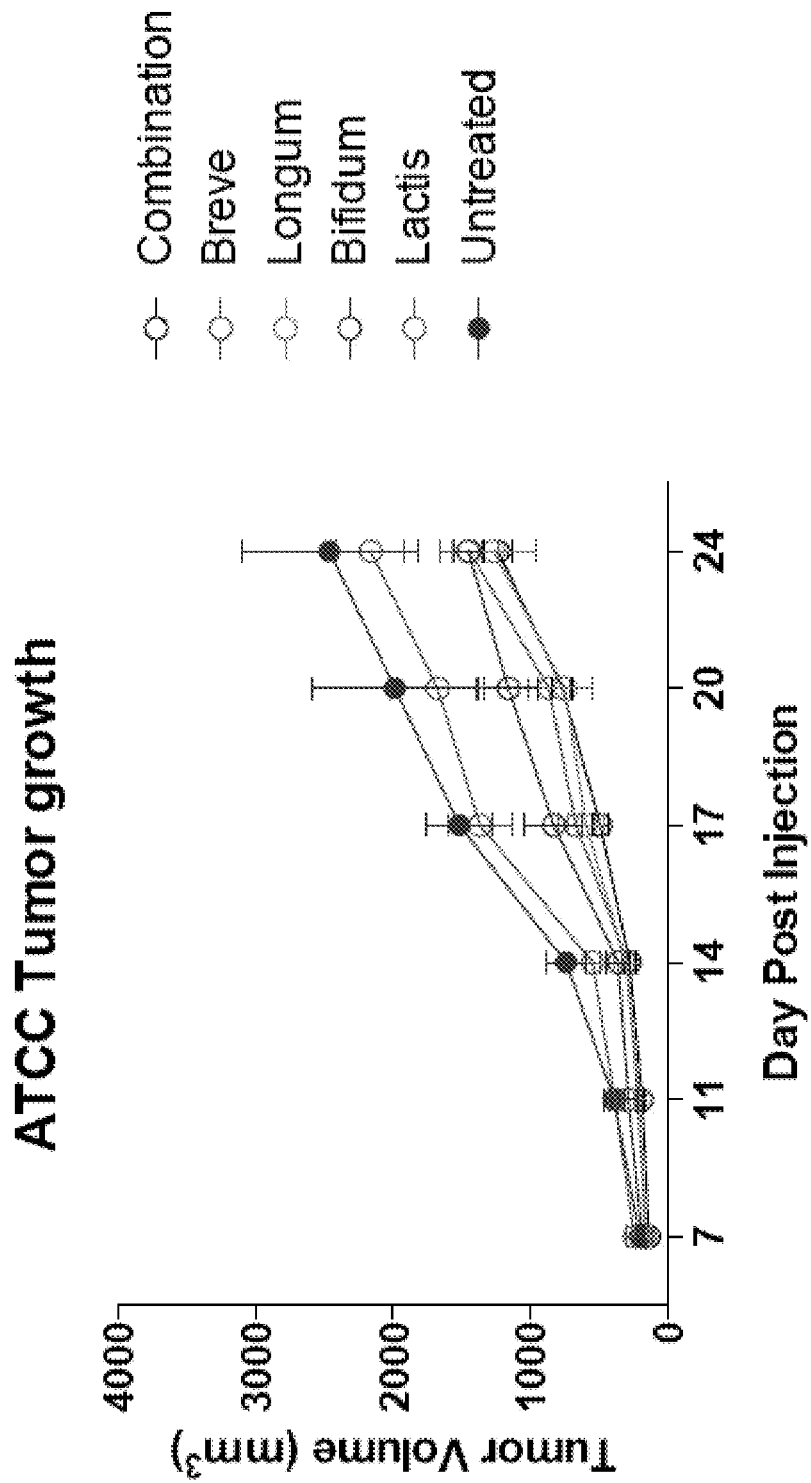

FIG. 15. B16.SIY tumor growth in TAC mice, untreated or treated individually with ATCC 15700 *B. breve*, ATCC BAA-999 *B. longum*, ATCC 27536 *B. Lactis* or ATCC 15696 *B. Bifidum*, or treated with all four strains combined.

DEFINITIONS

As used herein, the term "microbe" refers to cellular microorganisms including bacteria, fungi, and archaea, and encompasses both individual organisms and populations comprising any number of the organisms.

As used herein, the term "microflora" refers to an assemblage of microorganisms localized to a distinct environment. Microflora may include, for example, populations of various bacteria, fungi, and/or archaea that inhabit a particular environment. For example, "gut microflora," "vaginal microbiota," and "oral microflora" are an assemblage of one or more species of microorganisms that are localized to, or found in, the gut, vagina, or mouth, respectively. "Normal microflora" refers to a population of microorganisms that localize in a particular environment in a normal, non-pathological state (e.g., a sample of gut microflora from a subject without cancer). "Pathologic microflora" refers to a population of various microorganisms that localize in a particular environment in pathological state and differs from normal microflora in terms of identify, absolute amount, or relative amount of the various microbes.

As used herein, the term "commensal microbe" refers to a microorganism that is non-pathogenic to a host and is part of the normal microflora of the host.

As used herein, the term "co-administration" refers to the administration of at least two agents (e.g., commensal microflora and a cancer therapy) or therapies to a subject. In some embodiments, the co-administration of two or more agents/therapies is concurrent. In other embodiments, the co-administration of two or more agents/therapies is sequential (e.g., a first agent/therapy is administered prior to a second agent/therapy).

As used herein, the term "beneficial microbe" refers to a microbe (e.g., bacterium) strain or species that inhibits the growth of cancer/tumor cells and/or facilitates treatment of cancer/tumor cells (e.g., inhibits immune evasion). Beneficial microbes may function by, for example, creating an anti-cancer/anti-tumor environment, microenvironment and/or metabolome, and/or by creating an environment, microenvironment and/or metabolome that inhibits immune evasion or other mechanisms by which cancer cells resist therapy.

As used herein, the term "detrimental microbe" refers to a microbe (e.g., bacterium) strain or species that facilitates the growth of cancer/tumor cells and/or prevents or reduces the effectiveness of treatment of cancer/tumor cells (e.g., inhibits immune evasion). Detrimental microbes may function by, for example, creating an environment, microenvironment and/or metabolome that facilitates immune evasion or other mechanisms by which cancer cells resist therapy and/or enhance cancer/tumor growth.

As used herein, the term "pharmaceutical agent" refers to a compound, macromolecule, or other chemical/non-biological entity that is administered to a subject to elicit a desired biological response. A pharmaceutical agent may be a "drug" or another entity which is biologically active in a human being or other mammal, locally and/or systemically. Examples of drugs are disclosed in the Merck Index and the Physicians Desk Reference, the entire disclosures of which are incorporated by reference herein for all purposes.

As used herein, the terms "microbial agent," "commensal microbial agent," and "probiotic" refer to compositions comprising a microbe or population of multiple different microbes for administration to a subject.

As used herein, the term "antimicrobial agent" is used to describe a therapeutic compound or bioactive agent which treats a microbial infection, for example, an infection caused by a bacteria, virus, protozoa or fungus. The antimicrobial agent may be an antibiotic, an antifungal agent, an antiviral or an antiprotozoal or antiparasitic agent (which may also be used to treat multicellular parasites).

As used herein, the terms "antibiotic" and "antibacterial agent" refer to a chemical agent which is active against bacteria. In common usage, an antibiotic is a substance or compound (also called chemotherapeutic agent) that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymyxins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

As used herein, the term "antiviral agent" refers to a chemical agent which is used to treat a viral infection. Antiviral drugs are a class of medication used specifically for treating viral infections, specific antivirals are useful for treating infection by specific viruses. Antivirals typically only inhibit virus development.

As used herein, the term "antifungal agent" refers to a therapeutic compound or bioactive agent which may be used to treat a fungal infection in a patient. An antifungal drug is a medication used to treat fungal infections such as athlete's foot, ringworm, candidiasis (thrush), serious systemic infections such as cryptococcal meningitis, and related fungal infections. Antifungal agents include, for example, polyene antifungals, imidazole, triazole and thiazole antifungals, allylamines, echinocandins, griseofulvin, flycystosine, undecylenic acid, among others.

As used herein, the term "antiparasitic agent" refers to a therapeutic compound or bioactive agent that is used to treat parasitic diseases including nematodes, cestodes, trematodes, infectious protozoa, and amoebas. Exemplary antiparasitic agents include: antinematodes (e.g., mebendazole, pyrantel pamoate, thiabendazole, diethycarbazine), anticestodes (e.g., niclosamide, praziquantel), antitrematodes (e.g., praziquantel), antiamoebics (e.g., rifampin and amphotericin B), antiprotozoals (e.g., melarsoprol, eflornithine, metronidazole and tinidazole), among others.

As used herein, the term "pharmaceutical formulation" refers to at least one pharmaceutical agent and/or microbial agent in combination with one or more additional components that assist in rendering the agent(s) suitable for achieving the desired effect upon administration to a subject. The pharmaceutical formulation may include one or more additives, for example pharmaceutically acceptable excipients, carriers, penetration enhancers, coatings, stabilizers, buffers or other materials physically associated with the pharmaceutical/microbial agent to enhance the administration, release (e.g., timing of release), deliverability, bioavailability, effectiveness, etc. of the dosage form. The formulation may be, for example, a liquid, a suspension, a solid, a nanoparticle, emulsion, micelle, ointment, gel, emulsion, coating, etc. A pharmaceutical formulation may contain a single agent or multiple agents (e.g., microbial agent and pharmaceutical agent).

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition (e.g., cancer, solid tumor cancer, non-T cell-infiltrated tumor cancer, etc.).

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including Abs, cytokines, and complement) that results in selective targeting, binding to, damage to, destruction of, and/or elimination from a subject of invading pathogens, cells or tissues infected with pathogens, or cancerous or other abnormal cells.

As used herein, the term "immunoregulator" refers to an agent or a signaling pathway (or a component thereof) that regulates an immune response. "Regulating," "modifying" or "modulating" an immune response refers to any alteration of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in a cancer microenvironment.

As used herein, the term "immune evasion" refers to inhibition of a subject's immune system or a component thereof (e.g., endogenous T cell response) by a cancer or tumor cell in order to maximize or allow continued growth or spread of the cancer/tumor.

As used herein, the term "immunotherapy" refers to the treatment or prevention of a disease or condition (e.g., cancer) by a method comprising inducing, enhancing, suppressing or otherwise modifying an immune response.

As used herein, "potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "antibody" refers to a whole antibody molecule or a fragment thereof (e.g., fragments such as Fab, Fab', and F(ab')2), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VH, and three constant regions, CH1, CH2, and CH3. The VH domain is at the amino-terminus of the heavy chain, and the CH3 domain is at the carboxy-terminus. In a native antibody, a light chain comprises a variable region, VL, and a constant region, CL. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant (Ka) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')2, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the CH1 and variable region of one heavy chain. The heavy chain of a Fab molecule cannot form a disulfide bond with another heavy chain molecule. A "Fab'" fragment comprises one light chain and one heavy chain that comprises additional constant region, extending between the CH1 and CH2 domains. An interchain disulfide bond can be formed between two heavy chains of a Fab' fragment to form a "F(ab')2" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "effective dose" or "effective amount" refers to an amount of an agent, e.g., an antibody, that results in the reduction of symptoms in a patient or results in a desired biological outcome. In certain embodiments, an effective dose or effective amount is sufficient to treat or reduce symptoms of a disease or condition.

DETAILED DESCRIPTION

Provided herein are methods of treatment and/or prevention of cancer by manipulation of commensal microflora. In particular, the amount, identity, presence, and/or ratio of microflora (e.g., gut microflora) in a subject is manipulated to facilitate one or more co-treatments.

T cell infiltration of solid tumors is associated with favorable patient outcomes, yet the mechanisms underlying variable endogenous immune responses between individuals are not well understood. Experiments were conducted during development of embodiments described herein to examine potential effects of microbial composition on spontaneous anti-tumor immunity. B16 melanoma growth was compared in C57BL/6 mice having distinct commensal microbiota. The two populations of mice showed robust versus weak spontaneous anti-tumor immunity. This phenotypic difference was eliminated upon cohousing or following fecal transfer. 16S rRNA sequencing identified *Bifidobacterium* as associated with the anti-tumor effects. Oral administration of *Bifidobacterium* alone or in combination with systemic αPD-L1 in tumor-bearing mice markedly improved tumor control in a $CD8^+$ T cell-dependent manner. Mechanistically, the effect was mediated by augmented dendritic cell function leading to more robust antigen-specific $CD8^+$ T cell priming and markedly increased accumulation of activated T cells in the tumor microenvironment. These data, for example, demonstrate advantages manipulating commensal microbes as a cancer therapeutic.

In some embodiments, the effectiveness of an endogenous immune response, immunotherapy, chemotherapeutic, or other treatment (e.g., surgery, radiation, etc.) in the treatment or prevention of reoccurrence of cancer and/or tumor is dependent upon conditions within the subject (e.g., the tumor microenvironment). In particular, the identity or characteristics (e.g., concentration or level) of the microflora within a subject affects the effectiveness of cancer treatments (e.g., generally or specific treatments) and/or the effectiveness of the subject's own immune response to cancer.

In some embodiments, the presence or increased level of one or more microbes (e.g., one or more types of bacteria) in a subject potentiates cancer/tumor growth, spread (e.g., malignancy), and/or evasion of treatment/immune response. In some embodiments, the presence or increased level of one or more microbes (e.g., one or more types of bacteria) in a subject inhibits treatment (e.g., immunotherapy, chemotherapy, etc.) and/or the subject's endogenous immune response to cancer and/or tumor cells. In some embodiments, the absence and/or decreased level of one or more microbes (e.g., one or more types of bacteria) in a subject potentiates cancer/tumor growth, spread, and/or evasion of treatment/immune response. In some embodiments, the absence or decreased level of one or more microbes (e.g., one or more types of bacteria) in a subject inhibits treatment (e.g., immunotherapy, chemotherapy, etc.) and/or the subject's endogenous immune response to cancer and/or tumor cells.

In some embodiments, the presence or increased level of one or more microbes (e.g., one or more types of bacteria) in a subject discourages cancer/tumor growth, spread, and/or evasion of treatment/immune response. In some embodiments, the presence or increased level of one or more microbes (e.g., one or more types of bacteria) in a subject facilitates treatment (e.g., immunotherapy, chemotherapy, etc.) and/or the subject's endogenous immune response to cancer and/or tumor cells. In some embodiments, the absence and/or decreased level of one or more microbes (e.g., one or more types of bacteria) in a subject discourages cancer/tumor growth, spread, and/or evasion of treatment/immune response. In some embodiments, the absence or decreased level of one or more microbes (e.g., one or more types of bacteria) in a subject facilitates treatment (e.g., immunotherapy, chemotherapy, etc.) and/or the subject's endogenous immune response to cancer and/or tumor cells.

In some embodiments, the presence of beneficial microbes (e.g., microbes that facilitate cancer treatment) in a subject creates an environment or microenvironment (e.g., metabolome) that is conducive to the treatment of cancer and/or inhibits cancer/tumor growth. In some embodiments, the presence of detrimental microbes (e.g., microbes that facilitate cancer/tumor growth and/or prevent treatment) in a subject creates an environment or microenvironment (e.g., metabolome) that is conducive to the treatment of cancer and/or inhibits cancer/tumor growth.

Experiments conducted during development of embodiments described herein demonstrate that modulation of levels and/or identity of the microflora in a subject facilitates treatment of cancer/tumor within the subject, enhances the endogenous immune response, decreases immune evasion or other inhibitory mechanisms to treatment of endogenous immune response, and/or improves cancer outcomes for the subject. Modulation of microflora levels and/or identity may comprise encouraging or facilitating growth of one or more types of beneficial microbes (e.g., microbes that facilitate cancer treatment), discouraging or inhibiting growth of one or more types of detrimental microbes (e.g., microbes that facilitate cancer/tumor growth and/or prevent treatment), administering one or more types of beneficial microbes (e.g., microbes that facilitate cancer treatment) to the subject, and/or combinations thereof. Embodiments within the scope herein are not limited by the mechanisms for introducing one or more microbes (e.g., fecal transplant, probiotic administration, etc.), encouraging growth of beneficial microbes (e.g., administering agents that skew the environment within the subject toward growth conditions for the beneficial microbes), discouraging or inhibiting growth of detrimental microbes (e.g., administering agents that skew the environment within the subject away from growth conditions for the detrimental microbes, administration of antimicrobial(s), etc.), and combinations thereof.

In some embodiments, methods are provided for the treatment or prevention of cancer by the manipulation of the presence, amount, or relative ratio of commensal microflora (e.g., gut microflora). In some embodiments, the presence, amount, or relative ratio of particular bacteria, fungi, and/or archaea within a subject is manipulated. For example, in some embodiments, the presence, amount, or relative ratio of one or more bacteria from the phyla Firmicutes, Bacteroidetes, Actinobacteria, and/or Proteobacteria are manipulated. In some embodiments, the presence, amount, or relative ratio of one or more bacteria belonging to the genera *Bacteroides, Clostridium, Fusobacterium, Eubacterium, Ruminococcus, Peptococcus, Peptostreptococcus, Bifidobacterium, Rikenella, Alistipes, Marinilabilia, Anaerostipes, Escherichia,* and/or *Lactobacillus* are manipulated. In some embodiments, the presence, amount, or relative ratio of one or more fungi belonging to the genus *Candida, Saccharomyces, Aspergillus,* and/or *Penicillium* are manipulated.

In some embodiments, the presence and/or levels of one or more commensal microbes are manipulated in a subject suffering from cancer, at heightened risk of cancer, and/or receiving treatment for cancer. Exemplary commensal microbes include *Lactococcus* (e.g., *Lactococcus cremoris* and *Lactococcus lactis*), *Lactobacillus* (e.g., *Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbrueckii, Lactobacillus plantarum, Lactobacillus paraplantarum, Lactobacillus crispatus, Lactobacillus gasseri, Lactobacillus johnsonii* and *Lactobacillus jensenii*), *Leuconostoc, Carnobacterium, Enterococcus, Propionibacteium, Pediococcus, Bifidobacterium* (e.g., *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis, Bifidobacterium angulatum,* etc.), *Streptococcus* (e.g., *Streptococcus thermophiles, Streptococcus salivarius, Streptococcus oralis, Streptococcus uberis, Streptococcus rattus,* etc.); *Escherichia coli, Bacillus coagulans, Bacillus lansii,* Yeast (e.g., *Saccharomyces cerevisiae, Saccharomyces boulardii,* etc.); and combinations thereof.

In some embodiments, one or more species, genera, and/or types of microbes are administered and/or the growth thereof is facilitated. In some embodiments, the growth of one or more species, genera, and/or types of microbes is inhibited. In some embodiments, one or more species, genera, and/or types of microbes are administered and/or the growth thereof is facilitated; and the growth of one or more other species, genera, and/or types of microbes is inhibited.

In some embodiments, the level or presence of one or more beneficial microbes (e.g., microbes that inhibit cancer/tumor growth or spread, enhance cancer/tumor treatment, etc.) is modulated by the administration of such microbes to a subject.

In some embodiments, microflora-modulation utilizes prepared probiotic compositions for administration to/by a subject. Probiotic compositions comprise one or more beneficial microbes (e.g., bacteria) formulated such that administration of the probiotic (e.g., orally, rectally, by inhalation, etc.) results in population of the subject by the beneficial microbes.

In some embodiments, probiotic compositions comprise cultured microbes that are combined and/or formulated for administration to a subject. In some embodiments, probiotics contain microbes of known genera, species, etc. and/or at known concentrations (cfus). Probiotic compositions may be in the form of a pharmaceutical-type composition (e.g., capsule, tables, liquid, aerosol, etc.) or in the form of a food supplement.

In some embodiments, probiotic microbes (e.g., bacteria) are formulated in a pharmaceutically acceptable composition for delivery to a subject. In some embodiments, probiotics are formulated with a pharmaceutically acceptable carrier suitable for a solid or semi-solid formulation. In some embodiments, probiotic microbes are formulated with a pharmaceutically acceptable carrier suitable for a liquid or gel formulation. Probiotic formulations may be formulated for enteral delivery, e.g., oral delivery, or delivery as a suppository, but can also be formulated for parenteral delivery, e.g., vaginal delivery, inhalational delivery (e.g., oral delivery, nasal delivery, and intrapulmonary delivery), and the like.

The probiotic compositions that find use in embodiments described herein may be formulated in a wide variety of oral administration dosage forms, with one or more pharmaceutically acceptable carriers. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the probiotic microbes. In tablets, the microbes are mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Other forms suitable for oral administration include liquid form preparations such as emulsions, syrups, elixirs, aqueous solutions, aqueous suspensions, or solid form preparations which are intended to be converted shortly before use to liquid form preparations. Aqueous suspensions can be prepared by dispersing the probiotic microbes in water with viscous material, such as natural or synthetic gums, resins, methylcellulose, sodium carboxymethylcellulose, and other well-known suspending agents.

The probiotic compositions (e.g., microbes (e.g., bacteria)) may be formulated for administration as suppositories. A low melting wax, such as a mixture of fatty acid glycerides or cocoa butter is first melted and the probiotic microbes are dispersed homogeneously, for example, by stirring. The molten homogeneous mixture is then poured into conveniently sized molds, allowed to cool, and to solidify.

The probiotic compositions (e.g., microbes (e.g., bacteria)) may be formulated for vaginal administration. Pessaries, tampons, creams, gels, pastes, foams or sprays, may contain agents in addition to the bacteria, such carriers, known in the art to be appropriate.

In some embodiments, probiotic compositions (e.g., microbes (e.g., bacteria)) may be formulated for delivery by inhalation. As used herein, the term "aerosol" is used in its conventional sense as referring to very fine liquid or solid particles carries by a propellant gas under pressure to a site of therapeutic application. The term "liquid formulation for delivery to respiratory tissue" and the like, as used herein, describe compositions comprising probiotic microbes with a pharmaceutically acceptable carrier in flowable liquid form. Such formulations, when used for delivery to a respiratory tissue, are generally solutions, e.g. aqueous solutions, ethanolic solutions, aqueous/ethanolic solutions, saline solutions and colloidal suspensions.

Rather than pharmaceutical-type formulation, probiotic compositions may be formulated as food additive and/or food product and incorporated into a variety of foods and beverages. Suitable foods and beverages include, but are not limited to, yogurts, ice creams, cheeses, baked products such as bread, biscuits and cakes, dairy and dairy substitute foods, soy-based food products, grain-based food products, starch-based food products, confectionery products, edible oil compositions, spreads, breakfast cereals, infant formulas, juices, power drinks, and the like.

In some embodiments, a probiotic composition is administered over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of the probiotic composition administered for the dosing time period is concentration of from about 10 to about $1\times10^{14}$ colony forming units (cfu) of the commensal microbial agent(s) (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1\times10^4$ to about $1\times10^{11}$ cfu, about $1\times10^6$ to about $1\times10^9$ cfu, about $1\times10^{10}$ to about $1\times10^{12}$ cf, etc.), etc.).

In some embodiments, the microbial make-up of a probiotic composition consists or consists essentially of one or more beneficial microbes (e.g., bacteria). In some embodiments, the microbial make-up of a probiotic composition consists or consists essentially of 1, 2, 3, 4, 5, 6, 7, 8, 9, 10, 15, 20, 25, 30, 40, 50, 60, 70, 80, 90, 100, or any ranges therein (e.g., 1-4, 5-10, 8-20, etc.) strains and/or species of microbes. In some embodiments, fewer than 50 microbial strains (e.g., 1, 2, 3, 4, 5, 6, 7, 8, 9, 10, 15, 20, 25, 30, 40, 50, or any ranges therein (e.g., 1-4, 5-10, 8-20, etc.) are at least 50% (e.g., 50%, 60%, 70%, 80%, 85%, 90%, 91%, 92%, 93%, 94%, 95%, 96%, 97%, 98%, 99%, 99.5%, 99.9%, 99.99%) of the microbial population (e.g., by mass, by cfu, etc.) of a probiotic composition. For example, in some embodiments, a single species or strain of *Bifidobacterium* is at least 95% of the microbial population, as measured by colony forming units, of a particular probiotic composition. As another example, in some embodiments, a single species or strain of *Bifidobacterium* is at least 40% and bacteria from the genus *Lactobacillus* are at least 50% of the microbial population, as measured by mass, of a particular probiotic composition. These examples are not limiting.

In some embodiments, microflora in a subject (e.g., a subject suffering from cancer, a subject with microflora that promotes cancer growth, a subject with microflora that promotes evasion of cancer treatment (e.g., by immunotherapy), etc.) are modulated by transplantation of microbiota from a subject with favorable characteristics (e.g., a subject without cancer, a subject with microflora that inhibits cancer growth, a subject with microflora that promotes treatment of cancer (e.g., by immunotherapy), etc.) into the recipient subject.

In some embodiments, donor microflora are obtained sampling microflora from the desired region of the donor subject body (e.g., colon, oral cavity, vagina, etc.). In particular embodiments, fecal material (e.g., 100 g-500 g) is obtained from a donor. The material may be administered to a recipient subject with or without subsequent preparation steps (e.g., diluting, mixing, oxygenating, filtering, supplementing (e.g., with prebiotics, with growth media, etc.), testing (e.g., for pathogens or detrimental microbes), etc.). The donor microflora (e.g., fecal material) may be administered without preservation (e.g., administered within 12 hours (e.g., <6 hours, <4 hours, <2 hours, <1 hour, etc.)) or may be preserved (e.g., frozen, freeze dried, etc.), for example, to allow for delay (e.g., 1 day, 2, days, 1 week, 1 month, or more) before delivery to the subject.

In some embodiments, donor microflora are proceed to remove one or more components. For example, parasitic of detrimental microbes may be removed or killed. Contaminants within the donor sample may be removed. In some embodiments, donor microflora is enriched for one or more specific microbes (e.g., 2-fold, 3-fold, 4 fold, 10-fold, 20-fold, or more enrichment). In some embodiments, donor microflora is enriched such that at least 1% of the microbes in the population are the desired beneficial microbes (e.g., 1%, 2%, 3%, 4%, 5%, 6%, 7%, 8%, 9%, 10%, 15%, 20%, 25%, 30%, 40%, 50%, 60%, 70%, 80%, 90%, or more). In some embodiments, donor microflora are doped with one or more cultured beneficial microbes.

In particular embodiments, transplanted microflora may be administered to the recipient subject by any suitable delivery mechanism, including but not limited to enema, colonoscope, nasogastric or nasoduodenal tube, lavage or irrigation, or orally (e.g., in the form of a capsule).

In some embodiments, a commensal microbial agent or population of microbial agents is administered (e.g., via probiotic composition or microflora transplant) over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of commensal microbial agent(s) administered for the dosing time period is concentration of from about 10 to about $1 \times 10^{14}$ colony forming units (cfu) of the commensal microbial agent(s) (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.).

The dose can be administered in a single unit dose administered at any time during a day. Alternatively the loading dose can be administered in two or more doses administered at a single time of day or at two or more separate times of day.

Over the course of multiple dosing periods, the dose can be tapered from an initial dose to a higher dose (or increased from an initial dose to a higher dose), on predetermined timing or by the when the subject and/or clinician based on the results of the treatment. The appropriate dosage amount will vary by, for example, an individual subject's age, weight, condition or disease, severity of disease, etc.

By way of non-limiting example (both in terms of identify of the microbe as well as dose), in some embodiments, one or more strains of *Bifidobacterium* are administered via 3 capsules daily, each capsule containing $1 \times 10^9$ cfu of *Bifidobacterium*. Alternatively, in other embodiments one or more strains of *Bifidobacterium* are administered at a dosage of one capsule daily containing $1 \times 10^{12}$ cfu of bacteria. Any other dosages (e.g., cfu), doses (e.g., times per day, week, etc.), and identity of the microbe(s) (e.g., within the ranges described herein) are within the scope herein.

In some embodiments, microbes for probiotic compositions are obtained from culture. In some embodiments, strains of beneficial microbes are genetically engineered to enhance one or more of production (e.g., at scale), formulation, delivery, or the biological effect of the microbe. In some embodiments, microbes are engineered to express a detectable marker that allows tracking of the microbes within a subject, or confirmation that the microbe has integrated into a subjects microflora. In some embodiments, microbes are engineered to express a cancer therapeutic (e.g., chemotherapeutic, immunotherapeutic, antibodies, etc.), anti-inflammatory agent, of other drug.

In some embodiments, one or more prebiotics are administered to a subject as an independent treatment (e.g., to increase the level of a beneficial microbe) or in conjunction with other treatments described herein. Prebiotics are agents that increase the in vivo growth rate or activity of commensal microbes, such as *Lactobacillus* and/or *Bifidobacterium*. In some embodiments, prebiotics are soluble fiber sources. In some embodiments, when prebiotics are administered (e.g., fed) to a subject they are not digested or are not fully digested by the subject's digestive enzymes, but rather support the intestinal health of the subject and provide an energy source for the beneficial microbes and enhance the growth thereof. Prebiotics include, for example, naturally occurring lecithins and/or oleic acid, and are described, for example in U.S. Pat. No. 8,449,878 which is herein incorporated by reference in its entirety.

In some embodiments, the level or presence of one or more detrimental microbes (e.g., microbes that facilitate cancer/tumor growth or spread, inhibit cancer/tumor treatment, etc.) is modulated, for example, by the administration of one or more antimicrobial agents to a subject or modulation of conditions within the subject to disfavor growth of the detrimental microbes. In some embodiments, antimicrobial agents are administered.

In some embodiments, the antimicrobial agent is an antibiotic. Exemplary antibiotics that may find use in some embodiments include, but are not limited to: amikacin, gentamicin, kanamycin, neomycin, netilmicin, streptomycin, tobramycin, paromycin, geldanamycin, herbimycin, loracarbef, ertapenem, doripenem, imipenem, meropenem, cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobirprole, vancomycin, azithromycin, clarithromycin, dirithromycin, erythromycin, roxithromycin, troleandomycin, telithromycin, spectinomycin, aztreonam, amoxicillin, ampicillin, azociling, carbenicillin, cloxacillin, dicloxacillin, flucloxacillin, mezlocillin, meticillin, nafcillin, oxacillin, peperacillin, ticarcillin, bacitracin, colistin, polymyxin B, ciprofloxacin, clavulanic acid, enoxacin, gatifloxacin, levofloxacin, lomefloxacin, moxifloxacin, nonfloxacin, ofloxacin, trovafloxacin, grepafloxacin, sparfloxacin, AL-15469A, AL-38905, OP-145, afenide, prontosil, sulfacetamide, sulfamethiazole, sulfanamide, sulfasalazine, sulfisoxazole, trimethoprim, cotrimoxazole, demeclocycline, doxycycline, minocycline, oxytetracycline, tetrayycline, linezolid, arsogebanubem chloramphenicol, clindamycin, lincomycin, ethambutol, fosfomycin, fusidic acid, furazolidone, isoniazid, linezolid, metronidazole, mupirocin, nitrofurantoin, rifampicin, thamphenicol, tinidazole, amoxicillin+clavulanic acid, Maximin H5, Dermcidin, Cecropins, andropin, moricin, ceratotoxin, melittin, Magainin, dermaseptin, bombinin, brevinin-1, esculentins and buforin II, CAP 18, LL37, abaecin, apidaecins, prophenin, indolicidin, brevinins, protegrin, tachyplesins, defensins, drosomycin, alamethicin, pexiganan or MSI-78, MSI-843, MSI-594, polyphemusin, colicin, pyocin, klebicin, subtilin, epidermin, herbicolacin, brevicin, halocin, agrocin, alveicin, carnocin, curvaticin, divercin, enterocin, enterolysin, erwiniocin, glycinecin, lactococin, lacticin, leucoccin, mesentericin, pediocin, plantaricin, sakacin, sulfolobicin, vibriocin, warnerinand, nisin, or a salt or cocrystal, or prodrug or solvate thereof, or a combination thereof.

In some embodiments, the antimicrobial is an antifungal agent. Exemplary antifungals that may find use in some embodiments include, but are not limited to: amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

In some embodiments, the antimicrobial is an antiparasitic. Exemplary antiparasitics that may find use in some embodiments include, but are not limited to: amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, methods and compositions for reduction of detrimental microbe levels are co-administered (e.g., serially, concurrently, etc.) with methods and compositions for increasing beneficial microbe levels. In some embodiments, by reducing overall microbe levels or by reducing the levels of specific microbes (e.g., detrimental microbes, high population microbes, etc.), the population of beneficial microbes can more effectively be modulated (e.g., increased).

In some embodiments, in order to develop a microflora population within a subject that facilitates cancer treatment or inhibits cancer growth/spread, antimicrobial agents are first administered to eliminate or reduce the microflora within the subject, and then the microflora population is reestablished using the methods and compositions described herein (e.g., administration of beneficial microbes). In some embodiments, antimicrobials (e.g., antibiotics) that reduce the microbe (e.g., bacteria) population generally are employed. In some embodiments, antimicrobials that target detrimental microbes preferentially are employed.

In some embodiments, modulating the microflora composition is sufficient on its own to allow the endogenous immune system of a subject to respond to the presence of cancer cells and or tumor growth. However, in other embodiments, microflora composition is manipulated along with one or more other cancer therapies. In some embodiments, manipulation of the microflora composition (e.g., identity and/or level) treats cancer by a mechanism independent of one or more additional cancer treatments. In other embodiments, modulation of microflora composition facilitates (e.g., increases the effectiveness of) the cancer treatment. In some embodiments, one or more cancer treatments enhance the effectiveness of the modulation of microflora composition. Embodiments herein are not limited by the types of cancer treatments (e.g., surgery, radiation, immunotherapy, chemotherapeutic, etc.) unless specifically noted.

In some embodiments, immunotherapeutic cancer treatment encompasses blockade of immune-inhibitory receptors, for example using monoclonal antibodies (mAbs) against CTLA-4 and PD-1/PD-L1 (Wolchok, J. D. et al. The New England Journal of Medicine 369, 122-133 (2013); Topalian, S. L. et al. Journal of clinical oncology 32, 1020-1030 (2014); Topalian, S. L. et al. The New England journal of medicine 366, 2443-2454 (2012); Hodi, F. S. et al. The New England journal of medicine 363, 711-723 (2010); herein incorporated by reference in their entireties).

In some embodiments, the immunotherapy includes the administration of an immune checkpoint inhibitor. Immune Checkpoint inhibition broadly refers to inhibiting the checkpoints that cancer cells can produce to prevent or down-regulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010. In some embodiments, the immune checkpoint inhibitor may be administered via injection (e.g., intravenously, intratumorally, subcutaneously, or into lymph nodes), but may also be administered orally, topically, or via aerosol.

In some embodiments, the compositions for and/or methods of modulating microflora in a subject overcome immune invasion of cancer cells, tumor, tumor microenvironment, etc. In some embodiments, one or more additional cancer immunotherapies are employed (e.g., concurrently or serially) to make use of the induced immune-responsiveness treated cells/tumor. Suitable immunotherapies may include, but are not limited to: cell-based therapies (e.g., dendritic cell or T cell therapy, etc.), monoclonal antibody (mAb) therapy (e.g., naked mAbs, conjugated mAbs), cytokine therapy (e.g., interferons, interleukins, etc.), adjuvant treatment (e.g., polysaccharide-K), etc.

Examples of antibodies that may find use in the compositions and methods disclosed herein, particularly for use in immunotherapies (but not so limited) include, but are not limited, to antibodies such as trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgGI Fc); AMG386 (angiopoietin-1 and -2 binding peptide fused to IgGI Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb): Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@(17-1A)) (chimeric murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym). Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals—Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab, or ImmuRAIT-CEA.

In some embodiments, an immunotherapy, utilized as a co-therapy with the microflora modulation described herein, directly or indirectly targets one of more of: a regulatory T cell, myeloid suppressor cell, or dendritic cell. In another aspect, an immunotherapy specifically targets one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In some embodiments, the immunotherapy acts as an agonist that increases the function of the targeted molecule. In other embodiments, the immunotherapy is an antagonist that inhibits the function of the targeted molecule.

In some embodiments, an immunotherapy, utilized as a co-therapy with the microflora modulation described herein, directly or indirectly targets one of more of a specific cytokine, cytokine receptor, co-stimulatory molecule, co-inhibitory molecule, or immunomodulatory receptor that modulates the immune system. In another aspect, one of the following molecules are targeted by co-treatment with microflora modulation: tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand I (PD-L1: B7-H1); or PD-1 ligand 2 (PD-L2; B7-DC); B7 family; B7-1 (CD80); B7-2 (CD86); B7-H3; B7-H4; GITR/AITR: GITRL/AITRL; BTLA; CD70; CD27; LIGHT; HVEM: Toll-like receptor (TLR) (TLR 1, 2, 3, 4, 5, 6, 7, 8, 9, 10).

In some embodiments, the compositions for and/or methods of modulating microflora in a subject sensitize the cancer cells and/or tumor to treatment by one or more chemotherapeutic agents. In some embodiments, one or more chemotherapies are employed in addition to microflora modulation (e.g., concurrently or serially) to make use of the induced chemotherapeutic sensitivity. In other embodiments, one or more chemotherapeutics are provided as co-therapies with microflora modulation, with or without (known) synergism between the microflora modulation and the chemotherapy.

In some embodiments, exemplary anticancer agents suitable for use in compositions and methods described herein (e.g., co-administered with a β-catenin inhibitor) include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, compositions and methods herein comprise multiple modes for the treatment and/or prevention of cancer. In some embodiments, beneficial microbes are provided/administered (e.g., by a probiotic composition, fecal transplant, etc.) with prebiotics and/or other agents that facilitate the growth of the beneficial microbes. In some embodiments, beneficial microbes are provided/administered (e.g., by a probiotic composition, fecal transplant, etc.) with antimicrobial(s) (e.g., antibiotics) directed to kill or inhibit the growth of detrimental microbes. In some embodiments, prebiotics and/or other agents that facilitate the growth of the beneficial microbes are provided/administered with antimicrobial(s) (e.g., antibiotics) directed to kill or inhibit the growth of detrimental microbes. In some embodiments, beneficial microbes, prebiotics and/or other agents that facilitate the growth of the beneficial microbes, and an antimicrobial(s) (e.g., antibiotics) directed to kill or inhibit the growth of detrimental microbes are all co-administered.

In some embodiments, the co-administered agents are formulated into a single dose and/or composition. In some embodiments, the co-administered agents are in separate doses and/or compositions. In some embodiments in which separate doses and/or compositions are administered, the doses and/or compositions are administered simultaneously, consecutively, or spaced over a time span (e.g., <30 minutes, 1 hour, 2 hours, 4 hours, 6 hours, 12 hours, 1 day, 2 days, 3 days, 4 days, 5 days, 6 days, 1 week, or more, or any suitable ranges therebetween).

In some embodiments, beneficial microbes, prebiotics and/or other agents that facilitate the growth of the beneficial microbes, antimicrobial(s) (e.g., antibiotics) directed to kill or inhibit the growth of detrimental microbes, or any of the above mentioned combinations thereof are administered with a treatment for cancer. In embodiments, in which the modulation of microflora itself provides treatment for cancer, suitable co-treatments include immunotherapy, chemotherapy, surgery (e.g., tumor removal), radiation, etc. In other embodiments, in which the modulation of microflora sensitizes a subject or the tumor microenvironment to a particular cancer therapy (e.g., an immunotherapy, a chemotherapy, etc.), the particular cancer therapy is administered (e.g., optionally in addition to one or more other cancer therapies to which the subject is not directly sensitized to by the modulation).

In some embodiments, microflora modulation is provided as a co-therapy (e.g., chemotherapy, immunotherapy, etc.) with one or more additional therapies that target and/or bind to specific cancer or tumor cell markers. Such markers may be selected from the group including but not limited to, epidermal growth factor receptor (EGFR, EGFR1, ErbB-1, HER1). ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), 1L-6 receptor, interleukin-4, IL-4 receptor, Cytokine receptors, Class I (hematopoietin family) and Class II (interferon/1L-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT12, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGAT5), HERV-K MEL, KK-LC, KM-HN-1, LAGE, LAGE-1, CTL-recognized antigen on melanoma (CAMEL), MAGE-A1 (MAGE-1). MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikrein 4, mammaglobin-A, OA1, prostate specific antigen (PSA), prostate specific membrane antigen, TRP-1/, 75. TRP-2 adipophilin, interferon inducible protein absent in melanoma 2 (AIM-2). BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, PRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), etc.

Non-limiting examples of cancers that may be treated with the compositions and methods described herein include, but are not limited to: cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the cancer is a melanoma (e.g., metastatic malignant melanoma), renal cancer (e.g. clear cell carcinoma), prostate cancer (e.g. hormone refractory prostate adenocarcinoma), pancreatic cancer (e.g., adenocarcinoma), breast cancer, colon cancer, gallbladder cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, the cancer is a solid tumor cancer.

In some embodiments, the methods provided herein relate to the treatment and/or prevention of a leukemia. The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia.

In some embodiments, the methods provided herein relate to the treatment and/or prevention of a carcinoma. The term "carcinoma" refers to a malignant growth made up of epithelial cells tending to infiltrate the surrounding tissues, and/or resist physiological and non-physiological cell death signals and gives rise to metastases. Non-limiting exemplary types of carcinomas include, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti.

In some embodiments, the methods provided herein relate to the treatment and/or prevention of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated and/or prevented using the methods described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some embodiments, the cancer treated and/or prevented is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated and/or prevented using methods described herein include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leiomyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocytoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

Cancers prevented and/or treated in certain embodiments also include precancerous lesions, e.g. actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) elastosis and cervical dysplasia.

Cancers prevented and/or treated in some embodiments include non-cancerous or benign tumors, e.g. of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

Some embodiments described herein are particularly useful for the treatment of tumors that do not otherwise respond to immunotherapeutic approaches. In some embodiments, such tumors are non-responsive (or have a reduced response) to T cells (e.g., prevent infiltration of one or more T cell types (e.g., CD8$^+$ T cells) or antigen presenting cells (e.g., dendritic cells (e.g., CD103$^+$DCs, etc.), etc.). In some embodiments, compositions and methods described herein find use in the treatment of cancers in which T cells are not appropriately primed against tumor-associated antigens.

In some embodiments, methods are provided for testing sample (e.g., cell, tissue, population of cells, tumor, blood, urine, saliva, etc.) from a subject for one or more biomarkers of cancer, immune evasion, cancer promoting microenvironment, malignancy-promoting microenvironment, etc. Such biomarkers may comprise nucleic acids, small molecules, proteins, peptides, etc., and may be detected using any suitable assay of technique. In some embodiments, provided herein are DNA-, RNA-, small molecule, and/or protein-based diagnostic methods that either directly or indirectly detect the biomarkers of the evasion of immune response or immunotherapy by cancer cells or tumors. The present invention also provides compositions, reagents, and kits for such diagnostic purposes.

In some embodiments, biomarkers are detected at the nucleic acid (e.g., RNA) level. For example, the presence or amount of biomarker nucleic acid (e.g., mRNA) in a sample is determined (e.g., to determine the presence or level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, nucleic acid amplification (e.g., by PCR, RT-PCR, qPCR, etc.), microarray, Southern and Northern blotting, sequencing, etc. Non-amplified or amplified nucleic acids can be detected by any conventional means. For example, in some embodiments, nucleic acids are detected by hybridization with a detectably labeled probe and measurement of the resulting hybrids. Nucleic acid detection reagents may be labeled (e.g., fluorescently) or unlabeled, and may by free in solution or immobilized (e.g., on a bead, well, surface, chip, etc.).

In some embodiments, biomarkers are detected at the protein level. For example, the presence or amount of biomarker protein in a sample is determined (e.g., to determine the presence or level of biomarker expression or localization). In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized (e.g., on a bead, well, surface, chip, etc.).

In some embodiments, kits are provided comprising, for example, the probiotic or microflora transplant compositions described herein. Kits may further comprise instructions, cancer treatments, other probiotics, agents to enhance integration of microbes into the subject's microflora, etc.

EXPERIMENTAL

Example 1

Materials and Methods

Animals and Tumor Model:

C57BL/6 mice were obtained from Jackson laboratory or Taconic farms. 6-8-week-old female mice were used. The C57BL/6-derived melanoma cell line B16.F10.SIY (referred to herein as B16.SIY) was generated (Blank et al. Cancer research 64, 1140-1145 (2004); herein incorporated by reference in its entirety). For tumor growth experiments, mice were injected subcutaneously with $1\times10^6$ B16.SIY tumor cells. Tumor size was measured twice a week until endpoint and tumor volume was determined as length×width$^2$×0.5. For B16 parental tumor model experiments, mice were injected subcutaneously with $1\times10^6$ B16.F10 tumor cells. For bladder cancer model experiments, mice were injected subcutaneously with $2\times10^6$ MB49 cells. All experimental animal procedures were approved by the University of Chicago Animal Care and Use Committee (IACUC).

IFN-γ ELISPOT and SIY Pentamer Analyses:

Elispot plates (Millipore, MAIP S4510) were coated with purified αIFN-γ (BD) overnight at 4° C. Plates were blocked with 10% FBS in DMEM for 2 hours at room temperature. Whole splenocytes were plated at $10^6$ cells per well and stimulated with SIY peptide overnight at 37° C. Spots were developed using the BD mouse IFN-γ kit (Cat. No. 552569), and the number of spots was measured using an Immunospot Series 3 Analyzer and analyzed using ImmunoSpot software (Cellular Technology). For pentamer staining, cells were labeled with PE-MHC class I pentamer (Proimmune) consisting of murine H-2K$^b$ complexed to SIYRYYGL (SIY) peptide or to control SIINFEKL peptide, and stained with CD3-AX700 (Ebioscience, 17A2), CD8-PacBlue (Biolegend, 53-6.7), CD4-APC (Pharmingen, RM4-5), CD62L-PECy7 (Ebioscience, MEL-14), CD44-FITC (BD, IM7) and Fixable Viability-ef780 (Ebioscience). Stained cells were analyzed using an LSR II cytometer with FACSDiva software (BD). Data analysis was conducted with FlowJo software (Tree Star).

Fecal Transfers and αPD-L1 mAb Immunotherapy:

Fecal pellets from JAX and TAC-derived mice were collected upon arrival in our facility and each fecal pellet was resuspended in 1 ml of phosphate-buffered saline (PBS). The supernatant from each fecal pellet was used for oral gavage of two recipient mice, 100 μl per gavage. For prophylactic fecal transfer experiments mice were gavaged with JAX or TAC fecal suspensions once a week for two weeks prior to tumor inoculation. For therapeutic fecal transfer experiments, mice were gavaged on days 7 and 14 post tumor implantation. For combination therapy experiments, mice were additionally injected intraperitoneally with 100 μg αPD-L1 mAb (BioXCell) in 100 μl PBS on days 7, 10, 13 and 16 post-tumor implantation.

Microbial DNA Analysis:

Bacterial DNA was extracted from murine fecal pellets using PowerSoil®-htp 96 Well Soil DNA Isolation Kit (MoBio cat.#12955-4). The V4-V5 region of the 16S rRNA encoding gene was amplified (earthmicrobiome.org/emp-standard-protocols/; Earth Microbiome Project, 2011) and sequenced at the High-Throughput Genome Analysis Core at Argonne National Laboratory. Quantitative Insights Into Microbial Ecology (QIIME) was used to trim and classify sequences (Caporaso et al. Bioinformatics 26, 266-267 (2010); herein incorporated by reference in its entirety); specifically, the open reference OTU picking protocol was used at 97% sequence identity against the Greengenes database (05/13 releaseX McDonald et al. The ISME journal 6, 610-618 (2012); herein incorporated by reference in its entirety). PYNAST was used to align sequences (Caporaso et al. Nat Meth 7, 335-336 (2010); herein incorporated by reference in its entirety) and RDP Classifier was used for taxonomic assignment (Wang et al. Appl Environ Microbiol 73, 5261-5267 (2007); herein incorporated by reference in its entirety). Community structure was compared using weighted and unweighted UniFrac distances (Lozupone et al. Appl Environ Microbiol 71, 8228-8235 (2005); herein incorporated by reference in its entirety). G-test was performed to determine differences in bacterial taxa occurrence between fecal communities. Principal Coordinate Analysis (PCoA) ordination were generated to visually compare beta diversity and Analysis of Similarity (ANOSIM) test statistics were performed to statistically compare within- to between-group similarity in QIIME.

Bacterial Administration and Heat Inactivation:

A cocktail of lyophilized *Bifidobacterium* species (*B. bifidum*, *B. longum*, *B. lactis* and *B. breve*, Seeking Health) were resuspended in PBS at $5\times10^9$ CFU/ml. Each mouse was given 200 μl of *Bifidobacterium* ($1\times10^9$ CFU/mouse) by oral gavage 7 and 14 days following tumor inoculation. Heat inactivation was performed by boiling rehydrated bifidobacteria at 100° C. for 2 hours. Heat-treated and live bifidobacteria were serially diluted in reduced PBS and plated on reduced clostridial medium (RCM) agar in anaerobic conditions. Plates were subsequently incubated in an anaerobic chamber for three days to test efficacy of killing. *Lactoba-* cillus murinus was cultured in MRS broth overnight, then washed and resuspended in PBS at $5 \times 10^{10}$ CFU/ml. Each mouse was orally gavaged with 100 µl of bacterial suspension ($5 \times 10^9$ CFU/mouse) 7 and 14 days following tumor inoculation.

CFSE-Labeled 2C CD8+ T Cell Adoptive Transfer:

CD8+ T cells were isolated from the spleen and lymph node of naïve CD45.1/.2+ 2C TCR Tg mice using the MACS CD8 T cell Isolation Kit (Miltenyi, Cat No. 130-095-236), labeled with 2.5 mM CFSE and injected i.v. into CD45.2+ C57BL/6 mice derived from either JAX or TAC. 24 hours later, mice were inoculated with $1 \times 10^6$ B16.SIY melanoma cells s.c. Seven days post-adoptive T cell transfer, spleen and tumor-draining lymph node were harvested and restimulated ex-vivo with SIY peptide in the presence of brefeldin A. Samples were stained with Fixable Viability-ef780 (Ebioscience), CD45.1-PerCPCy5.5 (Ebioscience, E20), CD45.2-APC (Ebioscience, 104), CD3-AX700 (Ebioscience, 17A2), CD8-BV711 (Biolegend, 53-6.7), CD4-BV605 (Biolegend, RM4-5) and IFN-γ-PE (BD, XMG1.2). Intracellular IFN-γ production and CFSE dilution were assessed in gated CD45.1/.2+ 2C CD8+ T cells by flow cytometry.

Dendritic Cell Sorting and Gene Expression Profiling:

TAC mice were gavaged with *Bifidobacterium* once a week for two weeks. *Bifidobacterium*-fed mice, newly arrived JAX mice, and newly arrived TAC mice were inoculated subcutaneously in both flanks with $5 \times 10^6$ DRAQ5-labeled B16.SIY tumor cells. 40 hrs following tumor implantation, whole tumors including infiltrating immune cells were digested in collagenase (Worthington) and filtered into single cell suspensions. Samples from 5 mice in each group were pooled and subsequently stained with Fixable Viability-ef506 (Ebioscience), CD45-AF488 (Biolegend, 30-F11), CD3-ef450 (Ebioscience, 145-2C11), CD19-PB (Ebioscience, 1D3), I-A/I-E-PECy7 (Biolegend, M5/114.15.2), CD11c-PE (Ebioscience, N418) and CD11b-PerCpCy5.5 (BD, M1/70). Live CD45+CD3−CD19− MHCII$^{hi}$CD11c+ dendritic cells were sorted directly into RLT Buffer (Qiagen) using FACSAriaIII (BD) and stored immediately on dry ice. Total RNA was isolated using RNeasy® Micro kit (Qiagen). RNA was submitted to the Functional Genomics Facility at the University of Chicago for gene expression profiling. RNA integrity and concentration were assessed using an Agilent Bioanalyzer 2100, and all RNA samples used for microarray analysis had an RNA Integrity Number >9.0. Total RNA was processed into biotinylated cRNA using the Epicentre TargetAmp™ 2-Round Biotin-aRNA Amplification Kit 3.0 (TAB2R71024). The cRNA was hybridized to Illumina MouseRef8v2 arrays using Illumina provided protocols and scanned using an Illumina HiScan. Quantile normalized and background subtracted values were subsequently analyzed using R. Genes whose expression value was under 10 were removed from the analysis. Mean fold-change in gene transcript levels between JAX samples relative to TAC, and BIF samples relative to TAC were calculated, and genes whose fold change was over 1.5 in both comparisons (761 gene transcripts) were inputted into The Database for Annotation, Visualization and Integrated Discovery (DAVID) v6.7 for pathway analysis. Genes found to be significantly enriched (p<0.05) for immune function were then plotted in a heatmap using R software.

Statistical Analysis:

Tumor growth curves were analyzed using two-way ANOVA, with either Sidak's multiple comparisons posttest for comparison of two groups, or Tukey's multiple comparisons posttest for comparison of more than two groups. For comparisons other than tumor growth, Mann Whitney's non-parametric T-test was used when comparing two groups and one-way ANOVA with Tukey's multiple comparisons posttest was used when comparing more than two groups. P<0.05 was considered statistically significant and denoted as follows: *p<0.05, p<0.01, *p<0.001, ****p<0.0001. Statistical analysis was performed using GraphPad PRISM.

Example 2

Results

Figure 1D:
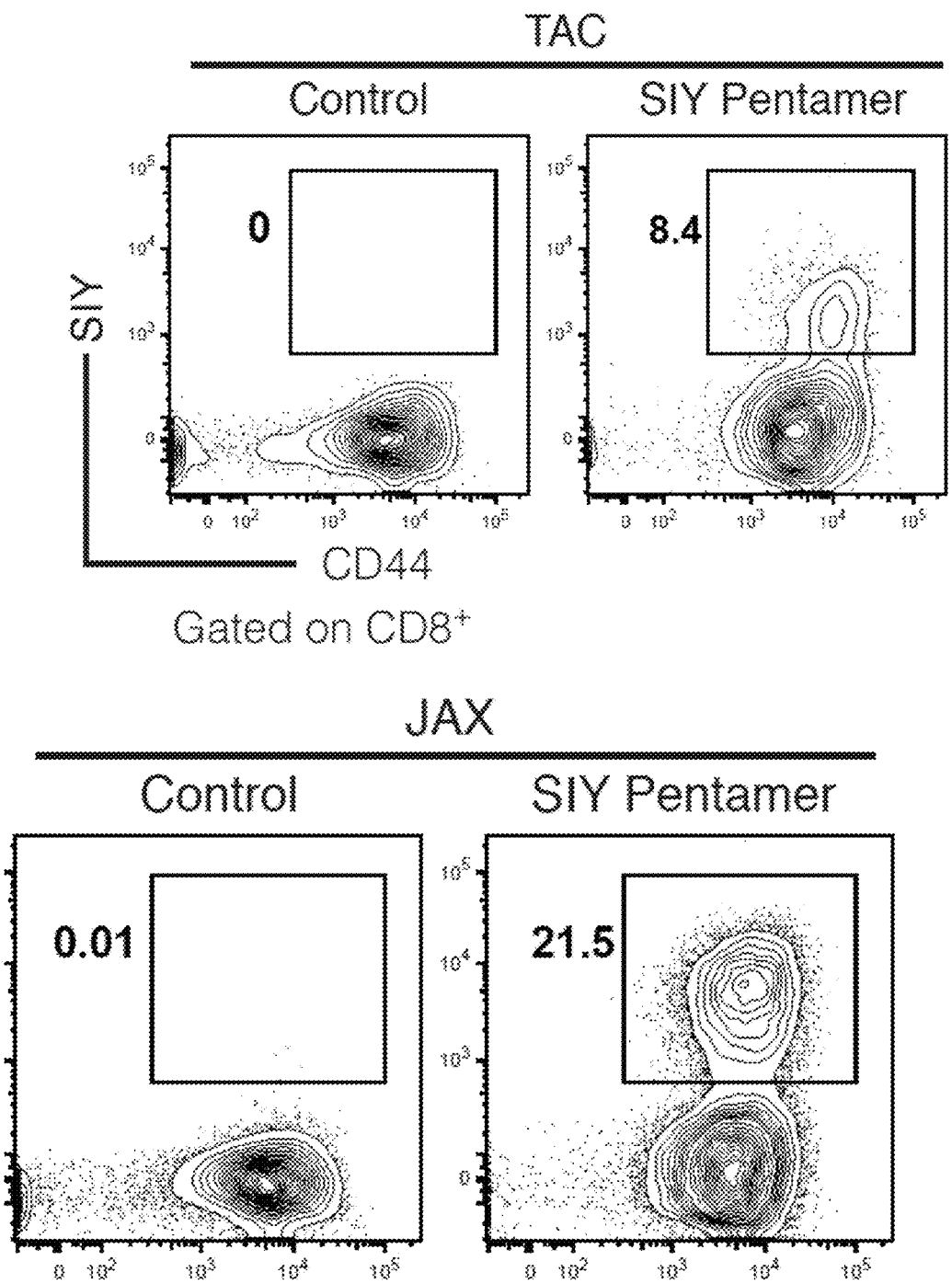
Figure 1E:
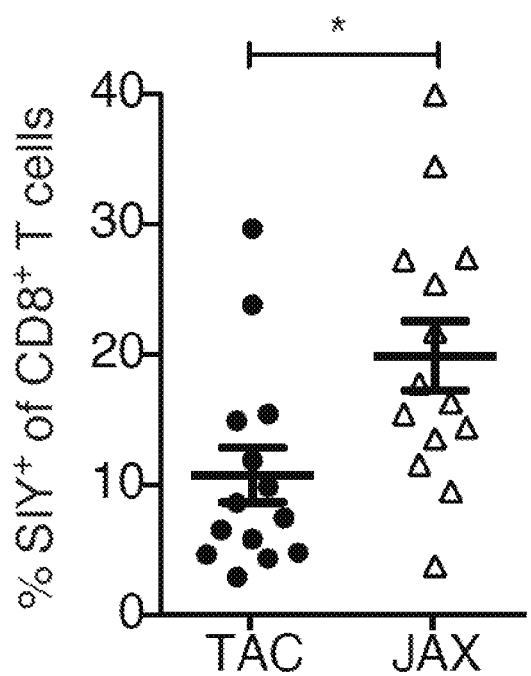
Figure 1F:
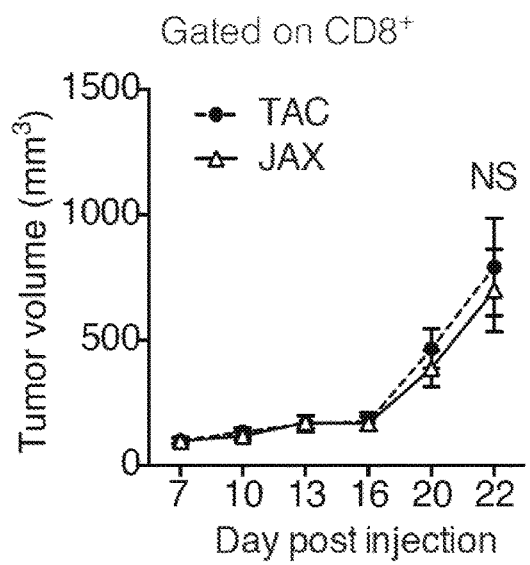
Figure 1G:
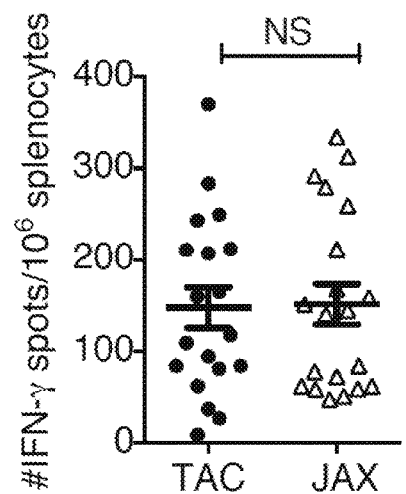
Figure 1H:
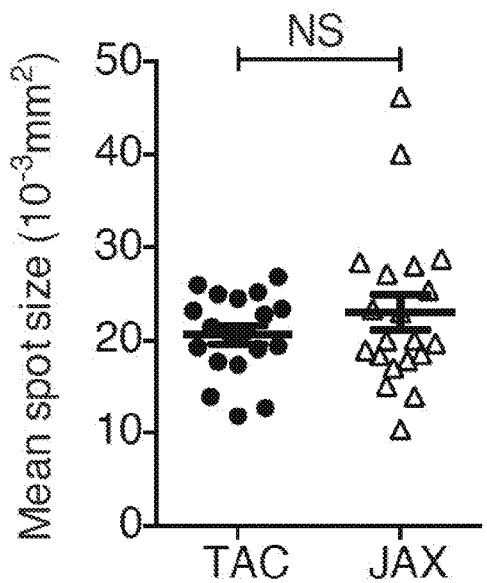
Figure 1I:
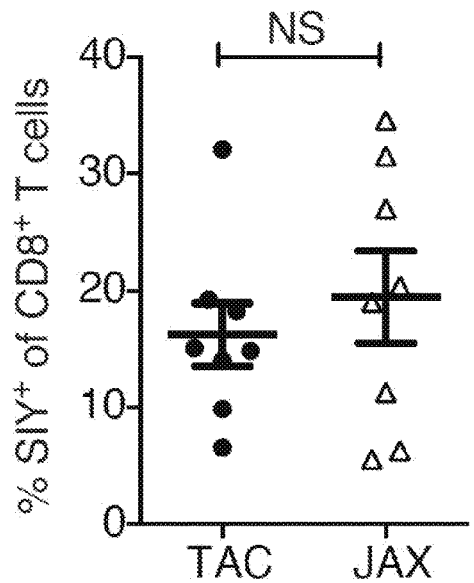

Experiments were conducted during development of embodiments of the present invention to test whether differences in the specific composition of the normal microbiota influence the immune response to a growing tumor in vivo. Subcutaneous B16.SIY melanoma growth was observed in genetically similar C57BL/6 mice derived from two different mouse facilities, Jackson Laboratory (JAX) and Taconic Farms (TAC), which have been shown to differ in their commensal microbes (Ivanov et al. Cell 139, 485-498 (2009); herein incorporated by reference in its entirety). It was found that JAX and TAC mice exhibited significant differences in B16.SIY melanoma growth rate, with tumors growing more aggressively in TAC mice (FIG. 1A). To evaluate whether this difference was immune-mediated, tumor antigen-specific T cell responses, as well as T cell accumulation in the tumor microenvironment, were assessed. In fact, tumor-specific T cell responses were significantly higher in JAX mice (FIGS. 1B and 1C), and markedly increased numbers of tumor-infiltrating T cells were observed (FIG. 1D). To begin to address whether this difference could be mediated by commensal microbiota, JAX and TAC mice were co-housed for 3 weeks prior to tumor implantation. It was found that co-housing ablated the differences in tumor growth (FIG. 1E) and immune responses (FIG. 1F-H) between the two mouse populations, arguing for an environmental influence. Notably, TAC mice appeared to acquire the JAX phenotype upon cohousing, indicating that JAX mice might be colonized by commensal microbes that dominantly facilitate improved anti-tumor immunity.

Figure 5B:
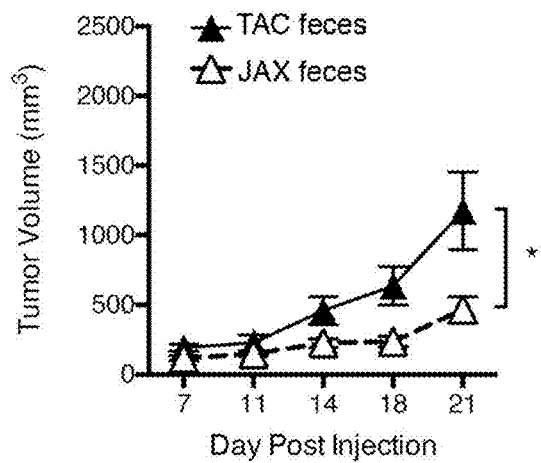

To directly test the role of commensal bacteria in regulating anti-tumor immunity, JAX fecal suspensions or control TAC fecal suspensions were transferred into TAC recipients by oral gavage prior to tumor implantation FIG. 5A). Strikingly, it was found that prophylactic transfer of JAX fecal material into TAC recipients was sufficient to delay tumor growth (FIG. 2A) and enhance induction and infiltration of tumor-specific CD8+ T cells (FIGS. 2B-C and 5B), supporting a microbe- or microbial product-derived effect. Reciprocal transfer of TAC fecal material into JAX recipients resulted in only a minimal increase in tumor growth rate and did not significantly alter anti-tumor T cell responses (FIG. 2A-C and FIG. 5B).

Figure 2A:
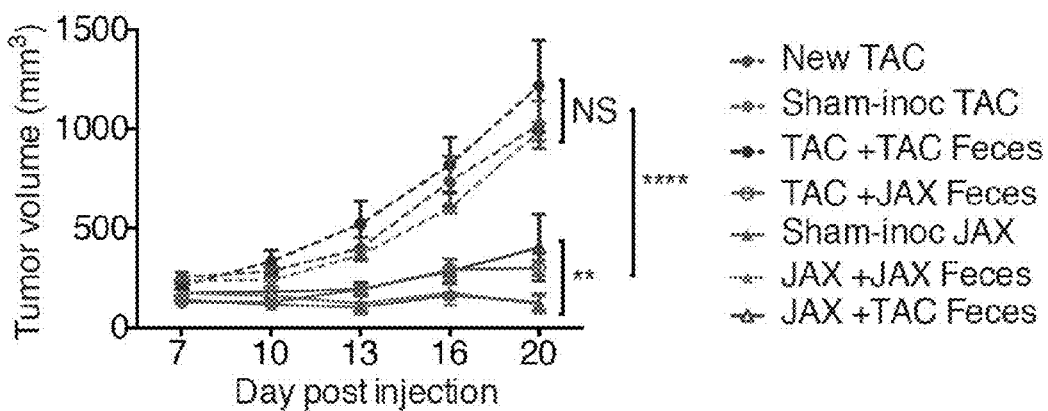
FIG. 2A-G. Oral administration of JAX fecal material to TAC mice enhances spontaneous anti-tumor immunity and response to αPD-L1 mAb therapy. (A) B16.SIY tumor growth in newly arrived TAC mice, TAC and JAX mice orally gavaged with PBS, TAC or JAX fecal material prior to tumor implantation. (B) Number of IFN-γ spots×mean spot size ($10^{-3}$ mm$^2$), determined by ELISPOT 7 days following tumor inoculation. (C) Percentage of SIY$^+$ CD8$^+$ T cells within the tumor of TAC and JAX mice treated as in (A), 21 days post-tumor inoculation. Representative plots (left), quantification (right). (D) B16.SIY tumor growth in TAC mice, untreated or treated with JAX fecal material 7 and 14 days post tumor implantation, αPD-L1 mAb 7, 10, 13 and 16 days post tumor implantation, or both regimens. (E) IFN-γ ELISPOT assessed 5 days after start of treatment. (F) Percentage of tumor-infiltrating SIY$^+$ CD8$^+$ T cells, determined by flow cytometry 14 days after start of treatment. (G) B16.SIY tumor growth kinetics in TAC and JAX mice, untreated or treated with αPD-L1 mAb 7, 10, 13 and 16 days post tumor implantation.
Figure 2B:
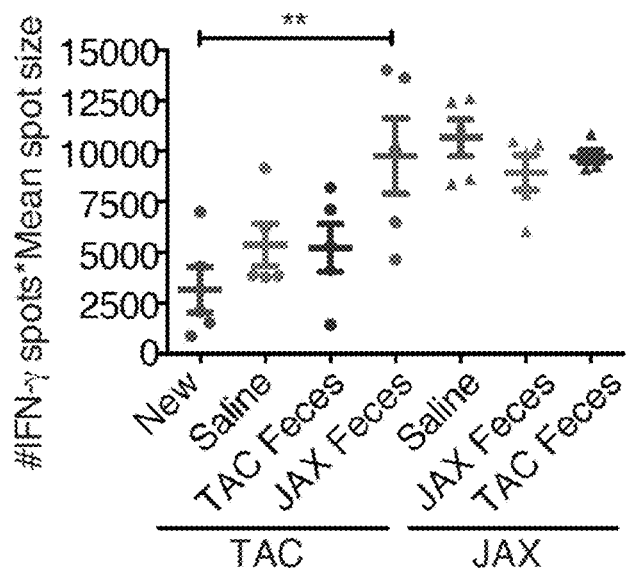
Figure 2C:
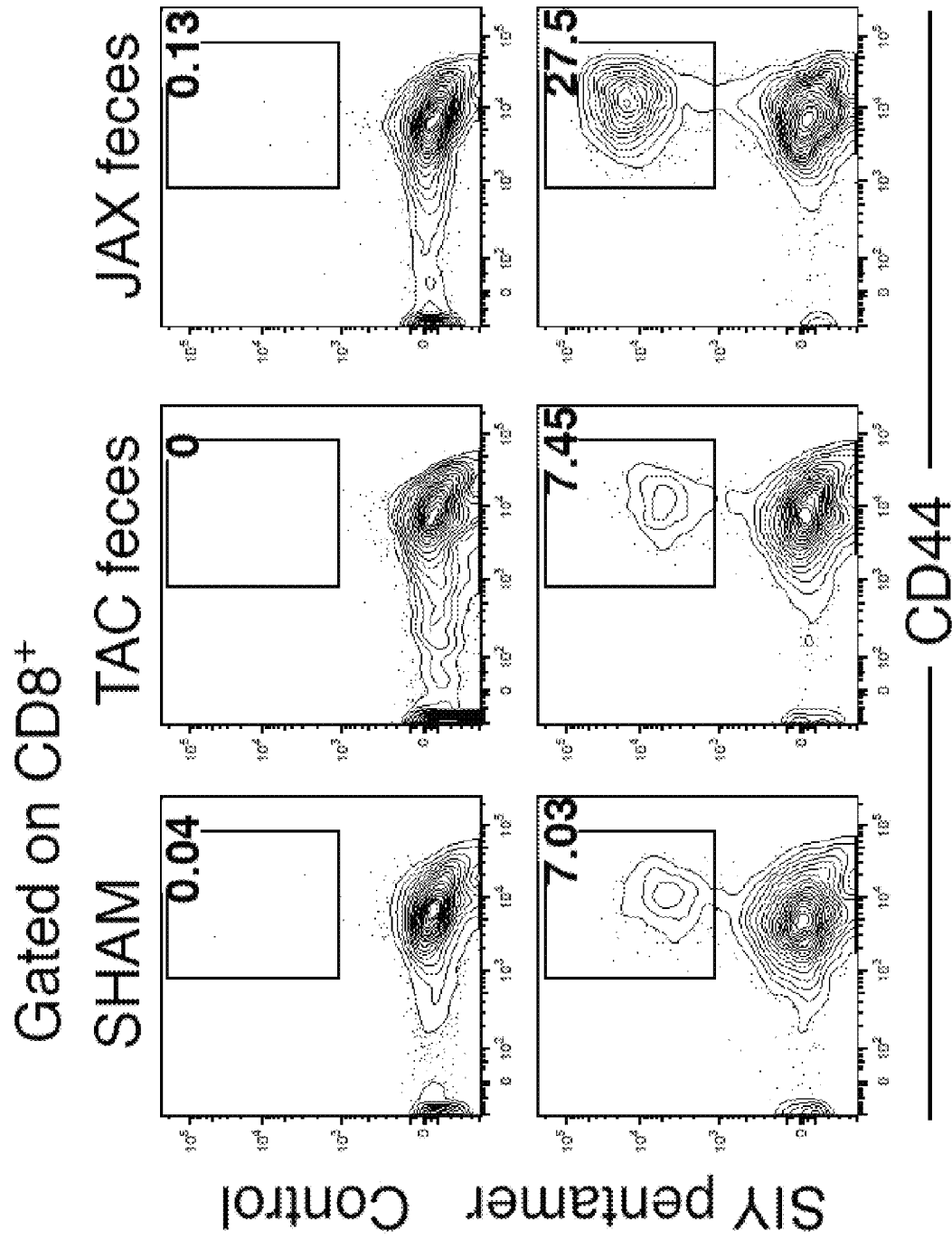
Figure 2C:
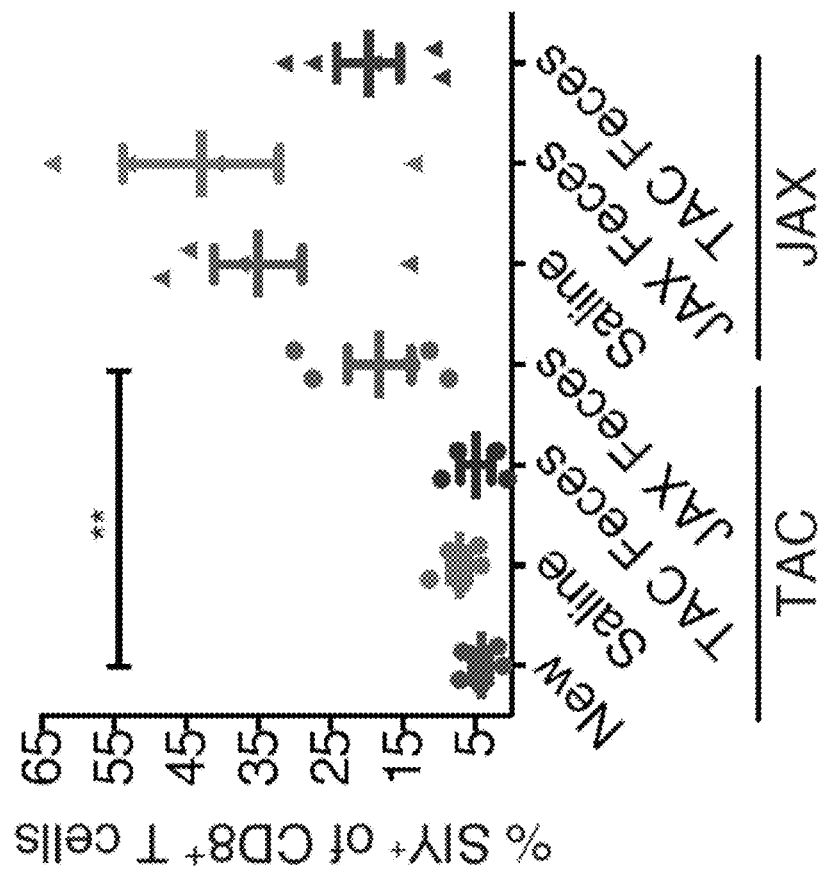
Figure 2D:
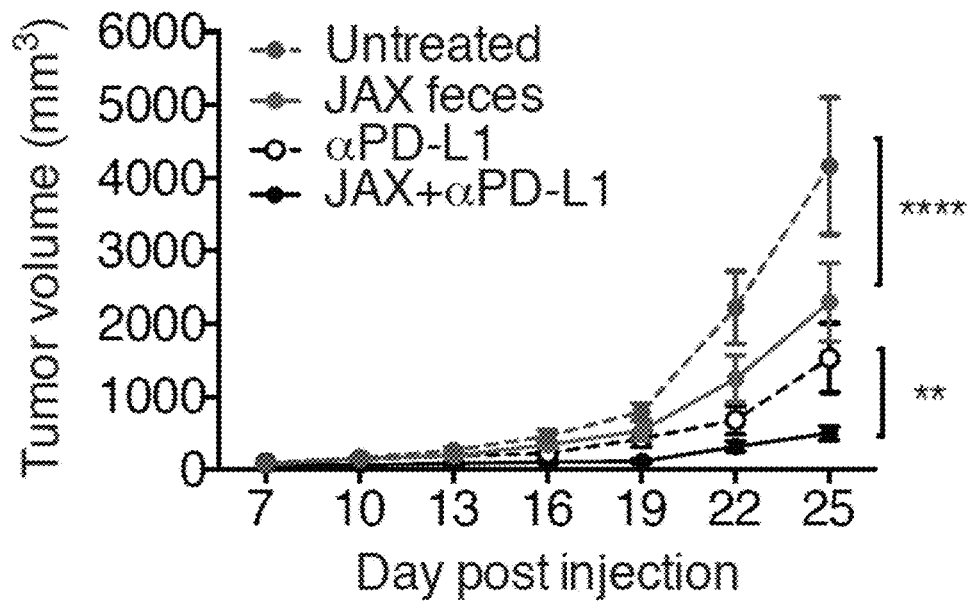
Figure 2E:
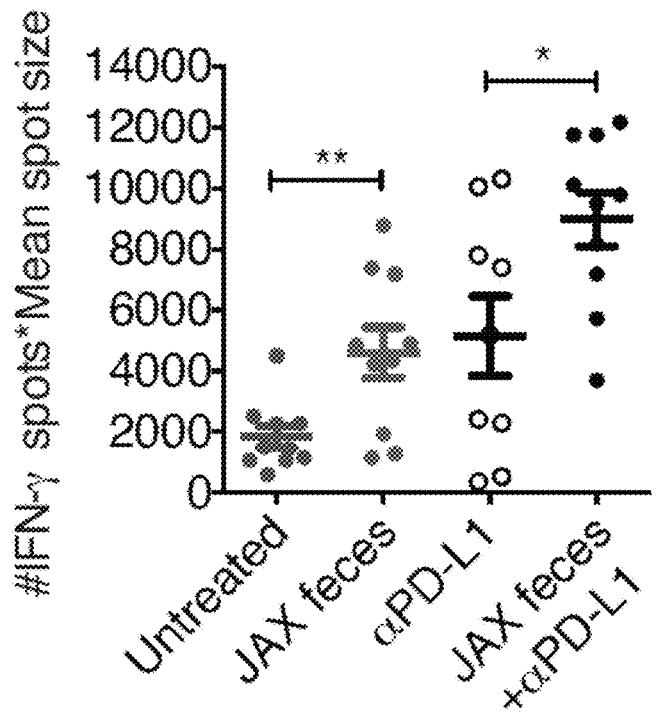
Figure 2F:
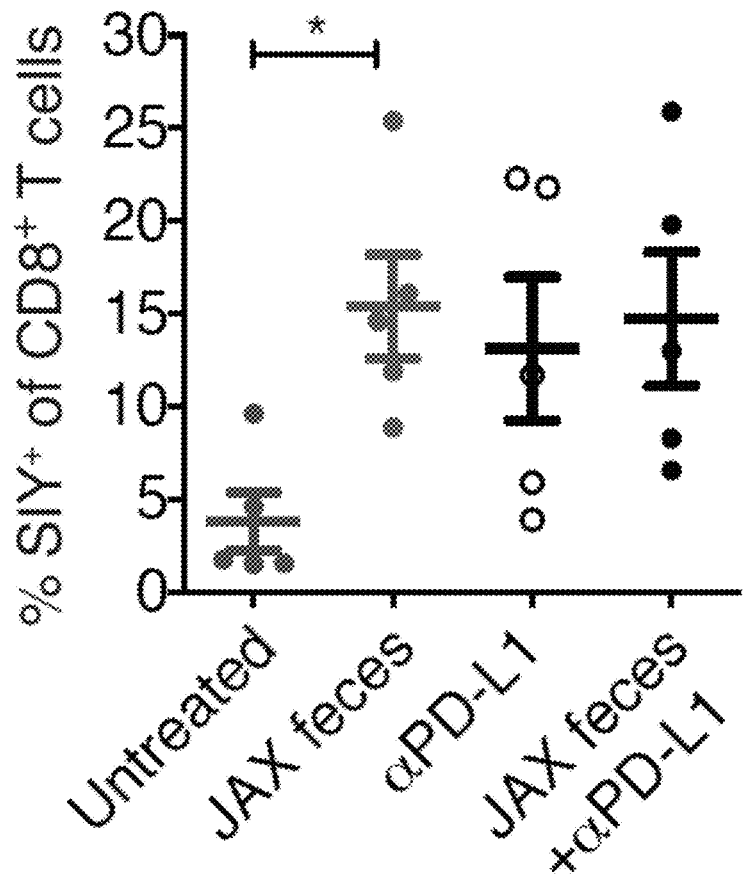
Figure 2G:
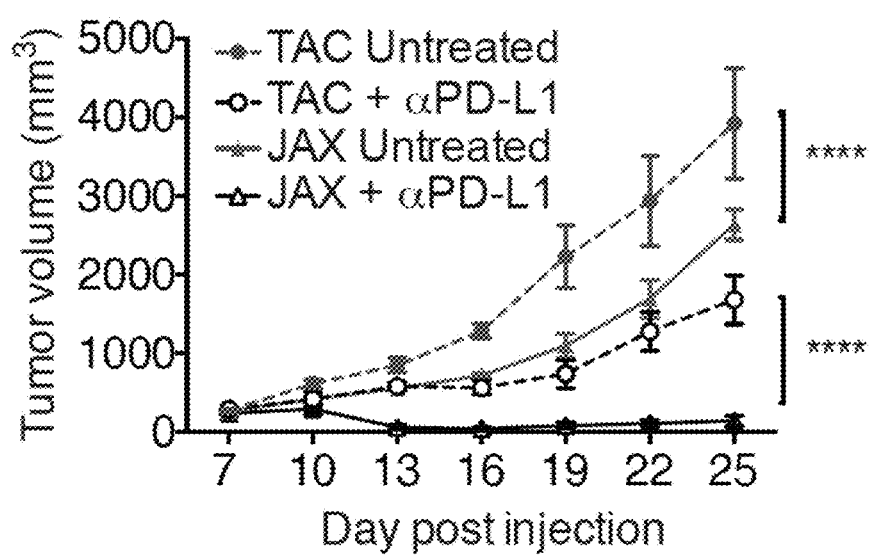
Figure 5C:
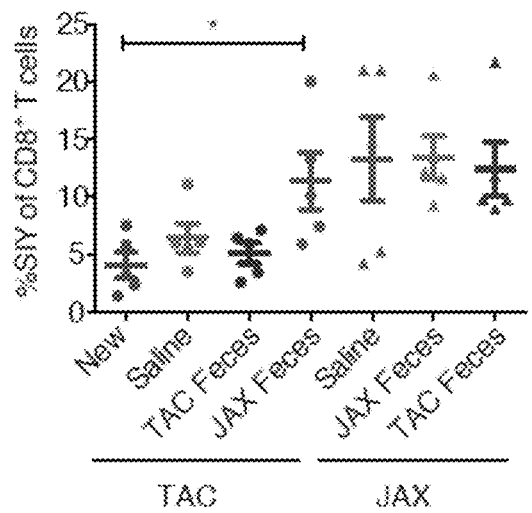
Figure 5D:
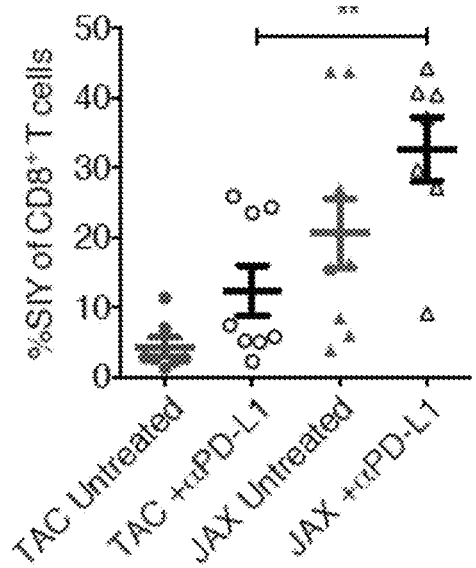

To test whether manipulation of the microbial community could be effective as a therapy, we administered JAX fecal material alone or in combination with antibodies targeting PD-L1 (αPD-L) to TAC mice bearing established tumors. Transfer of JAX fecal material alone resulted in significantly slower tumor growth (FIG. 2D), accompanied by increased tumor-specific T cell responses (FIG. 2E) and infiltration of antigen-specific T cells into the tumor (FIG. 2F), to the same degree as treatment with systemic αPD-L1 mAb. Combination treatment with both JAX fecal transfer and αPDL1 mAb improved tumor control (FIG. 2D) and circulating tumor antigen-specific T cell responses (FIG. 2E), while there was little additive effect on accumulation of activated T cells within the tumor microenvironment (FIG. 2F). Consistent with these results, αPD-L1 therapy alone was significantly more efficacious in JAX mice compared to TAC mice (FIG. 2G), which paralleled improved anti-tumor T cell responses (FIG. 5C). These data indicate that the commensal microbial composition can influence spontaneous anti-tumor immunity as well as response to immunotherapy with αPD-L1 mAb.

Figure 3A:
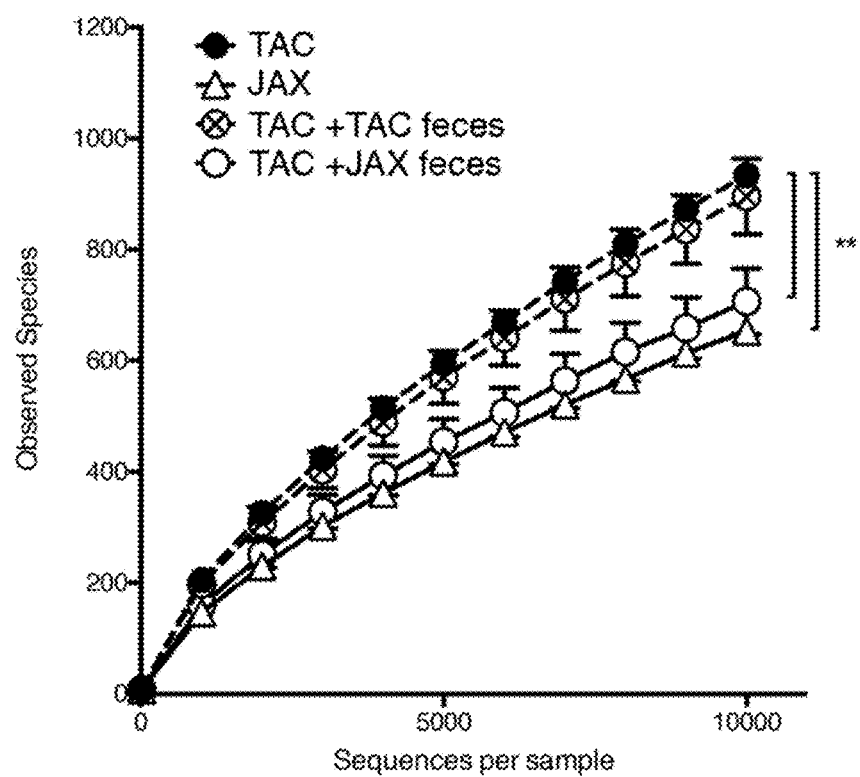
FIG. 3A-G. Direct administration of *Bifidobacterium* to TAC recipients with established tumors improves tumor-specific immunity and response to αPD-L1 mAb therapy. (A-C) Bacterial species diversity (A), principal coordinate analysis plot of bacterial β-diversity (B) and operational taxonomic unit (OTU) levels of top *Bifidobacterium* taxon (C) in fecal material obtained from JAX, TAC, TAC-fed TAC and JAX-fed TAC mice. Comparisons in A-C were performed using 9-10 replicates from each vendor and 4-5 replicates from each treatment. (D) B16.SIY tumor growth kinetics in TAC mice, untreated or treated with *Bifidobacterium* 7 and 14 days post tumor implantation (white arrows), αPD-L1 mAb 7, 10, 13 and 16 days post tumor implantation (black arrows) or both regimens. (E) IFN-γ ELISPOT assessed 5 days after start of treatment. (F) Percentage of tumor-infiltrating SIY$^+$ CD8$^+$ T cells, determined by flow cytometry 14 days following start of treatment. Representative plots (left), quantification of data combined from 2 independent experiments (right). (G) B16.SIY tumor growth for isotype-treated (left) or CD8-depleted (right) groups as in D.
Figure 3B:
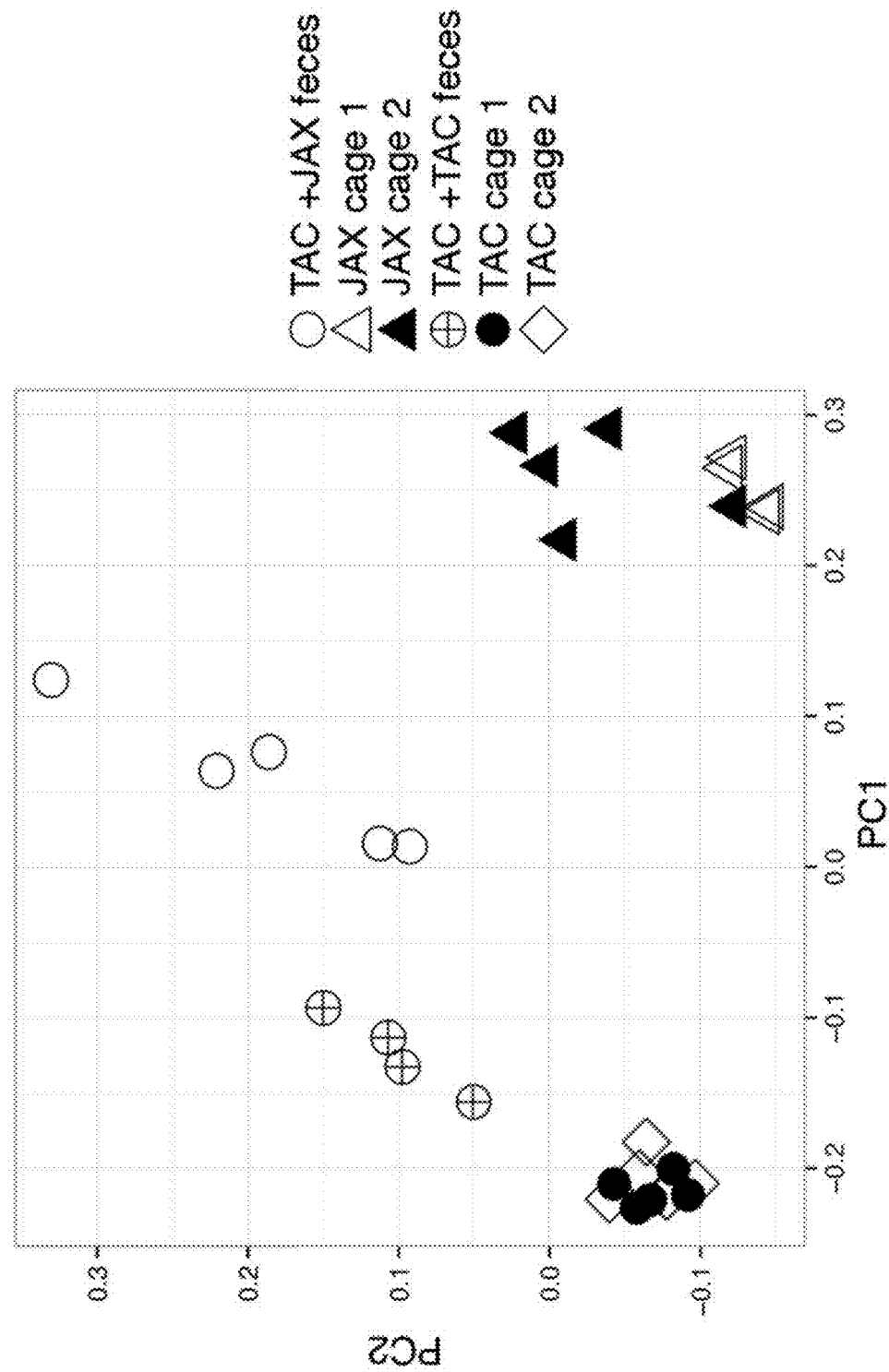
Figure 8A:
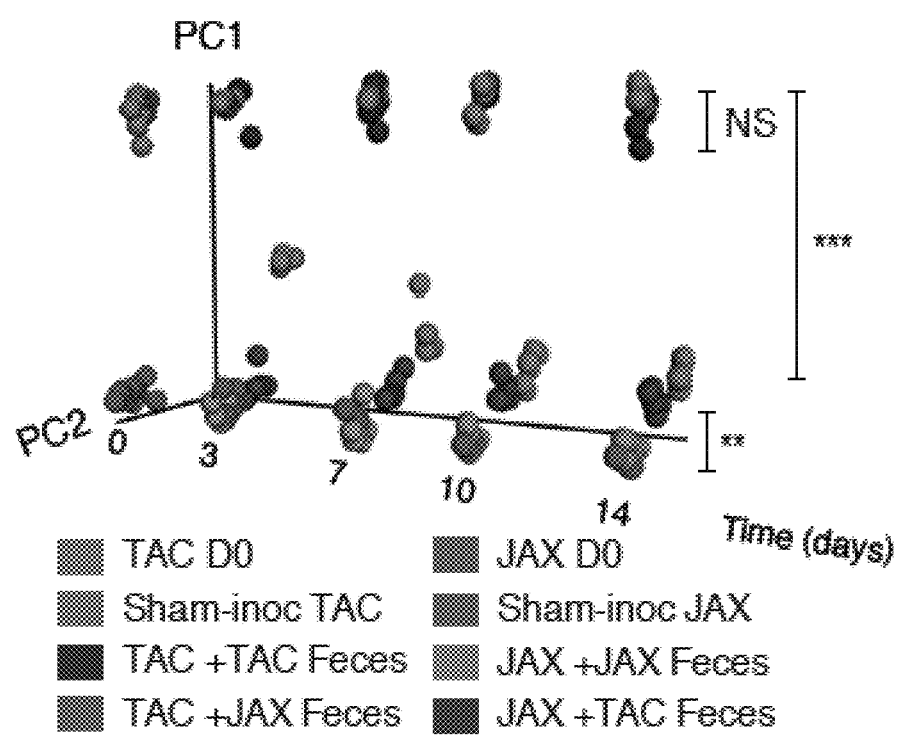
FIG. 8A-G. Direct administration of *Bifidobacterium* to TAC recipients with established tumors improves tumor-specific immunity and response to αPD-L1 mAb therapy. (A) Principal coordinate analysis plot of bacterial β-diversity over time in groups treated as in FIG. 2A. (B) Phylogenetic analysis of taxa that are of significantly different abundance in newly arrived JAX vs TAC mice FDR<0.05 (non-parametric t test); bars represent log-transformed fold changes, inner circle=log 10(10); middle circle=log 10(100); outer circle=log 10(1000). (C) Heatmap demonstrating relative abundance over time of significantly altered genus-level taxa in JAX-fed TAC mice FDR<0.05 (non-parametric t test); columns depict individual mice; each timepoint shows mice from two separate cages, 3-4 mice per cage. (D) Correlation plot of relative abundance of *Bifidobacterium* OTU_681370 in fecal material obtained from groups as in (A) 14 days post arrival and frequency of SIY$^+$ CD8$^+$ T cells in tumor; p=1.4×10-5, FDR=0.0002, R2=0.86 (univariate regression). (E) B16.SIY tumor growth kinetics in TAC mice, untreated or treated with *Bifidobacterium* 7 and 14 days post tumor implantation, αPD-L1 mAb 7, 10, 13 and 16 days post tumor implantation, or both regimens. (F) IFN-γ ELISPOT assessed 5 days after start of treatment. (G) Percentage of tumor-infiltrating SIY$^+$ CD8$^+$ T cells, determined by flow cytometry 14 days following start of treatment.

To identify specific bacteria associated with protective anti-tumor immune responses, the fecal bacterial content in mice obtained from TAC mice, JAX mice, and JAX-fed and TAC-fed TAC mice we compared using the 16S ribosomal RNA (rRNA) miSeq Illumina platform. Overall, 933.9±55.2 taxa were identified in TAC mice and 653.4±60 taxa were identified in JAX mice, demonstrating decreased species diversity in mice obtained from JAX. TAC mice that were orally administered JAX fecal material showed decreased taxa diversity (706.6±117.9, p=0.006) similar to JAX mice, whereas TAC mice that were administered TAC fecal material did not show altered diversity (895.7±118, p=1, FIG. 3A). Principal coordinate analysis revealed that fecal samples analyzed from TAC mice that received JAX fecal material co-clustered separately from samples from control TAC mice and were more similar to samples obtained from JAX mice (FIG. 3B, and became similar to samples obtained from sham and JAX feces-inoculated JAX mice (FIG. 8A). In contrast, TAC-inoculated TAC mice did not change in community diversity relative to sham-inoculated TAC mice (p=0.4, ANOSIM). Analysis of similarity confirmed that TAC mice fed with JAX fecal material were more similar to each other than to TAC mice that were given TAC fecal material (p=0.008) or mice obtained from TAC (p=0.002). Reciprocal transfer of TAC fecal material into JAX hosts resulted in a statistically significant change in community diversity (p=0.003, ANOSIM), yet the distance of the microbial shift was smaller (FIG. 8A).

Figure 3C:
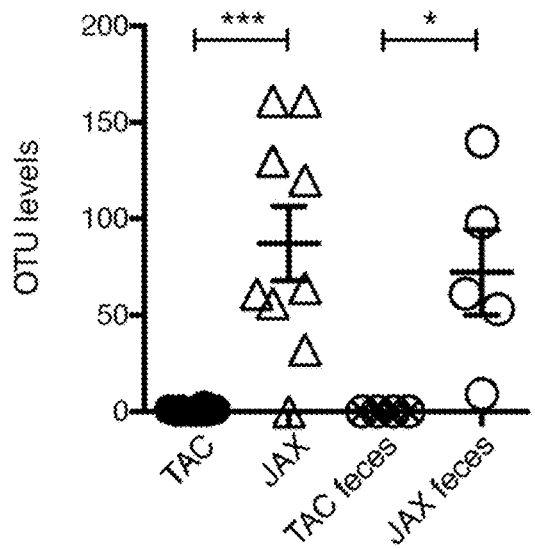
Figure 6A:
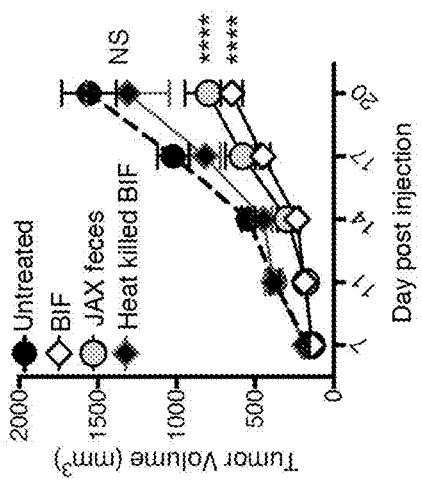
FIG. 6A-H. (A) Relative abundance of all taxa combined belonging to the *Bifidobacterium* genus in fecal material obtained from TAC, JAX, TAC-fed TAC and JAX-fed TAC mice. Comparisons were performed using 9-10 replicates from each vendor and 4-5 replicates from each treatment. (B) Number of colony forming units (CFU) of live and heat inactivated bifidobacteria, plated in RCM agar following serial dilution in reduced PBS and incubated in an anaerobic chamber for 72 hours. (C) B16.SIY tumor growth kinetics in TAC mice, untreated or treated with live *Bifidobacterium*, heat inactivated *Bifidobacterium* or JAX fecal material 7 and 14 days post tumor implantation. (D) Percentage of tumor-infiltrating SIY$^+$ T cells of total CD8$^+$ T cells for treatment groups as in C, determined by flow cytometry 14 days after start of treatment. C-D show data combined from 2-4 independent experiments, 5 mice per group. (E) B16.F10 tumor growth kinetics in TAC mice, untreated or treated with *Bifidobacterium* 7 and 14 days post tumor implantation. (F) MB49 tumor growth kinetics in TAC mice, untreated or treated with *Bifidobacterium* 7 and 14 days post tumor implantation. (G) B16.SIY tumor growth kinetics in TAC mice, untreated or treated with *Lactobacillus murinus* or JAX fecal material 7 and 14 days post tumor implantation. (H) Percentage of tumor-infiltrating SIY$^+$ T cells of total CD8$^+$ T cells for treatment groups as in G, determined by flow cytometry 18 days after start of treatment.
Figure 8B:
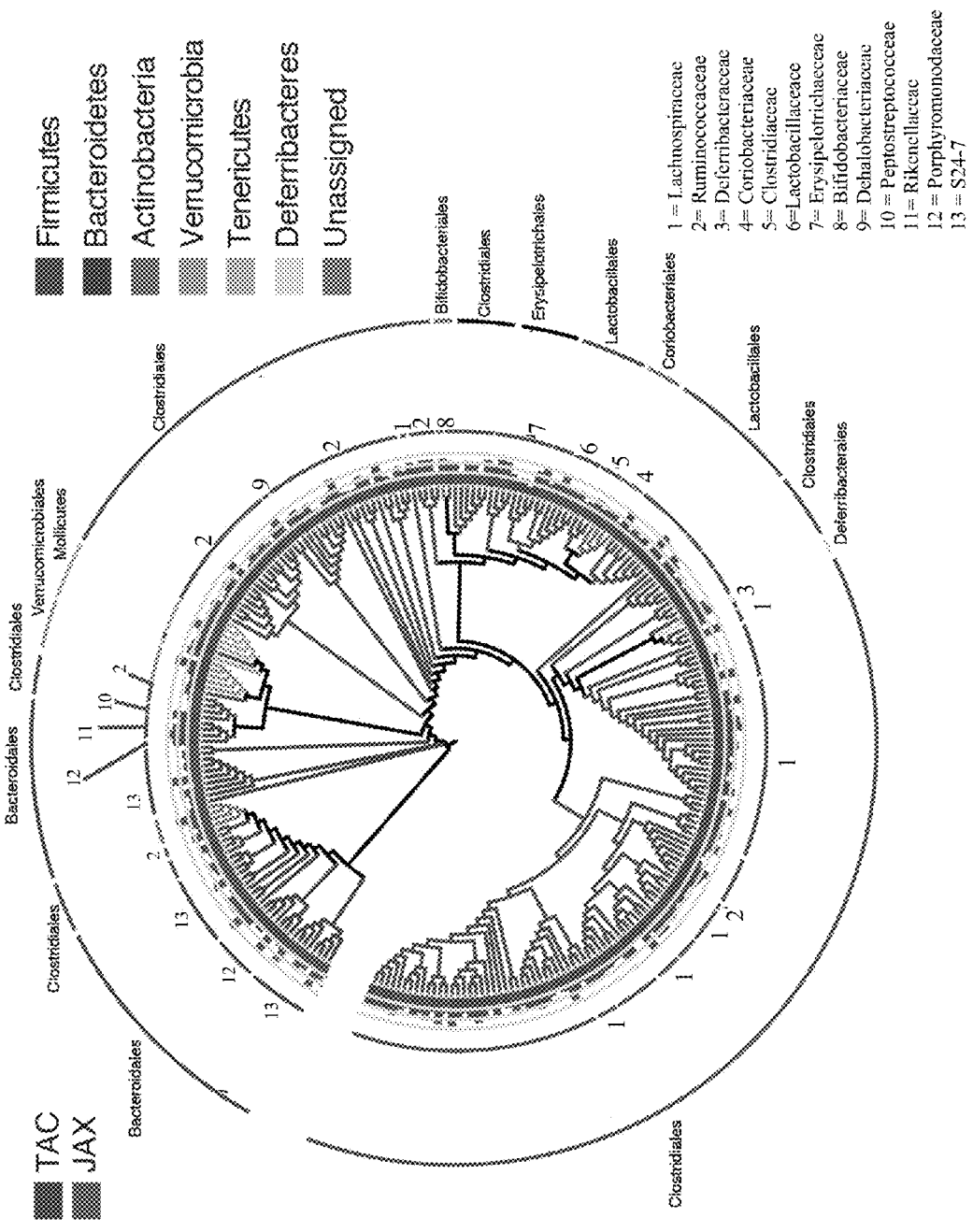
Figure 8C:
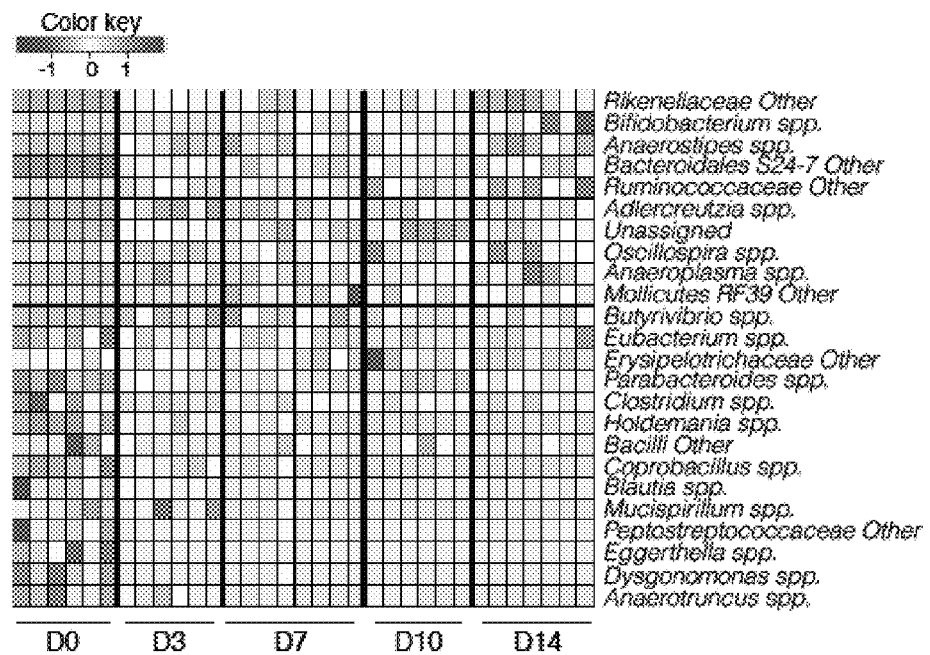

Comparative analysis of specific bacterial taxa showed that 97 taxa were significantly more abundant in JAX mice relative to TAC mice (FDR<0.05) (FIG. 8B), and 51 taxa were significantly increased in JAX-fed TAC mice relative to TAC-fed TAC mice (p<0.05). Only 32 taxa overlapped between these two comparisons, such that they were of greater abundance in both JAX mice and JAX-fed TAC mice. A significant association was observed for *Bifidobacterium*, which showed a positive association with anti-tumor T cell responses and increased in relative abundance over 400-fold in JAX-fed TAC mice (FIG. 8C). Members belonging to several of these groups were similarly altered in JAX-fed TAC mice relative to sham- or TAC-inoculated TAC mice (FIG. 8C). These included several unidentified taxa from the family S24-7 of the order Bacteroidales, one unassigned taxon, and four taxa with genus-level identifications, all of which are anaerobic gram-positive bacteria. Of these, the two most significant differentially abundant taxa belong to the *Bifidobacterium* genus, with the top *Bifidobacterium* taxon being over 200-fold more abundant in JAX relative to TAC (p=0.001), and similarly abundant in JAX-fed mice but not detected at all in TAC-fed TAC mice (p=0.01) (FIG. 3C). Comparison of relative abundance of all taxa combined belonging to the *Bifidobacterium* genus yielded similar results (FIG. 6A). Given that interactions between bifidobacteria and the host immune system have been described previously (Lopez et al. International journal of food microbiology 138, 157-165 (2010); Ménard et al. Applied and Environmental Microbiology 74, 660-666 (2008); Dong et al. Early human development 86, 51-58 (2010); herein incorporated by reference in their entireties), it was contemplated that members of this genus represent one source of the beneficial anti-tumor immune effects observed in JAX mice.

Figure 8D:
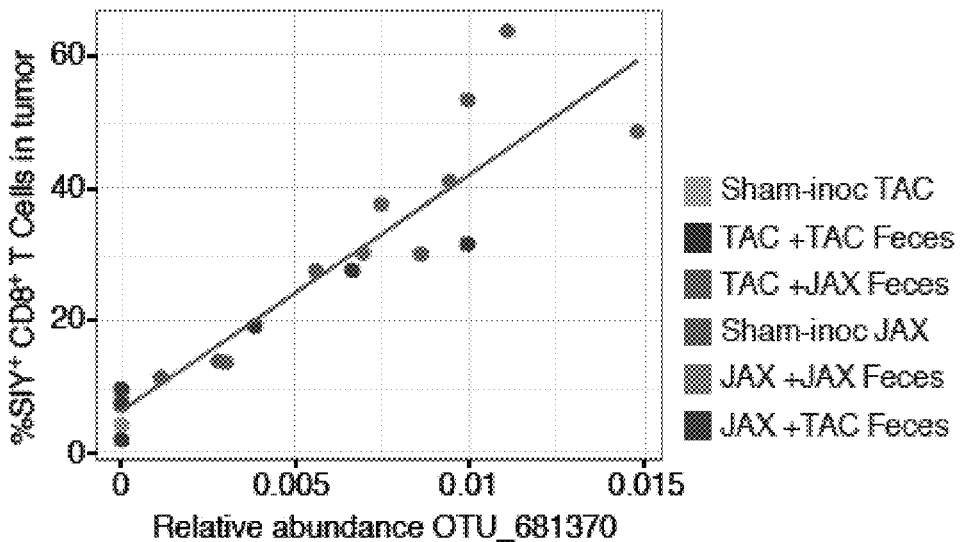
Figure 9D:
FIG. 9A-E. (A) Relative abundance of *Bifidobacterium* OTU_681370 in fecal material obtained from TAC mice 7 days following inoculation with commercial *Bifidobacterium* species. (B) *Bifidobacterium* levels in fecal material obtained from groups as shown, assessed by qPCR using genus-specific primers. (C) Representative plots showing percentage of SIY$^+$ T cells of total CD8$^+$ T cells within the tumor of untreated and *Bifidobacterium*-treated TAC mice, as assessed by flow cytometry 14 days following start of treatment. (D) *Bifidobacterium* levels in TAC mice 3 weeks post *Bifidobacterium* administration, assessed by qPCR. (E) B16.SIY tumor growth in TAC mice, untreated or inoculated with *Bifidobacterium* 6 weeks prior to tumor implantation.
Figure 9B:
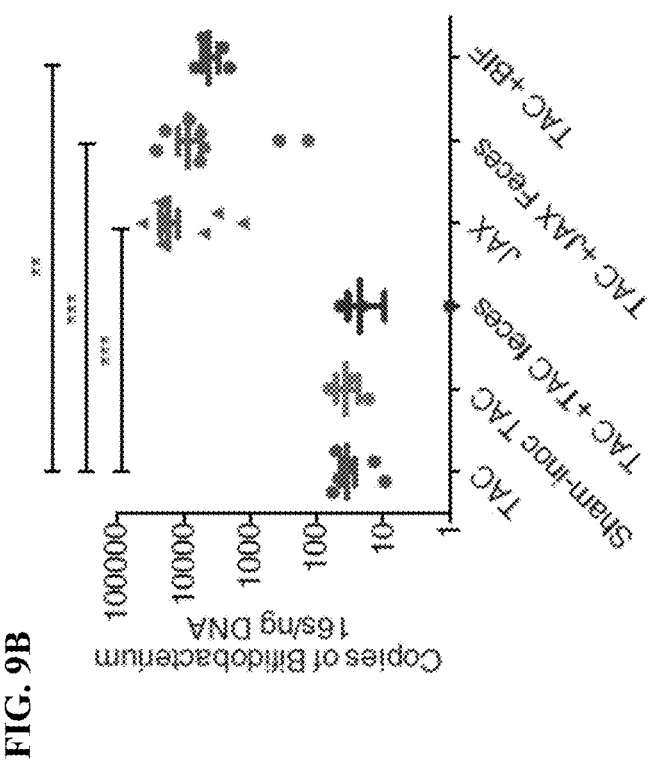
Figure 9A:
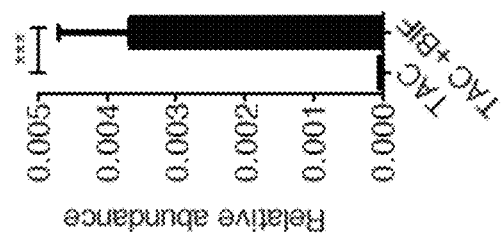

At the sequence level, *Bifidobacterium* operational taxonomic unit OTU_681370 showed the largest increase in relative abundance in JAX-fed TAC mice and the strongest association with anti-tumor T cell responses across all permutations (FIG. 8D). This bacterium was further identified as most similar to *B. breve*, *B. longum* and *B. adolescentis* (99% identity). To test whether *Bifidobacterium* spp. may be sufficient to augment protective immunity against tumors, a commercially available cocktail of *Bifidobacterium* species was obtained, which included *B. breve* and *B. longum* and administered this by oral gavage, alone or in combination with αPD-L1, to TAC 7 recipients bearing established tumors. Analysis of fecal bacterial content revealed that the most significant change in response to *Bifidobacterium* inoculation occurred in the *Bifidobacterium* genus (p=0.0009, FDR=0.015, non-parametric t-test), with a 120-fold increase in OTU_681370 (FIG. 9A), indicating that the commercial inoculum contained bacteria that were at least 97% identical to the taxon identified in JAX and JAX-fed TAC mice. An increase in *Bifidobacterium* could also be detected by quantitative PCR (FIG. 9B).

Figure 8G:
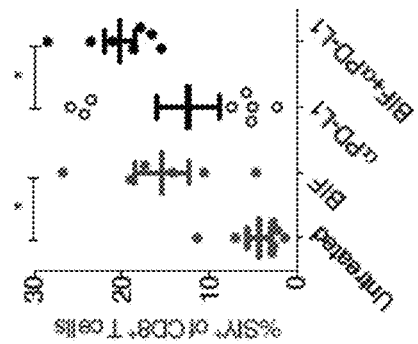
Figure 8F:
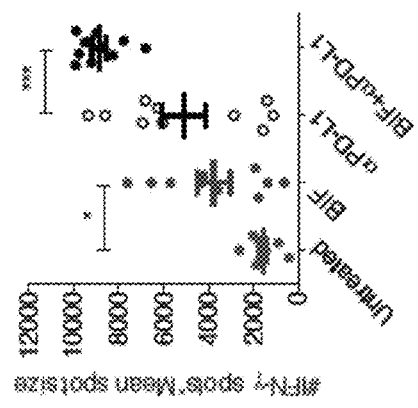
Figure 8E:
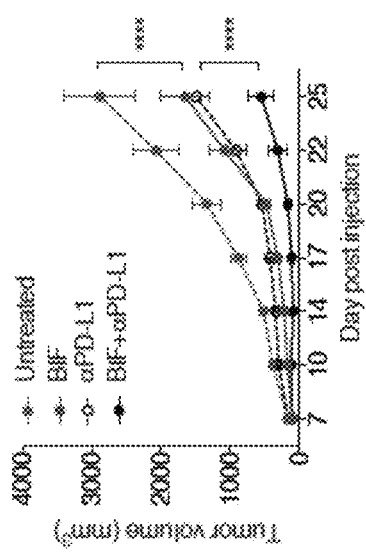
Figure 9C:
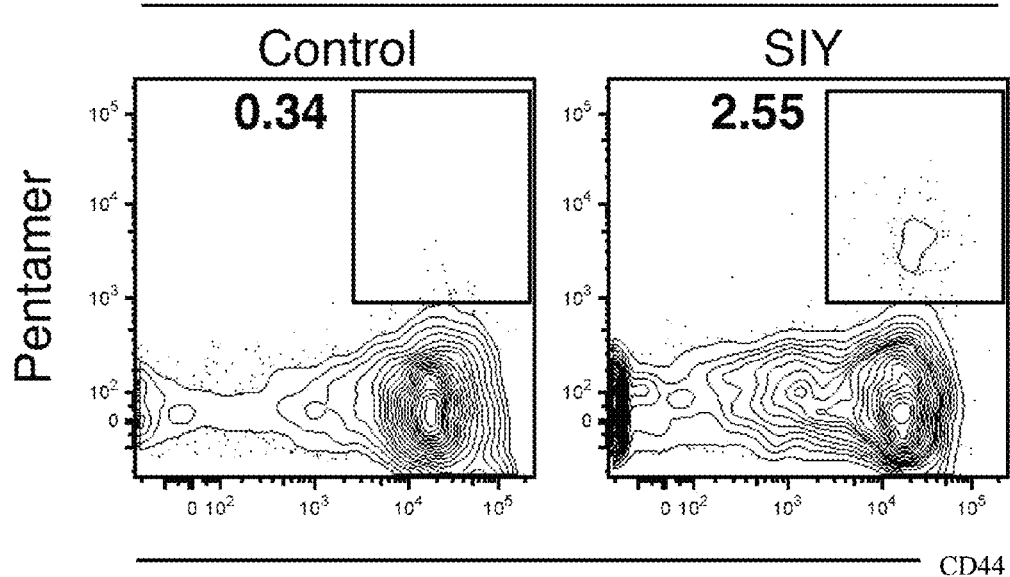
Figure 9C:
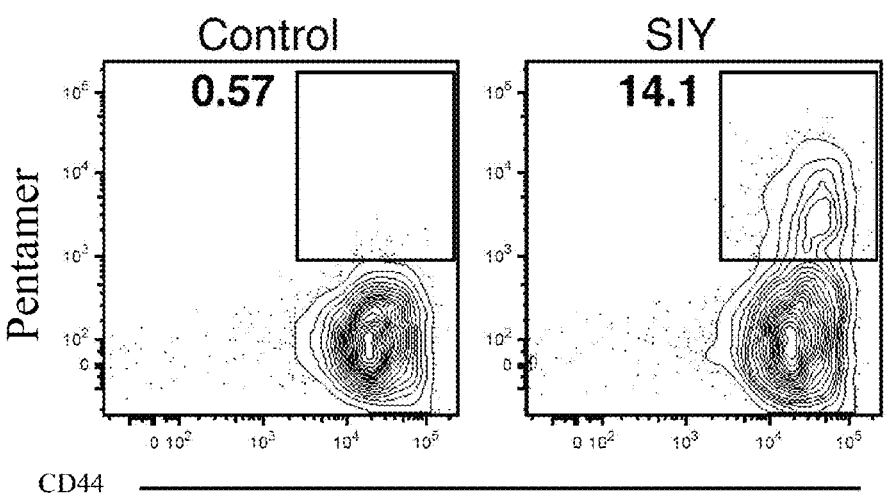
Figure 9E:
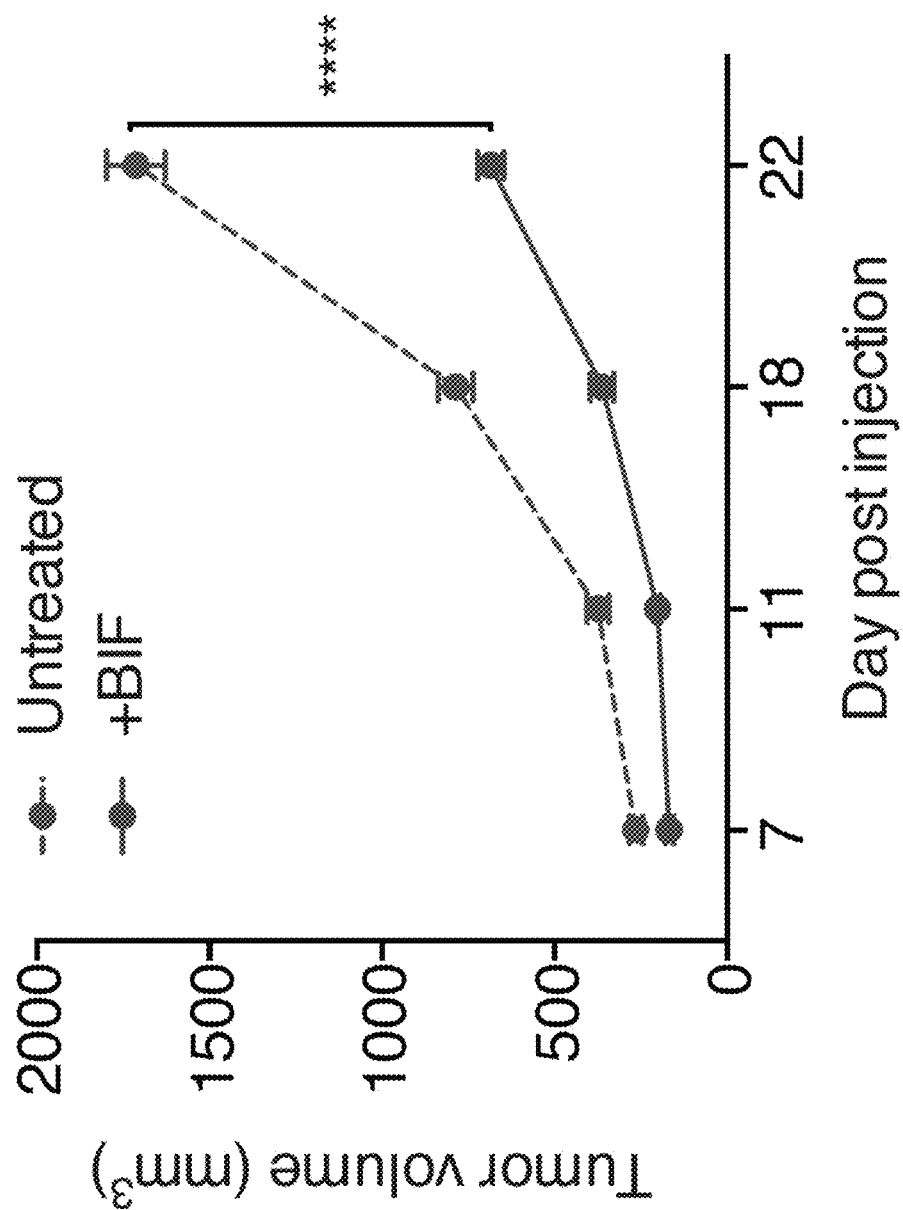

*Bifidobacterium*-treated mice displayed significantly improved tumor control in comparison to non-*Bifidobacterium* treated counterparts (FIG. 8E), which was accompanied by robust induction of tumor-specific T cells in the periphery (FIG. 8F) and increased accumulation of antigen-specific CD8+ T cells within the tumor (FIG. 8G and FIG. 9C). These effects were durable for several weeks (FIG. 9D-E).

Figure 10A:
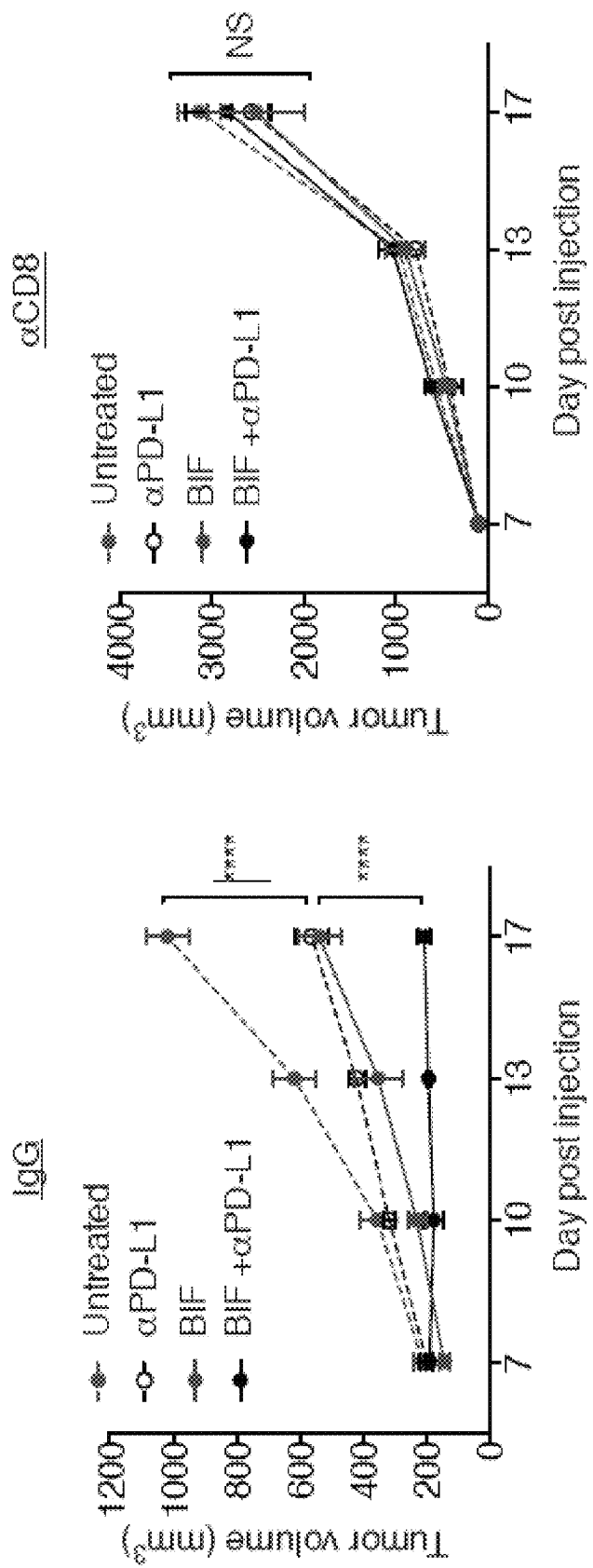
FIG. 10A-D. (A) B16.SIY tumor growth for isotype-treated (left) or CD8-depleted (right) groups as in FIG. 3E. (B) Number of colony forming units (CFU) of live and heat inactivated bifidobacteria, plated in RCM agar following serial dilution in reduced PBS and incubated in an anaerobic chamber for 72 hours. Bars represent 2 replicate plates of each dilution. (C) B16.SIY tumor growth kinetics in TAC mice, untreated or treated with live *Bifidobacterium*, heat inactivated *Bifidobacterium* or JAX fecal material 7 and 14 days post tumor implantation. (D) Percentage of tumor-infiltrating SIY$^+$ T cells of total CD8$^+$ T cells for treatment groups as in (C), determined by flow cytometry 14 days after start of treatment.
Figure 10D:
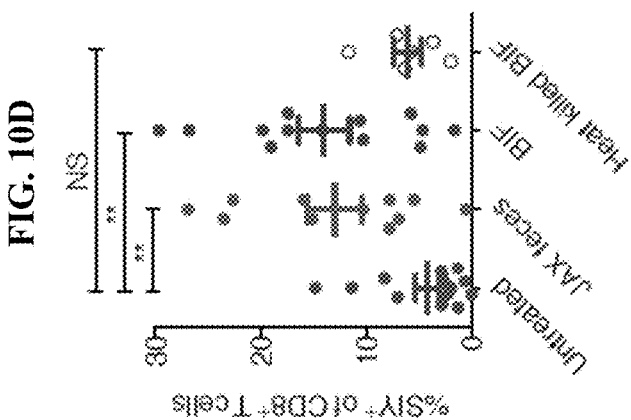
Figure 10C:
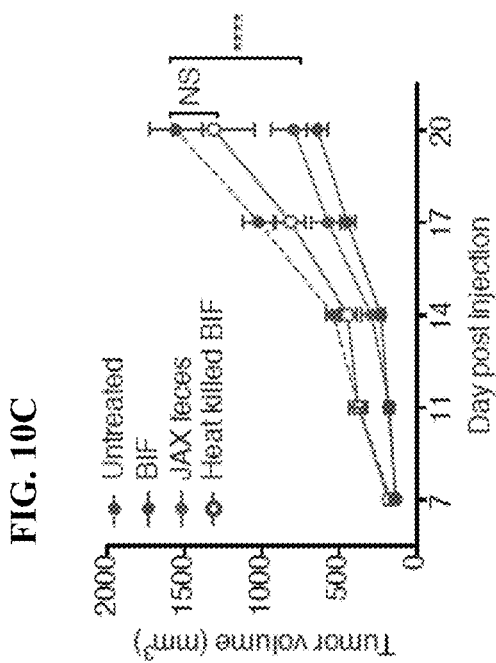
Figure 10B:
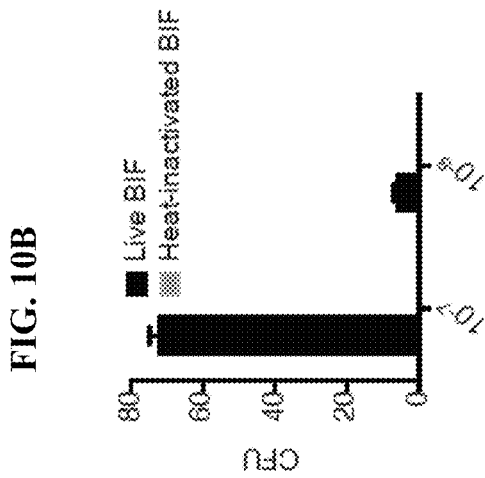

The therapeutic effect of *Bifidobacterium* feeding was abrogated in CD8-depleted mice (FIG. 10A), suggesting that the mechanism was not direct but rather through host anti-tumor T cell responses. Heat inactivation of the bacteria prior to oral administration also abrogated the therapeutic effect on tumor growth and reduced tumor-specific T cell responses to baseline (FIG. 10B-D), suggesting that the anti-tumor effect requires live bacteria. As an alternative strategy, the therapeutic effect of *B. breve* and *B. longum* strains obtained from the ATCC was tested, which also showed significantly improved tumor control (FIG. 11A). Administration of *Bifidobacterium* to TAC mice inoculated with B16 parental tumor cells or MB49 bladder cancer cells also resulted in delayed tumor outgrowth (FIGS. 11, B and C respectively). Oral administration of *Lactobacillus murinus* to TAC mice, which was not among the overrepresented taxa in JAX-fed mice, had no effect on tumor growth (FIG. 11D) or on tumor-specific T cell responses (FIG. 11E), suggesting that modulation of anti-tumor immunity depends on the specific bacteria administered. Collectively, these data point to *Bifidobacterium* as a positive regulator of anti-tumor immunity in vivo.

Figure 12A:
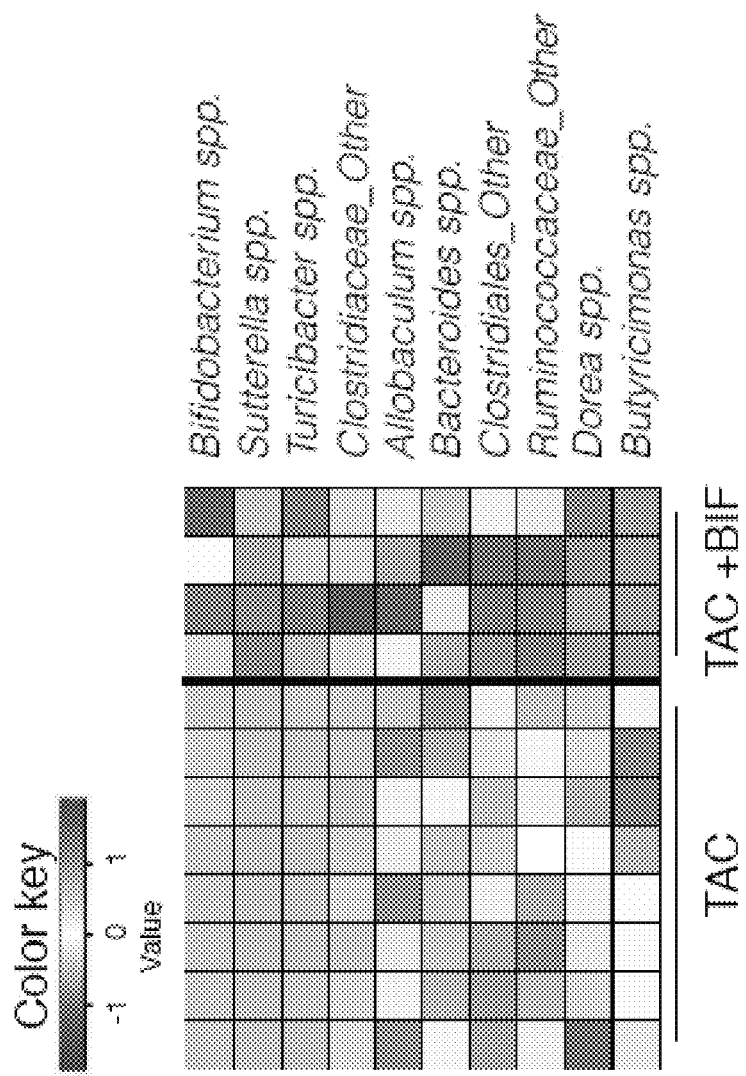
FIG. 12A-C. (A) Heatmap demonstrating relative abundance of significantly altered genus-level taxa in *Bifidobacterium*-fed TAC mice FDR<0.05 (non-parametric t-test); columns depict individual mice; n=4-8 mice per group. (B) Frequency of CD4+ FOXP3+ T cells in tumors isolated from JAX and TAC mice 21 days post tumor inoculation, assessed by flow cytometry; representative plot (top), quantification (bottom). (C) Evaluation of translocation of *Bifidobacterium* into mesenteric lymph nodes (mLN), spleen and tumor of TAC, JAX and *Bifidobacterium*-inoculated mice, assessed by qPCR.
Figure 12B:
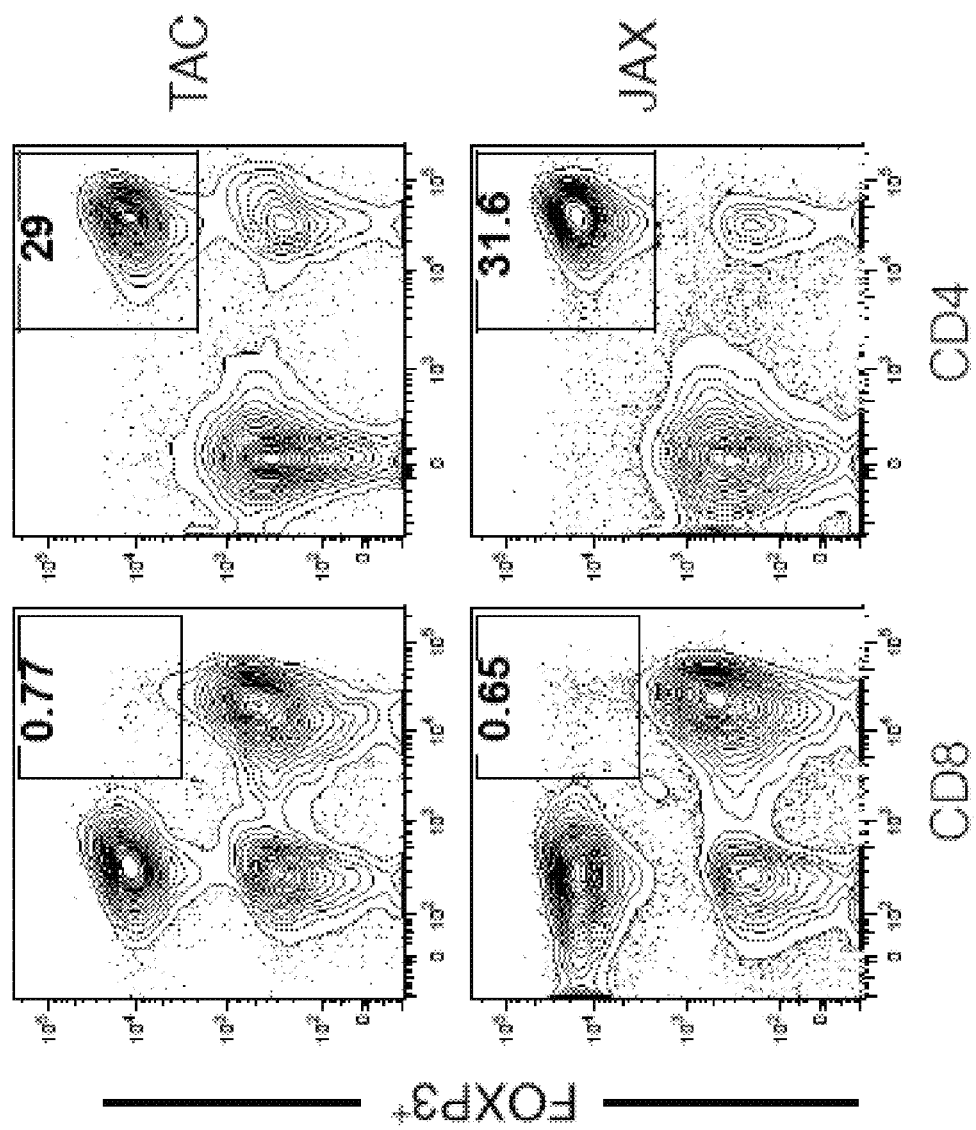

Upon inoculation with *Bifidobacterium*, a small set of species were altered in parallel with *Bifidobacterium* (ANOSIM, p=0.003, FIG. 12A), however, they largely did not resemble the changes observed with JAX-feces administration. Although reductions were observed (~2-10 fold) in members of the order Clostridiales as well as in butyrate-producing species upon *Bifidobacterium* inoculation, which could point to an inhibitory effect on the regulatory T cell compartment, no difference was observed in the frequency of $CD4^+$ $Foxp3^+$ T cells in tumors isolated from JAX and TAC mice (FIG. 12B). Thus, it is unlikely that *Bifidobacterium* is acting primarily through modulation of the abundance of other bacteria.

Figure 12C:
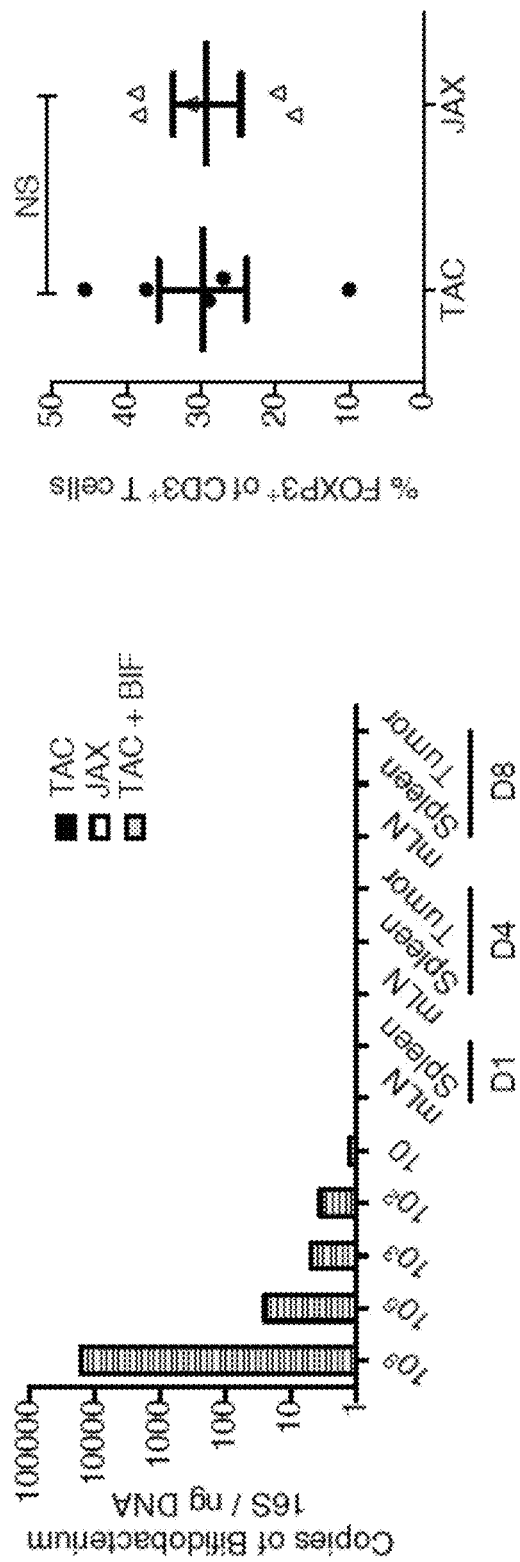

It was next assessed whether translocation of *Bifidobacterium* was occurring into the mesenteric lymph nodes, spleen or tumor, however no *Bifidobacterium* was detected in any of the organs isolated from *Bifidobacterium*-gavaged tumor-bearing mice (FIG. 12C). It was thus concluded that the observed systemic immunological effects are occurring independently of bacterial translocation.

Figure 3D:
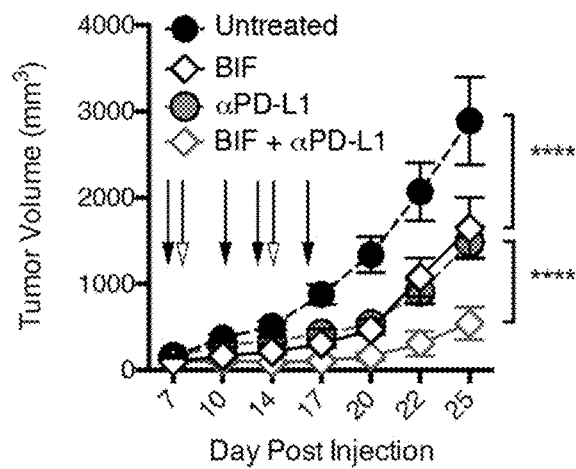
Figure 3E:
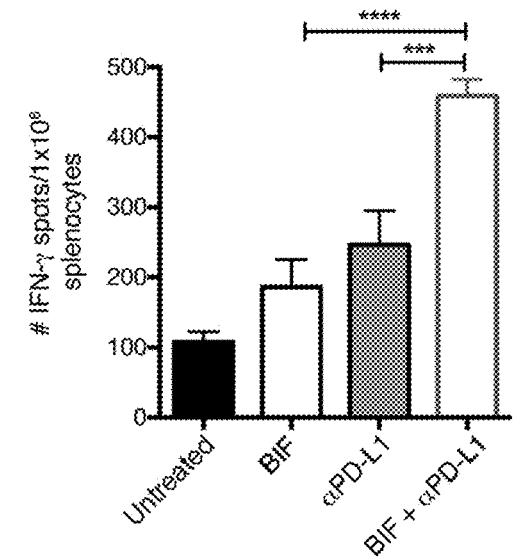
Figure 3F:
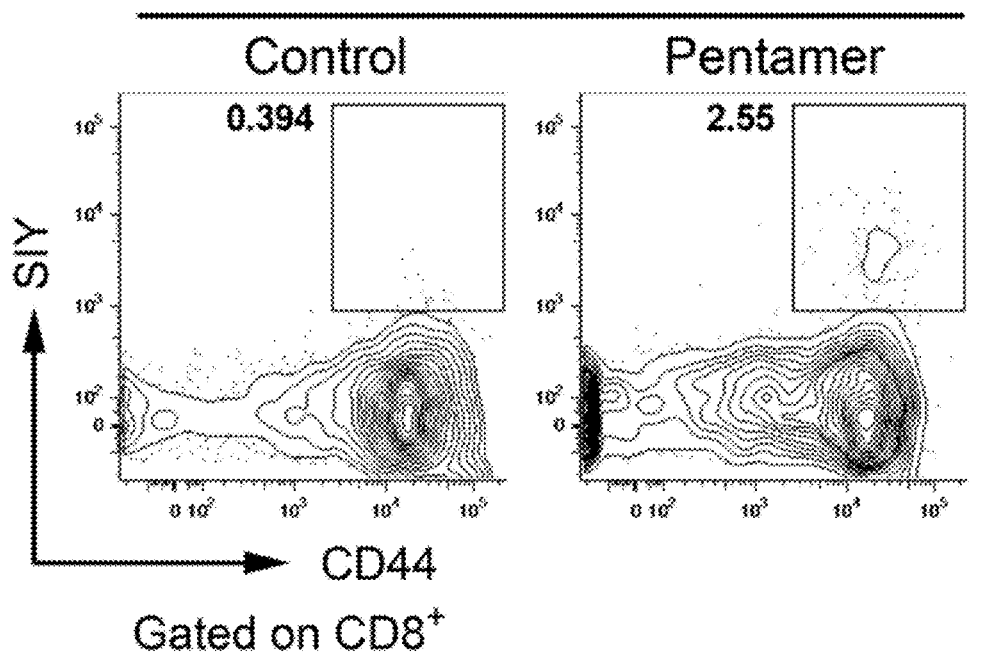
Figure 3F:
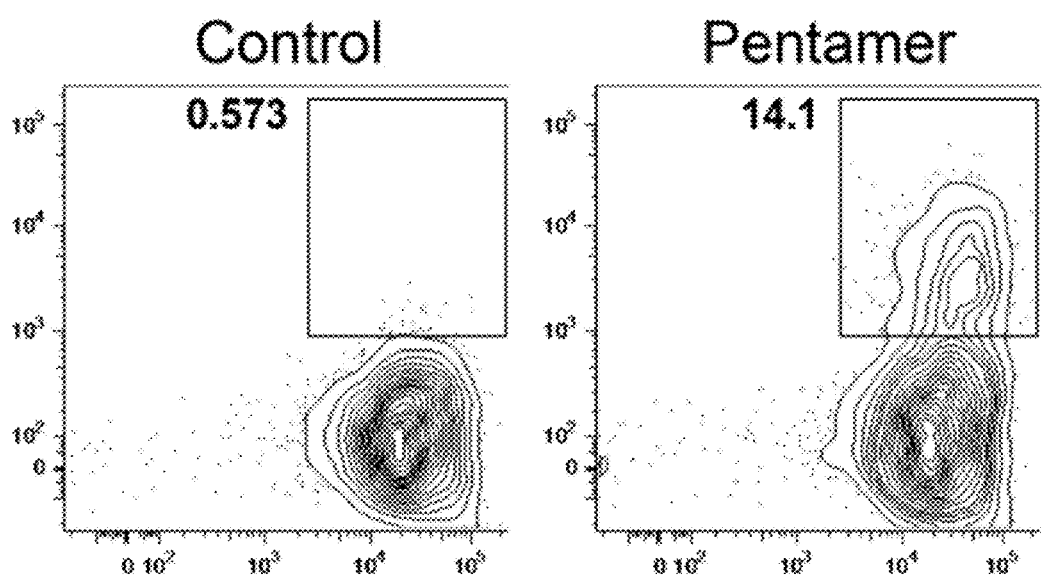
Figure 3F:
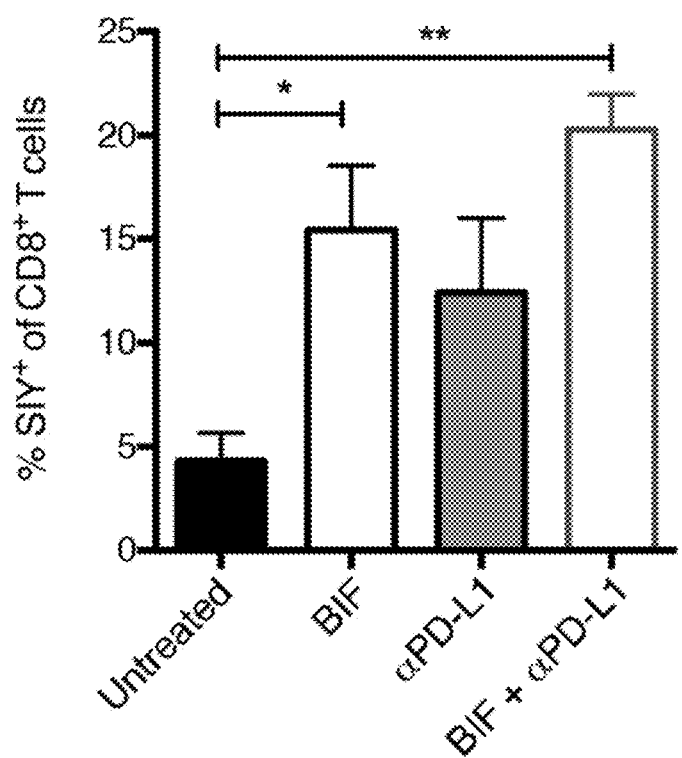
Figure 3G:
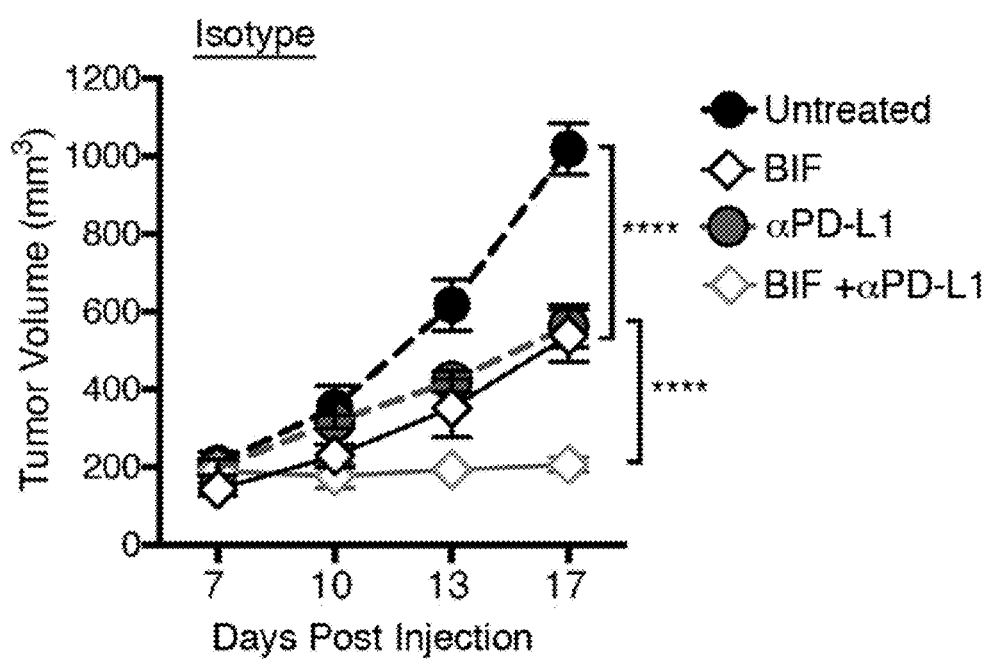
Figure 3G:
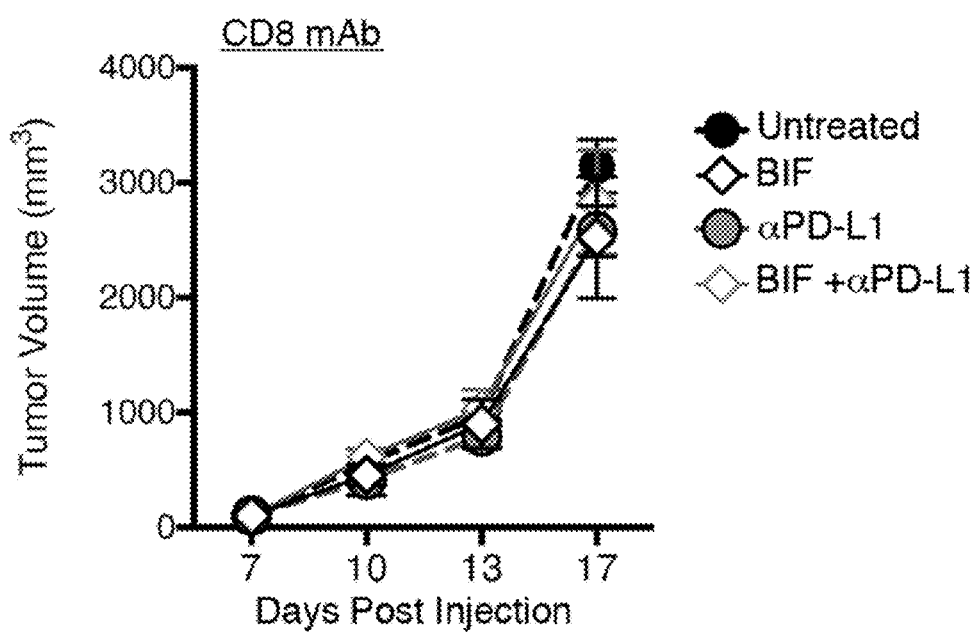
Figure 6B:
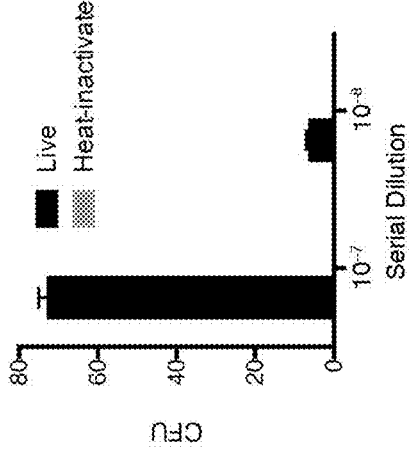
Figure 6C:
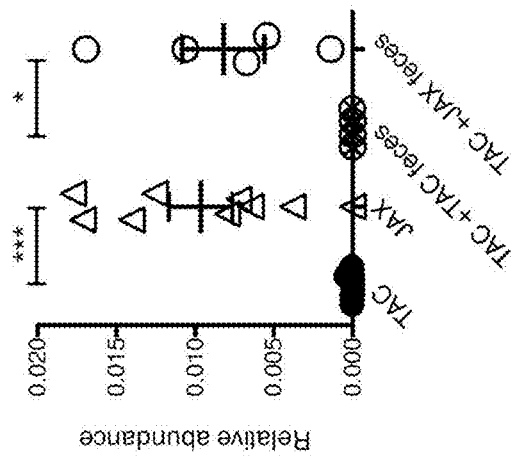
Figure 6F:
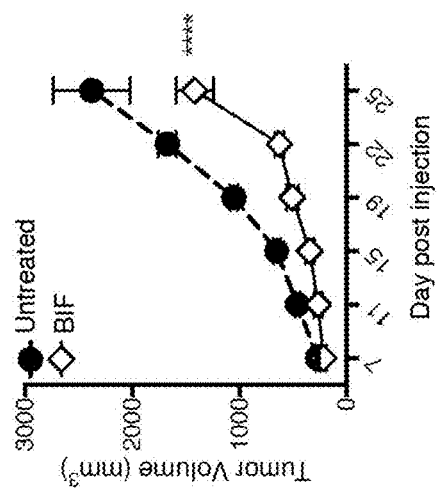
Figure 6E:
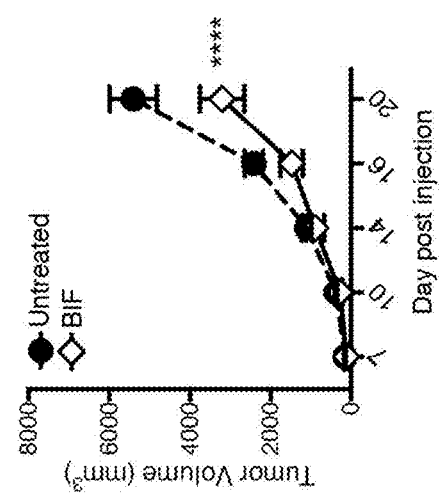
Figure 6D:
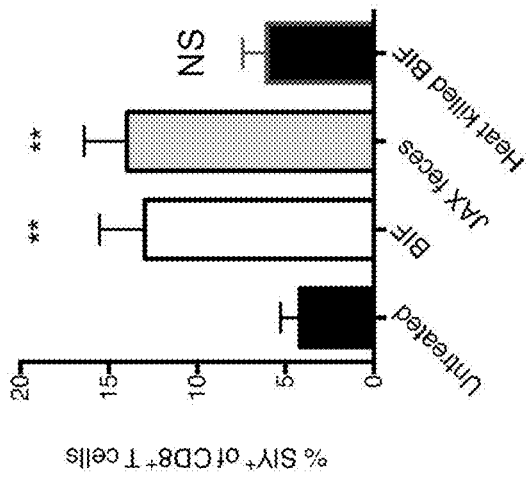
Figure 6H:
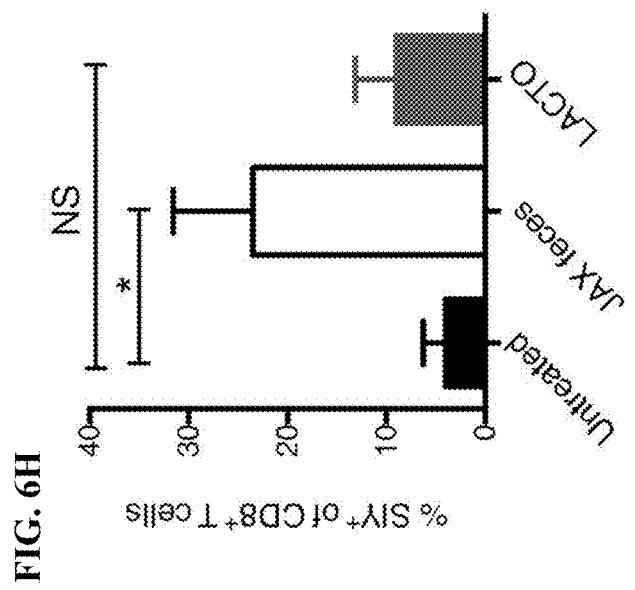
Figure 6G:
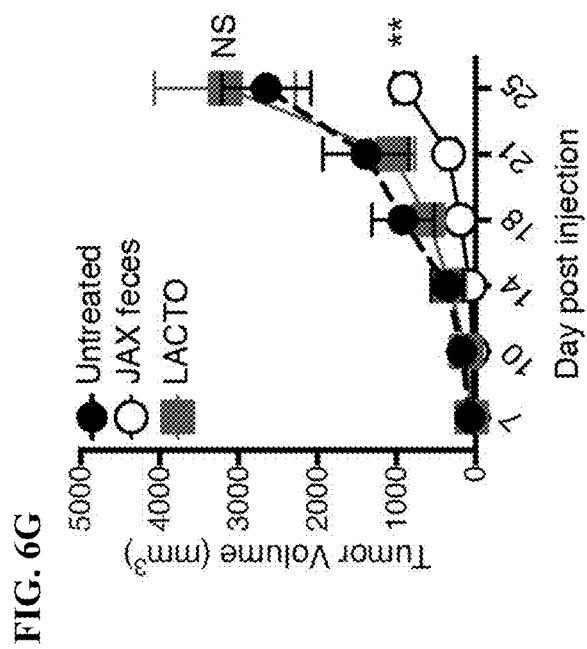

To test whether *Bifidobacterium* spp may be sufficient to augment protective immunity against tumors, we administered a combination of four *Bifidobacterium* species was administered by oral gavage, alone or in combination with αPD-L1, to TAC recipients bearing 7-day established tumors. *Bifidobacterium*-treated mice displayed significantly improved tumor control in comparison to non-*Bifidobacterium* treated counterparts (FIG. 3D), which was accompanied by robust induction of tumor-specific T cells in the periphery (FIG. 3E) and markedly increased accumulation of antigen-specific CD8$^+$ T cells within the tumor (FIG. 3F). This therapeutic effect was completely abrogated in CD8-depleted mice (FIG. 3G), arguing that the mechanism was not direct but rather through host anti-tumor T cell responses. Heat inactivation of the bacteria prior to oral administration also abrogated the therapeutic effect on tumor growth and reduced tumor-specific T cell responses to baseline (FIG. 6B-D), indicating that the anti-tumor effect requires live bacteria. Administration of *Bifidobacterium* to TAC mice inoculated with B16 parental tumor cells or MB49 bladder cancer cells also resulted in delayed tumor outgrowth (FIG. 6E-F). Oral administration of *Lactobacillus murinus* to TAC mice, which was not among the overrepresented taxa in JAX or JAX-fed mice, had no effect on tumor growth (FIG. 6G) nor on tumor-specific T cell responses (FIG. 6H), indicating that modulation of commensal bacterial communities through introduction of new bacteria in itself does not induce immunity to tumors, but rather immunity depends on the specific bacteria administered. Collectively, data identify *Bifidobacterium* as a positive regulator of anti-tumor immunity in vivo.

Figure 4A:
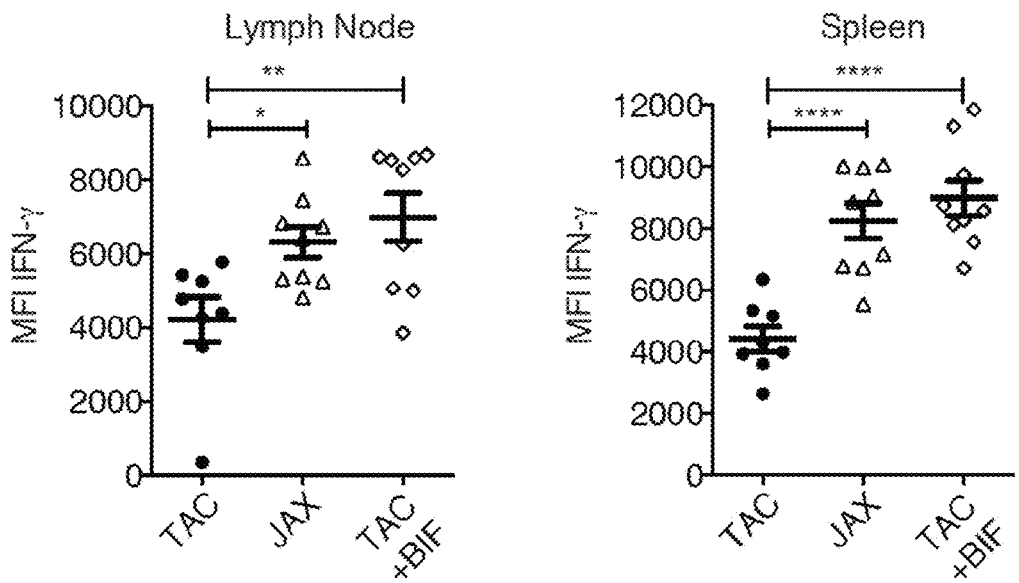
FIG. 4A-E. Dendritic cells isolated from JAX and *Bifidobacterium*-fed TAC mice show increased expression of genes associated with antitumor immunity and heightened capability for T cell activation (A) Quantification of IFN-γ MFI (mean fluorescence intensity) of 2C CD8$^+$ T cells in the tumor-draining lymph node (left) and spleen (right) of TAC, JAX, *Bifidobacterium*-fed TAC mice on day 7 post adoptive transfer. (B) Percentage of MHC Class IIhi DCs in tumors isolated from TAC, JAX, and *Bifidobacterium*-fed TAC mice 40 hours post tumor implantation as assessed by flow cytometry. (C) Enriched biological pathways and functions found within the subset of elevated genes in JAX and *Bifidobacterium*-treated TAC-derived DCs relative to untreated TAC DCs isolated from tumors 40 hrs post tumor inoculation, as assessed by DAVID pathway analysis. Bars indicate the percent of genes in a pathway upregulated in DCs isolated from JAX and *Bifidobacterium*-fed TAC mice. Line indicates p-values calculated by Fisher's exact test. (D) Heat map of key antitumor immunity genes in DCs isolated from JAX, *Bifidobacterium*-treated TAC or untreated TAC mice. Mean fold-change for each gene transcript is shown on the right. (E) Quantification of IFN-γ$^+$ 2C TCR Tg CD8$^+$ T cells stimulated in vitro with DCs purified from peripheral lymphoid tissues of naïve TAC, JAX, and *Bifidobacterium*-treated TAC mice in the presence of different concentrations of SIY peptide.
Figure 4B:
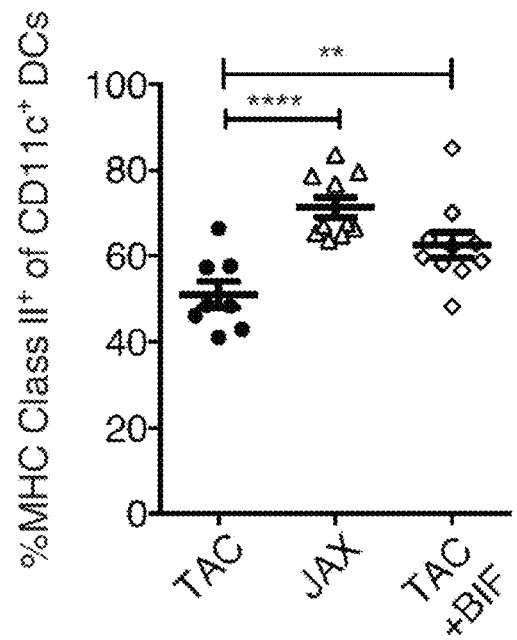
Figure 4C:
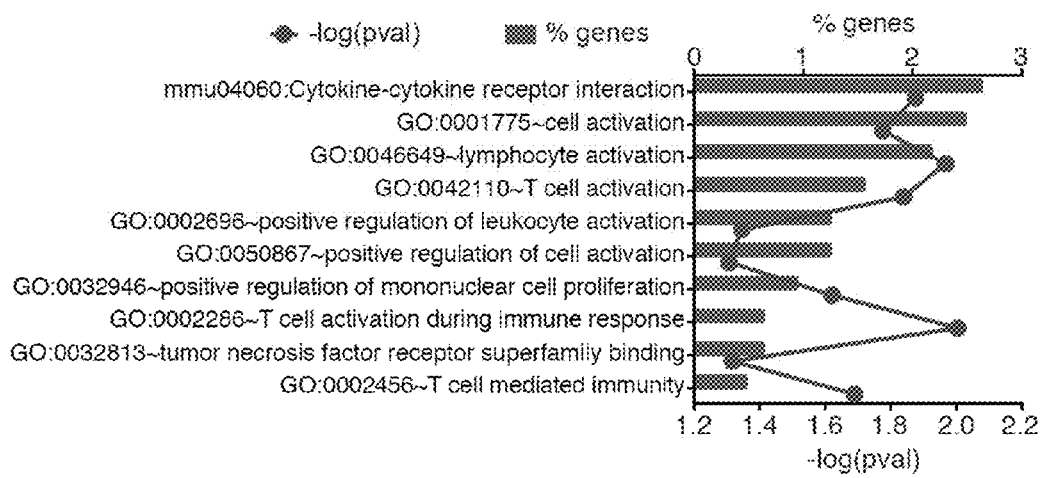
Figure 4E:
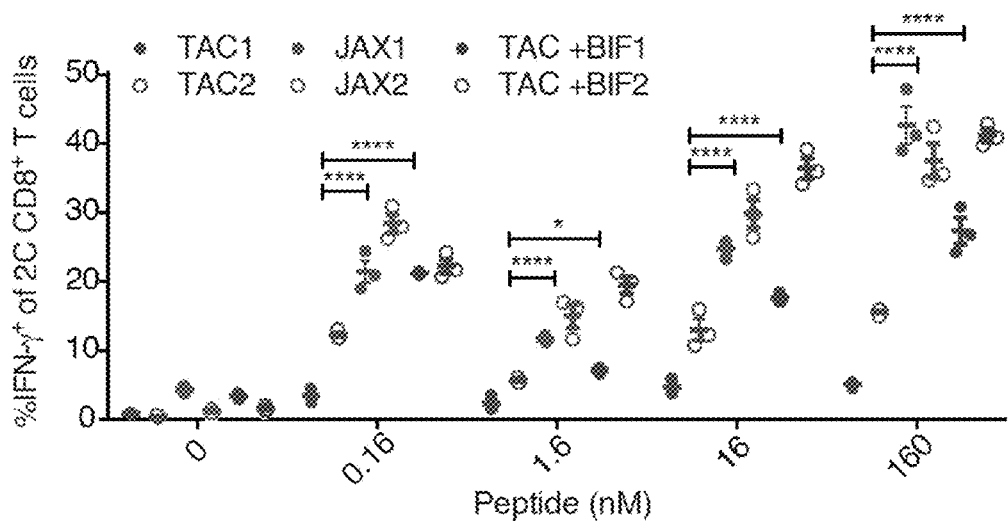
Figure 4D:
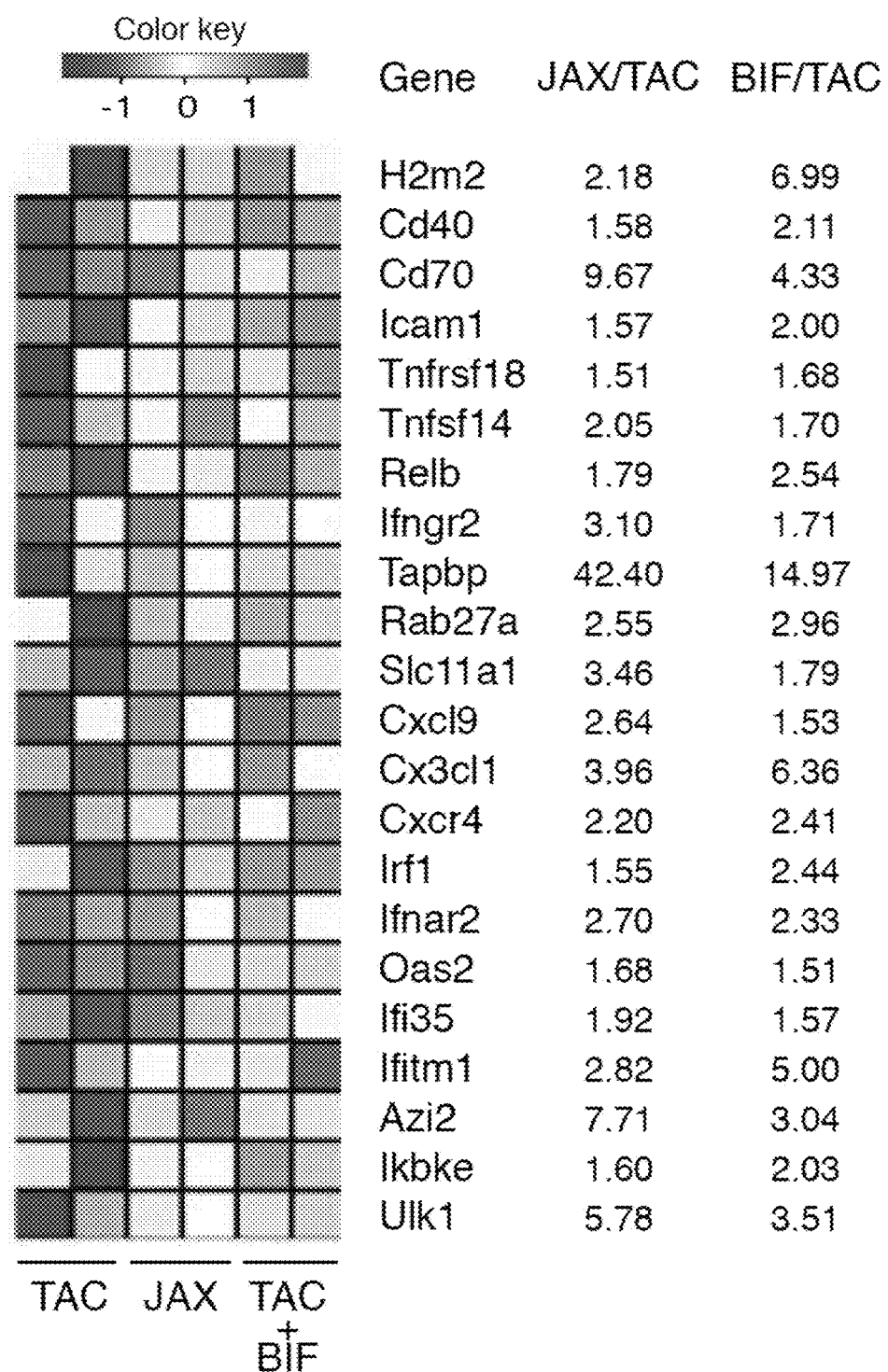
Figure 7A:
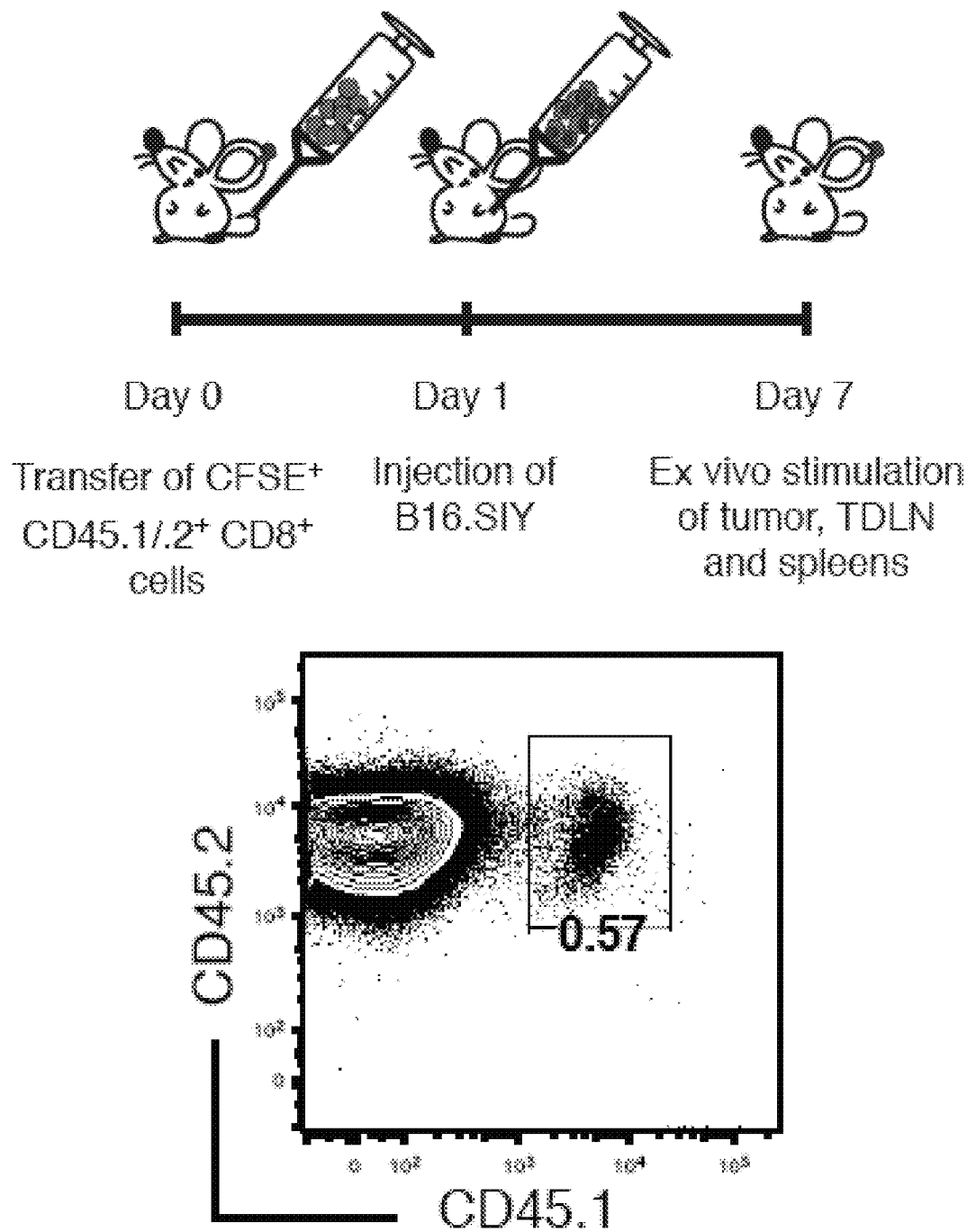
FIG. 7A-B. (A) Schematic of in vivo 2C proliferation assays. CD8+ T cells were isolated from the spleen and lymph node of naïve 2C TCR Tg CD45.1+/.2+mice, labeled with CFSE and injected i.v. into CD45.2+C57BL/6 mice derived from either TAC, JAX or *Bifidobacterium*-treated TAC mice. 24 hours later, mice were inoculated with 1×106 B16.SIY melanoma cells s.c. Spleen and tumor-draining lymph node were harvested and restimulated ex-vivo with SIY peptide. Intracellular IFN-γ production and CFSE dilution were assessed in gated CD45.1+/.2+2C T cells by flow cytometry; TDLN=tumor draining lymph node. (B) Representative CFSE dilution assessed in gated CD45.1+/.2+2C T cells by flow cytometry (left) and quantification (right).
Figure 7B:
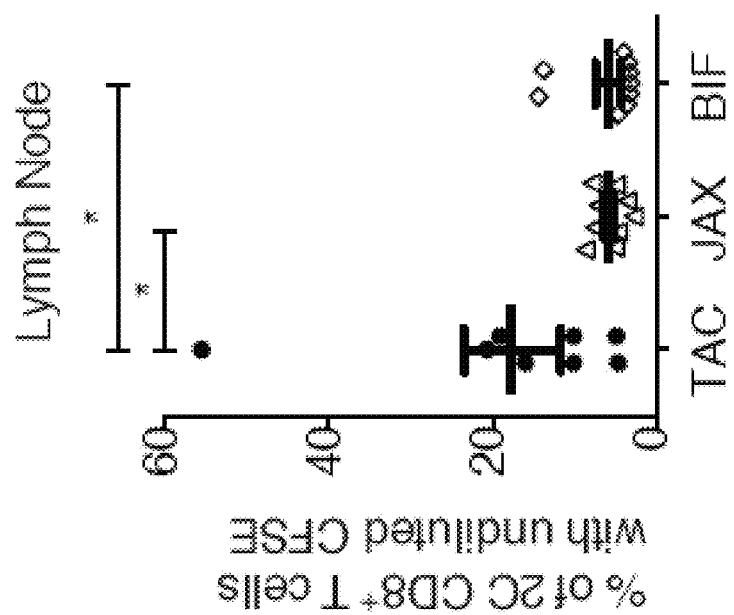
Figure 13A:
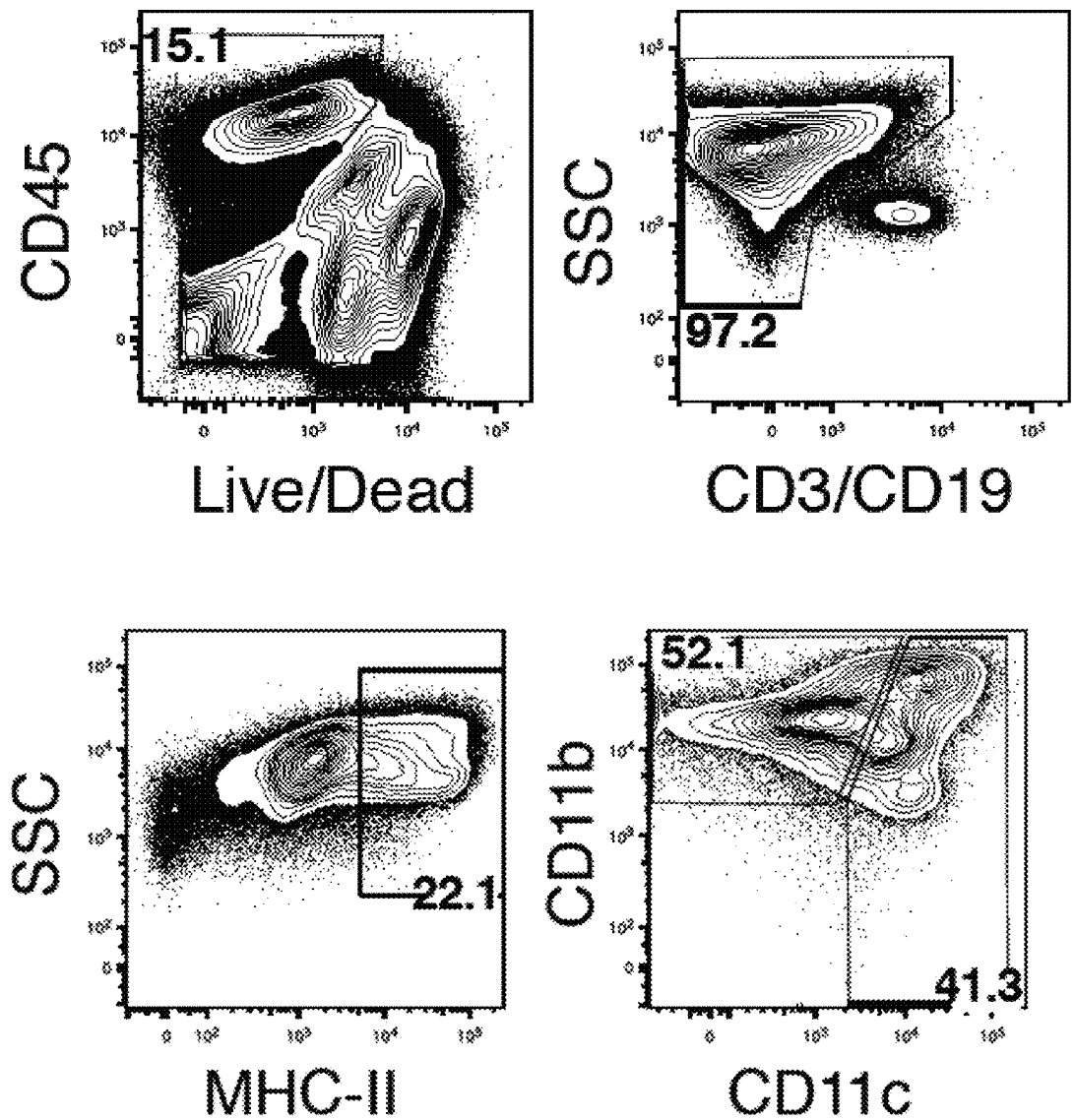
FIG. 13A-C. (A) Representative plots depicting the strategy for isolation of DCs from tumors in JAX, TAC and *Bifidobacterium*-treated TAC mice: live CD45+CD3−CD19−MHCIIhiCD11c+ dendritic cells were sorted as shown. (B) All enriched biological pathways and functions found within the subset of elevated genes (fold change ≥1.5) in JAX and *Bifidobacterium*-treated TAC-derived DCs relative to untreated TAC DCs isolated from tumors 40 hrs post inoculation, as assessed by DAVID pathway analysis. (C) qPCR validation of genes identified by microarray gene expression profiling as in (B).
Figure 13B:
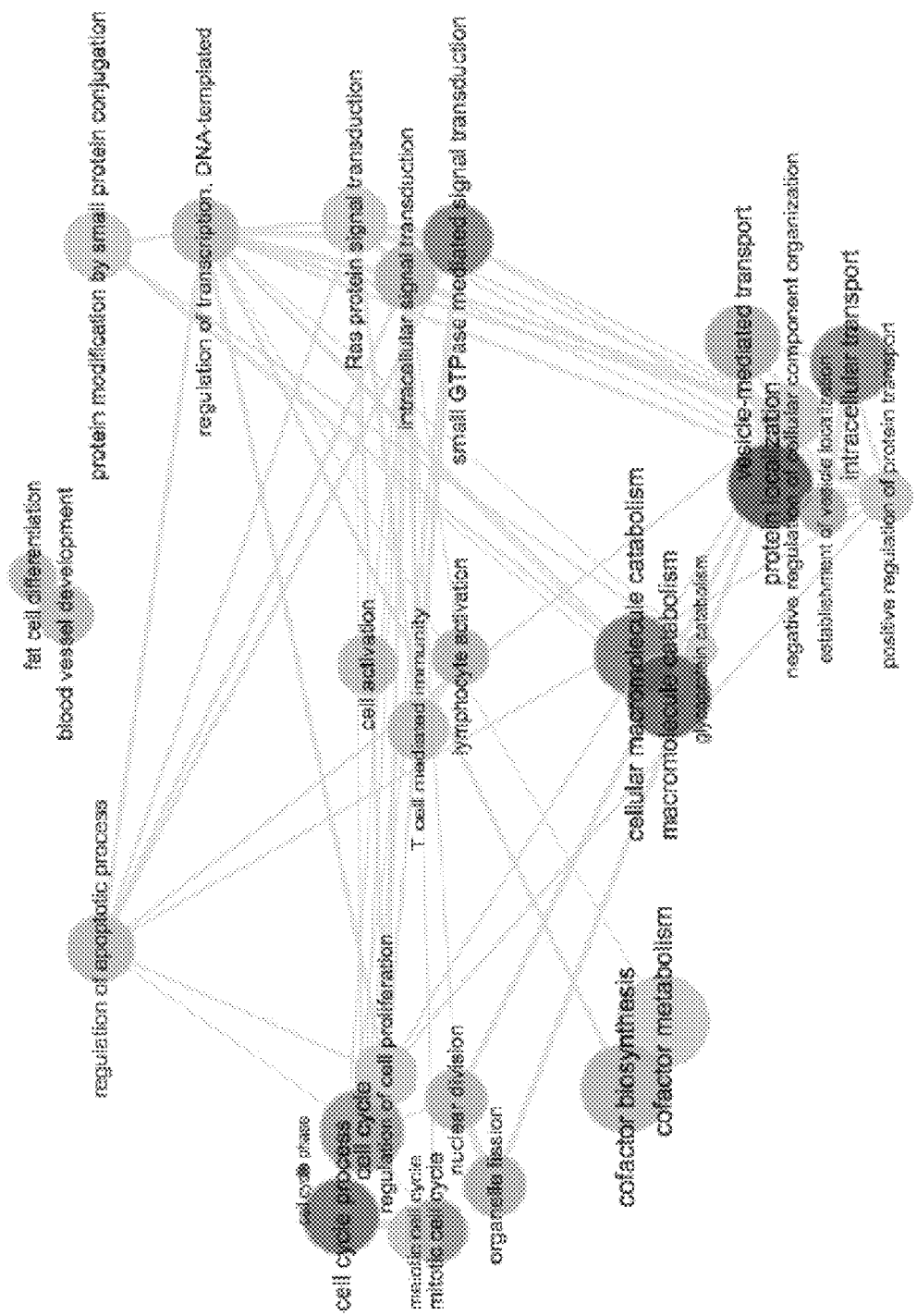
Figure 13C:
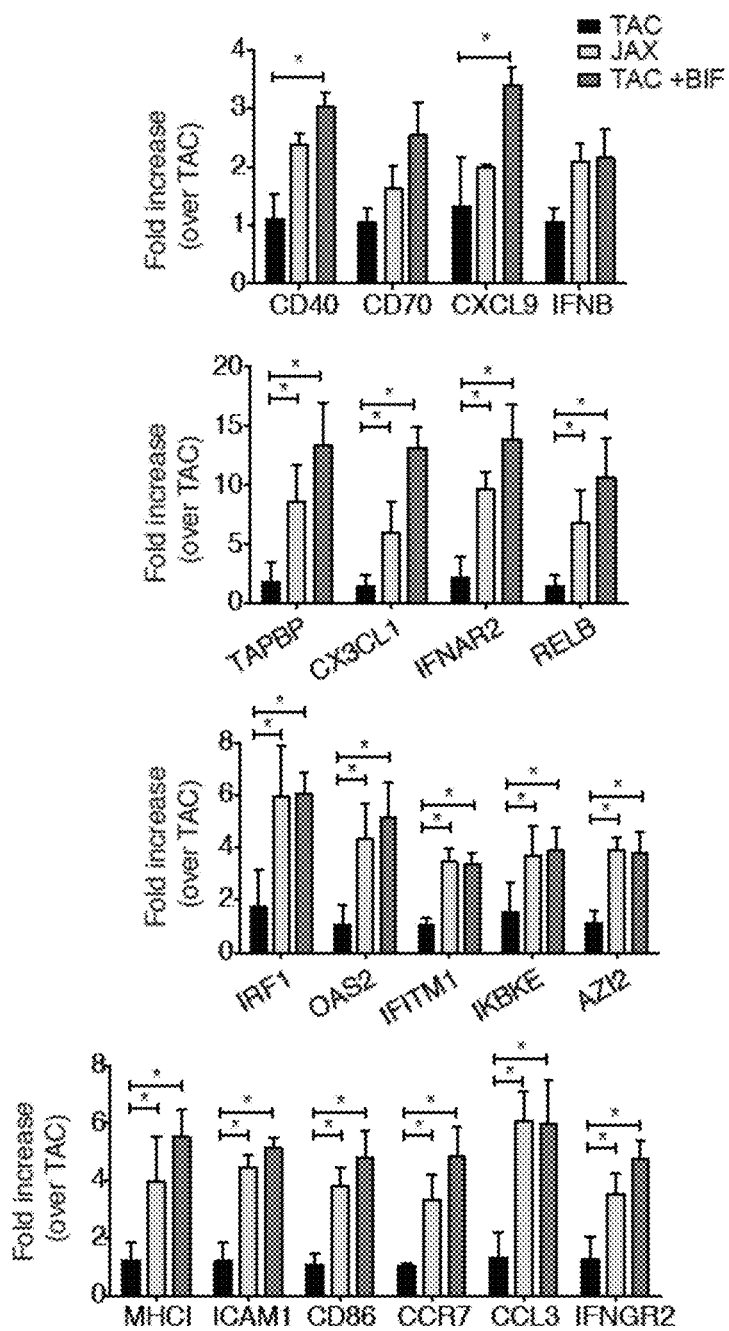

To interrogate mechanisms underlying the observed differences in T cell responses between JAX and TAC mice, we transferred CFSE-labeled SIY-specific 2C TCR Tg T cells into tumor-bearing mice and tested their proliferation and acquisition of IFN-γ production ex vivo (FIG. 7A). CD8$^+$ SIY-specific 2C TCR Tg T cells exposed to tumors in JAX mice exhibited similar expansion in the tumor-draining lymph node as compared to their counterparts in TAC mice (FIG. 7B). However, they produced markedly greater IFN-γ in both the tumor draining lymph node and the spleen of JAX tumor-bearing mice (FIGS. 4A and 4B), suggesting that signals upstream of T cells in the JAX environment enhanced acquisition of T cell effector function. These data indicated an improvement in immune responses upstream of T cells, at the level of host dendritic cells (DCs). Genome-wide transcriptional profiling of early tumor-infiltrating DCs isolated from JAX, TAC and *Bifidobacterium*-treated TAC mice was employed (FIG. 13A). In total, there were 761 gene transcripts upregulated by ≥1.5-fold in both JAX and *Bifidobacterium*-treated TAC-derived DCs relative to DCs from untreated TAC mice (FIG. 4C). Pathway analysis identified cytokine-cytokine receptor interaction, T cell activation, and positive regulation of mononuclear cell proliferation as significantly enriched pathways among upregulated genes (FIG. 4C and FIG. 13B). Many of these genes have been shown to be critical for anti-tumor responses including those involved in CD8$^+$ T cell activation and costimulation (H2-m2(MHC-I), Cd40, Cd70, Icam1)) (Mackey et al. Journal of immunology (Baltimore, Md.: 1950) 161, 2094-2098 (1998); Scholer et al. Immunity 28, 258-270 (2008); Bak et al. Journal of immunology (Baltimore, Md.: 1950) 189, 1708-1716 (2012); herein incorporated by reference in their entireties), DC maturation (Relb, Ifngr2) (Pan et al. Immunology letters 94, 141-151 (2004); Pettit et al. Journal of immunology (Baltimore, Md.: 1950) 159, 3681-3691 (1997); herein incorporated by reference in their entireties), antigen processing and cross presentation (Tapbp, Rab27a, Slc11a1) (Compeer et al. Frontiers in Immunology 3, (2012); Jancic et al. Nature cell biology 9, 367-378 (2007); Stober et al. Infection and Immunity 75, 5059-5067 (2007); herein incorporated by reference in their entireties), chemokine-mediated recruitment of immune cells to the tumor microenvironment (Cxcl9, Cx3cl1, Cxcr4) (Kabashima et al. The American Journal of Pathology 171, 1249-1257 (2007); Nukiwa et al. European journal of immunology 36, 1019-1027 (2006); Zhang et al. New England Journal of Medicine 348, 203-213 (2003); herein incorporated by reference in their entireties) and type I interferon signaling (Irf1, Ifnar2, Oas2, Ifi35, Ifitm1) (Fuertes et al. The Journal of experimental medicine 208, 2005-2016 (2011); Woo et al. Immunity 41, 830-842 10; herein incorporated by reference in their entireties) (FIG. 4D). Expression of these genes was also strongly induced in murine bone marrow-derived DCs stimulated with *Bifidobacterium* in vitro. Taken together, these data indicate that commensal bacteria-derived (e.g., *Bifidobacterium*-derived) signals modulate the activation of innate antigen-presenting cells, which in turn support improved activation of tumor antigen-specific CD8$^+$ T cells.

Figure 14A:
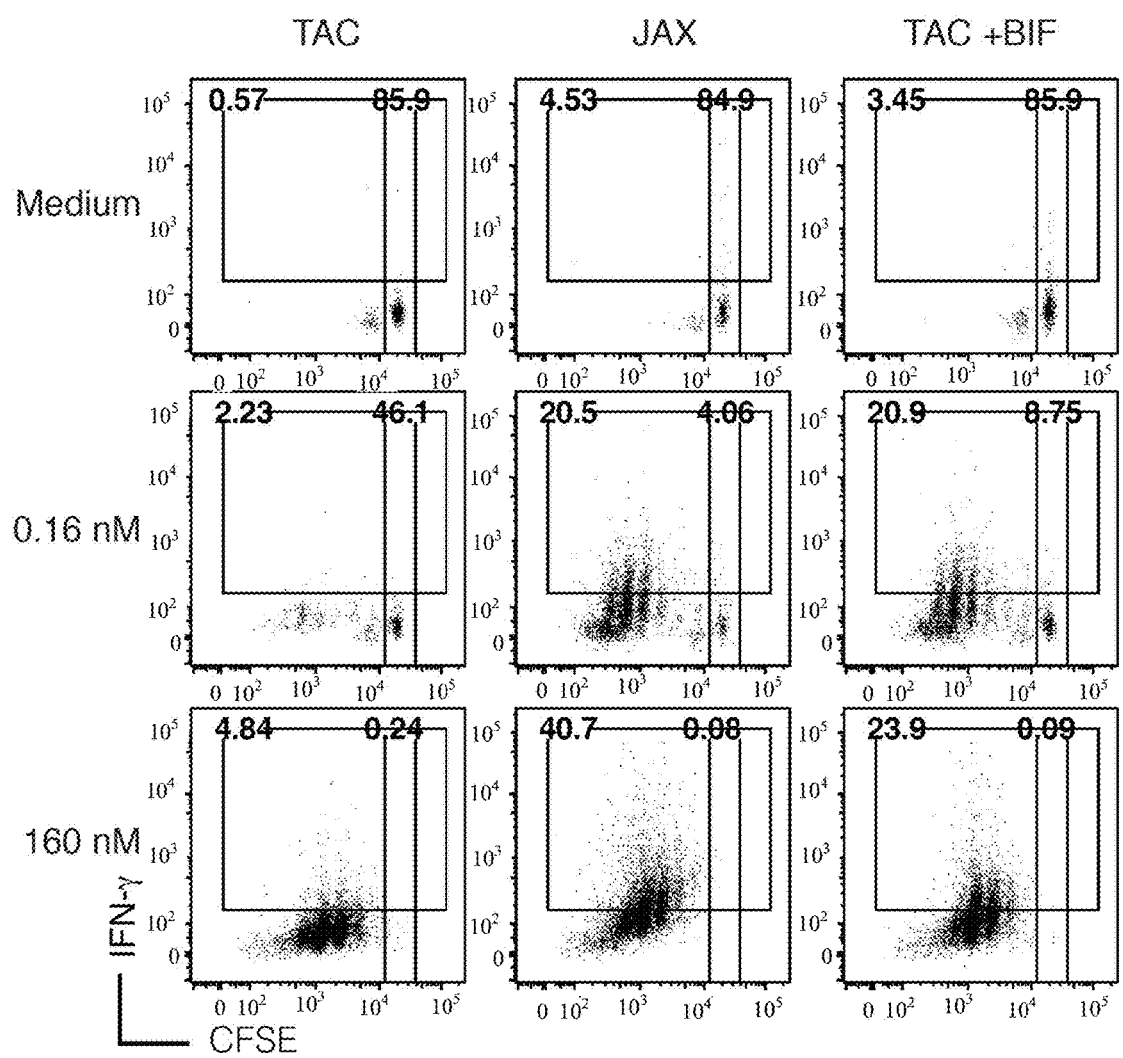
FIG. 14A-B. (A) Representative flow plots of CFSE dilution and IFN-γ production in 2C CD8+ T cells stimulated in vitro with DCs purified from naive TAC, JAX.
Figure 14B:
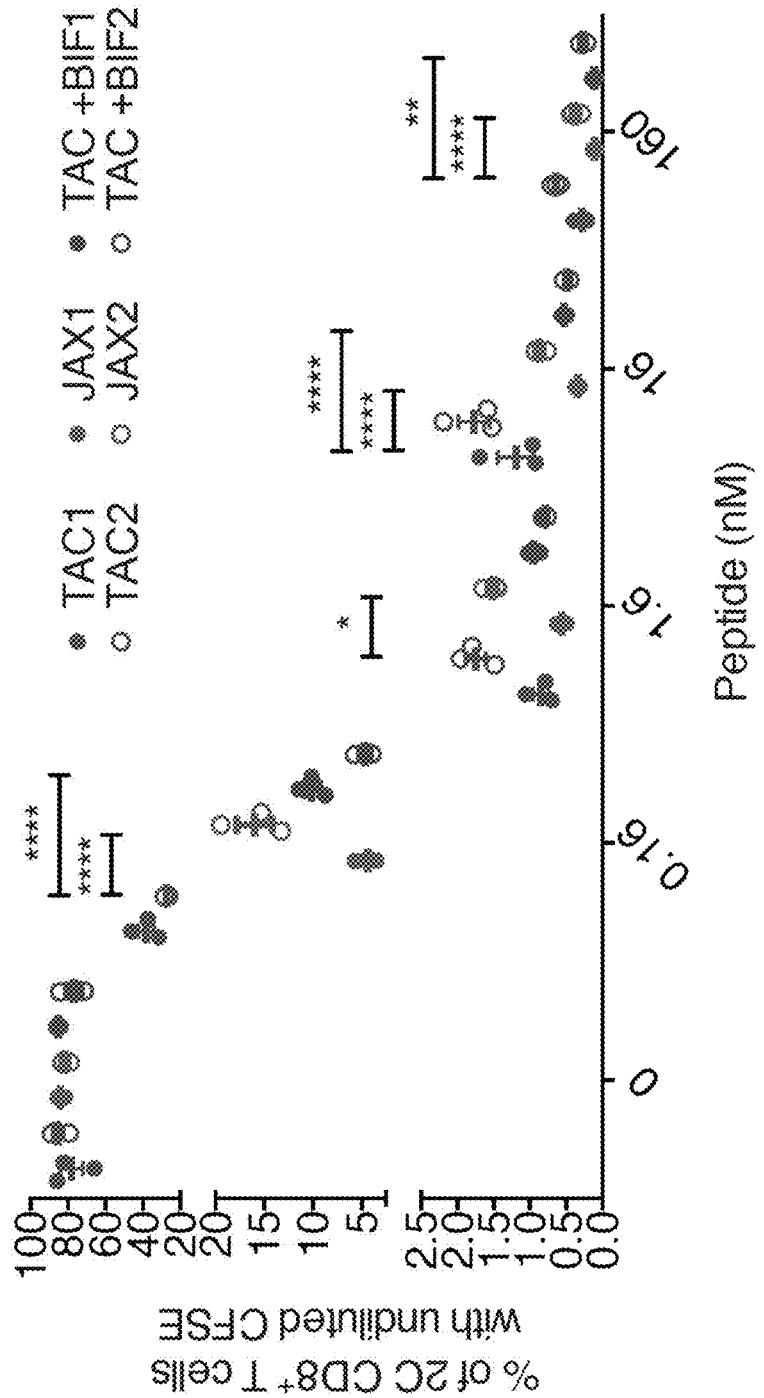

To test whether functional differences in DCs isolated from TAC, JAX and *Bifidobacterium*-treated TAC mice could be sufficient to explain the differences in T cell priming observed in vivo, DCs were purified from lymphoid tissues of naïve TAC, JAX, and *Bifidobacterium*-treated TAC mice and tested their ability to induce CFSE-labeled CD8$^+$ SIY$^-$ specific 2C TCR Tg T cell proliferation and acquisition of IFN-γ production in vitro. DCs purified from JAX and *Bifidobacterium*-treated TAC mice induced 2C T cell proliferation at lower antigen concentration compared to DCs purified from naïve TAC mice (FIGS. 14, A and B). Furthermore, at all antigen concentrations, JAX-derived DCs elicited elevated levels of T cell IFN-γ production (FIG. 4E and FIG. 14A). Similar effects were observed upon oral administration of *Bifidobacterium* to TAC mice prior to DC isolation (FIG. 4E and FIG. 14A). Taken together, these data indicate that commensal *Bifidobacterium*-derived signals modulate the activation of DCs in the steady state, which in turn supports improved effector function of tumor-specific CD8$^+$ T cells.

Experiments conducted during development of embodiments herein demonstrate an unexpected role for commensal microflora (e.g., *Bifidobacterium*) in enhancing anti-tumor immunity. These data support the idea that one source of inter-subject heterogeneity with regard to spontaneous anti-tumor immunity and therapeutic effects of antibodies targeting the PD-1/PD-L1 axis may be the specific composition of gut microbes, which can be manipulated for therapeutic benefit.

REFERENCES

The following references, some of which are cited above, are herein incorporated by reference in their entireties.

1. Hodi et al. The New England journal of medicine 363, 711-723 (2010).
2. Hamid et al. The New England journal of medicine 369, 134-144 (2013).
3. Tumeh et al. Nature 515, 568-571 (2014).
4. Spranger et al. Science translational medicine 5, 200ra116 (2013).
5. Ji et al. Cancer immunology, immunotherapy: CII 61, 1019-1031 (2012).
6. Gajewski et al. Cancer journal 16, 399-403 (2010).
7. Mazmanian et al. Cell 122, 107-118 (2005).
8. Round et al. Proceedings of the National Academy of Sciences of the United States of America 107, 12204-12209 (2010).
9. Ivanov et al. Cell 139, 485-498 (2009).
10. Wu et al. Immunity 32, 815-827 (2010).
11. Goto et al. Immunity 40, 594-607 (2014).
12. Ganal et al. Immunity 37, 171-186 (2012).
13. Abt et al. Immunity 37, 158-170 (2012).
14. Iida et al. Science (New York, N.Y.) 342, 967-970 (2013).
15. Viaud et al. Science (New York, N.Y.) 342, 971-976 (2013).
16. Lopez et al. International journal of food microbiology 138, 157-165 (2010).
17. Ménard et al. Applied and Environmental Microbiology 74, 660-666 (2008).
18. Dong et al. Early human development 86, 51-58 (2010).
19. Mackey et al. Journal of immunology (Baltimore, Md.: 1950) 161, 2094-2098 (1998).
20. Scholer et al. Immunity 28, 258-270 (2008).
21. Bak et al. Journal of immunology (Baltimore, Md.: 1950) 189, 1708-1716 (2012).
22. Pan et al. Immunology letters 94, 141-151 (2004).
23. Pettit et al. Journal of immunology (Baltimore, Md.: 1950) 159, 3681-3691 (1997).
24. Compeer et al. Frontiers in Immunology 3, (2012).
25. Jancic et al. Nature cell biology 9, 367-378 (2007).
26. Stober et al. Infection and Immunity 75, 5059-5067 (2007).
27. Kabashima et al. The American Journal of Pathology 171, 1249-1257 (2007).
28. Nukiwa et al. European journal of immunology 36, 1019-1027 (2006).
29. Zhang et al. New England Journal of Medicine 348, 203-213 (2003).
30. Fuertes et al. The Journal of experimental medicine 208, 2005-2016 (2011).
31. Woo et al. Immunity 41, 830-842 10.
32. Blank et al. Cancer research 64, 1140-1145 (2004).
33. Caporaso et al. Bioinformatics 26, 266-267 (2010).
34. McDonald et al. The ISME journal 6, 610-618 (2012).
35. Caporaso et al. Nat Meth 7, 335-336 (2010).
36. Wang et al. Appl Environ Microbiol 73, 5261-5267 (2007).
37. Lozupone et al. Appl Environ Microbiol 71, 8228-8235 (2005).

We claim:

1. A method of treating cancer in a human subject comprising co-administering to the subject an immune checkpoint inhibitor and a bacterial formulation comprising bacteria of the genus *Bifidobacterium*.

2. The method of claim 1, wherein at least 50% of the bacteria in the bacterial formulation are of the genus *Bifidobacterium*.

3. The method of claim 1, wherein at least 90% of the bacteria in the bacterial formulation are of the genus *Bifidobacterium*.

4. The method of claim 1, wherein the bacteria of the genus *Bifidobacterium* comprise bacteria of the species *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, *Bifidobacterium angulatum*, *Bifidobacterium asteroides*, *Bifidobacterium boum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium indicum*, *Bifidobacterium inopinatum*, *Bifidobacterium magnum*, *Bifidobacterium merycicum*, *Bifidobacterium minimum*, *Bifidobacterium pseudolongum*, *Bifidobacterium pullorum*, *Bifidobacterium psychraerophilum*, *Bifidobacterium ruminantium*, *Bifidobacterium saeculare*, *Bifidobacterium scardovii*, *Bifidobacterium simiae*, *Bifidobacterium subtile*, *Bifidobacterium therammcidophilum*, *Bifidobacterium thermophilum*, *Bifidobacterium tsurumiense*, *Bifidobacterium urinalis* or *Bifidobacterium sp.*

5. The method of claim 1, wherein the bacterial formulation is administered by oral administration or rectal administration.

6. The method of claim 5, wherein the bacterial formulation is administered by oral administration.

7. The method of claim 1, wherein the bacterial formulation comprises at least $5\times10^6$ CFU of bacteria of the genus *Bifidobacterium*.

8. The method of claim 1, wherein the bacterial formulation is administered to the subject in two or more doses.

9. The method of claim 8, wherein the administration of the two or more doses are separated by at least 1 week.

10. The method of claim 1, further comprising administering to the subject an antibiotic prior to the administration of the bacterial formulation.

11. The method of claim 10, wherein the antibiotic is administered to the subject at least 1 day before the bacterial formulation is administered to the subject.

12. The method of claim 1, wherein the immune checkpoint inhibitor is a protein or polypeptide that binds to an immune checkpoint protein.

13. The method of claim 12, wherein the immune checkpoint protein is CTLA4, PD-1, PD-L1, PD-L2, A2AR, B7-H3, B7-H4, BTLA, KIR, LAG3, TIM-3 or VISTA.

14. The method of claim 13, wherein the immune checkpoint protein is PD-1 or PD-L1.

15. The method of claim 1, wherein the immune checkpoint inhibitor is an antibody or antigen binding fragment thereof that binds to an immune checkpoint protein.

16. The method of claim 15, wherein the immune checkpoint protein is CTLA4, PD-1, PD-L1, PD-L2, A2AR, B7-H3, B7-H4, BTLA, KIR, LAG3, TIM-3 or VISTA.

17. The method of claim 16, wherein the immune checkpoint protein is PD-1 or PD-L1.

18. The method of claim 1, wherein the immune checkpoint inhibitor is nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010.

19. The method of claim 1, wherein the immune checkpoint inhibitor is administered by intravenous injection, intramuscular injection, intratumoral injection or subcutaneous injection.

20. The method of claim 1, wherein the bacterial formulation comprises at least $5 \times 10^6$ CFU of bacteria of the genus *Bifidobacterium*, and wherein at least 50% of the bacteria in the bacterial formulation are of the genus *Bifidobacterium*.

21. The method of claim 20, wherein at least 90% of the bacteria in the bacterial formulation are of the genus *Bifidobacterium*.

22. The method of claim 20, wherein the bacteria of the genus *Bifidobacterium* comprise bacteria of the species *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, *Bifidobacterium angulatum*, *Bifidobacterium asteroides*, *Bifidobacterium boum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium indicum*, *Bifidobacterium inopinatum*, *Bifidobacterium magnum*, *Bifidobacterium merycicum*, *Bifidobacterium minimum*, *Bifidobacterium pseudolongum*, *Bifidobacterium pullorum*, *Bifidobacterium psychraerophilum*, *Bifidobacterium ruminantium*, *Bifidobacterium saeculare*, *Bifidobacterium scardovii*, *Bifidobacterium simiae*, *Bifidobacterium subtile*, *Bifidobacterium therammcidophilum*, *Bifidobacterium thermophilum*, *Bifidobacterium tsurumiense*, *Bifidobacterium urinalis* or *Bifidobacterium* sp.

23. The method of claim 20, wherein the bacterial formulation is administered by oral administration or rectal administration.

24. The method of claim 23, wherein the bacterial formulation is administered by oral administration.

25. The method of claim 20, wherein the bacterial formulation is administered to the subject in two or more doses.

26. The method of claim 20, further comprising administering to the subject an antibiotic before the bacterial formulation is administered to the subject.

27. The method of claim 20, wherein the immune checkpoint inhibitor is an antibody or antigen binding fragment thereof that binds to CTLA4, PD-1, PD-L1, PD-L2, A2AR, B7-H3, B7-H4, BTLA, KIR, LAG3, TIM-3 or VISTA.

28. The method of claim 20, wherein the immune checkpoint inhibitor is an antibody or antigen binding fragment thereof that binds to PD-1 or PD-L1.

29. The method of claim 20, wherein the immune checkpoint inhibitor is nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010.

\* \* \* \* \*

(12) POST-GRANT REVIEW CERTIFICATE (198th)
United States Patent
Gajewski et al.

(10) Number: US 9,855,302 J1
(45) Certificate Issued: Aug. 20, 2021

(54) TREATMENT OF CANCER BY MANIPULATION OF COMMENSAL MICROFLORA

(71) Applicants: Thomas F. Gajewski; Leticia Corrales; Ayelet Sivan

(72) Inventors: Thomas F. Gajewski; Leticia Corrales; Ayelet Sivan

(73) Assignee: The University of Chicago

Trial Number:

PGR2019-00002 filed Oct. 2, 2018

Post-Grant Review Certificate for:

Patent No.: 9,855,302
Issued: Jan. 2, 2018
Appl. No.: 15/170,284
Filed: Jun. 1, 2016

The results of PGR2019-00002 are reflected in this post-grant review certificate under 35 U.S.C. 328(b).

POST-GRANT REVIEW CERTIFICATE
U.S. Patent 9,855,302 J1
Trial No. PGR2019-00002
Certificate Issued Aug. 20, 2021

AS A RESULT OF THE POST-GRANT REVIEW PROCEEDING, IT HAS BEEN DETERMINED THAT:

Claims 1-29 are cancelled.

\* \* \* \* \*